(12) United States Patent
Xu et al.

(10) Patent No.: US 7,110,106 B2
(45) Date of Patent: Sep. 19, 2006

(54) SURFACE INSPECTION SYSTEM

(75) Inventors: James J. Xu, San Jose, CA (US); Ken K. Lee, Los Altos, CA (US)

(73) Assignee: CoreTech Optical, Inc., San Jose, CA (US)

( * ) Notice: Subject to any disclaimer, the term of this patent is extended or adjusted under 35 U.S.C. 154(b) by 58 days.

(21) Appl. No.: 10/977,084

(22) Filed: Oct. 28, 2004

(65) Prior Publication Data

US 2005/0094864 A1    May 5, 2005

Related U.S. Application Data

(60) Provisional application No. 60/515,462, filed on Oct. 29, 2003.

(51) Int. Cl.
*G01N 21/00* (2006.01)

(52) U.S. Cl. .............. 356/237.5; 356/237.1; 356/237.2

(58) Field of Classification Search .. 356/237.1–237.6, 356/394, 364–370, 430–431; 250/559.18, 250/559.39, 559.4, 559.41, 559.44, 559.46, 250/225

See application file for complete search history.

(56) References Cited

U.S. PATENT DOCUMENTS

| | | | |
|---|---|---|---|
| 4,441,124 A | 4/1984 | Heebner et al. | |
| 4,618,938 A | 10/1986 | Sandland et al. | |
| 4,693,602 A | 9/1987 | Wyatt et al. | |
| 4,720,191 A | 1/1988 | Siegel et al. | |
| 4,764,969 A | 8/1988 | Ohtombe et al. | |
| 4,794,265 A | 12/1988 | Quackenbos et al. | |
| 4,805,123 A | 2/1989 | Specht et al. | |
| 4,845,558 A | 7/1989 | Tsai et al. | |
| 4,898,471 A | 2/1990 | Vaught et al. | |
| 4,926,489 A | 5/1990 | Danielson et al. | |
| 4,991,971 A | 2/1991 | Geary et al. | |
| 5,125,741 A | 6/1992 | Okada et al. | |
| 5,189,481 A | 2/1993 | Jann et al. | |
| 5,355,212 A | 10/1994 | Wells et al. | |
| 5,363,187 A | 11/1994 | Hagiwara et al. | |
| 5,389,794 A | 2/1995 | Allen et al. | |
| 5,424,536 A | 6/1995 | Moriya | |
| 5,448,364 A * | 9/1995 | Moran | 356/430 |
| 5,699,447 A | 12/1997 | Alumot et al. | |
| 5,712,701 A | 1/1998 | Clementi et al. | |

(Continued)

OTHER PUBLICATIONS

U.S. Appl. No. 10/977,138, filed Oct. 28, 2004, Jams J. Xu.

(Continued)

*Primary Examiner*—Layla G. Lauchman
*Assistant Examiner*—Sang H. Nguyen
(74) *Attorney, Agent, or Firm*—D. James Chung; Silicon Edge Law Group LLP

(57) ABSTRACT

An inspection system includes a stage, a light source, and a light collection subsystem is disclosed. The stage supports an article for inspection, the article having a surface. The light source provides light impinging on and scattering from an illumination area of the surface. The light collection system includes a plurality of collectors arranged generally in a semi-spherical layout such that each collector collects at least a portion of the scattering light at a collection polar angle and a collection azimuthal angle that are unique relative to collection polar angle and collection azimuthal angle of other collectors. The collectors are arranged in three rings of collectors. The inspection system includes a plurality of channels where each collector of the light collection subsystem is associated with a channel. The inspection system includes a processor connected to the channels. The processor is adapted to process information from the channels.

20 Claims, 26 Drawing Sheets

U.S. PATENT DOCUMENTS

| | | |
|---|---|---|
| 5,717,485 A | 2/1998 | Ito et al. |
| 5,798,829 A | 8/1998 | Vaez-Iravani |
| 5,798,831 A | 8/1998 | Hagiwara |
| 5,847,821 A | 12/1998 | Tracy et al. |
| 5,864,394 A | 1/1999 | Jordan, III et al. |
| 5,883,710 A | 3/1999 | Nikoonahad et al. |
| 5,903,342 A | 5/1999 | Yatsugake et al. |
| 5,963,314 A | 10/1999 | Worster et al. |
| 6,034,776 A | 3/2000 | Germer et al. |
| 6,069,690 A | 5/2000 | Xu et al. |
| 6,081,325 A | 6/2000 | Leslie et al. |
| 6,118,364 A * | 9/2000 | Hashimoto et al. ......... 336/192 |
| 6,122,046 A | 9/2000 | Almogy et al. |
| 6,169,601 B1 * | 1/2001 | Eremin et al. ........... 356/239.8 |
| 6,215,551 B1 | 4/2001 | Nikoonahad et al. |
| 6,271,916 B1 | 8/2001 | Marxer et al. |
| 6,292,259 B1 | 9/2001 | Fossey et al. |
| 6,324,298 B1 | 11/2001 | O'Dell et al. |
| 6,509,965 B1 | 1/2003 | Fossey et al. |
| 6,538,730 B1 | 3/2003 | Vaez-Iravani |

OTHER PUBLICATIONS

U.S. Appl. No. 10/977,144, filed Oct. 28, 2004, James J. Xu.
Sanford et al., "UV Laser Revolutionize Raman Spectroscopy." Laser Focus World, pp. 99-109. Jul. 1997.

* cited by examiner

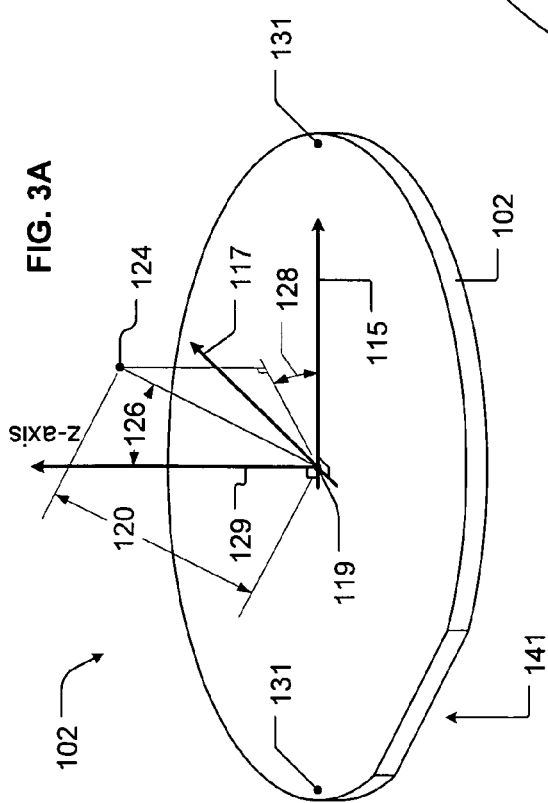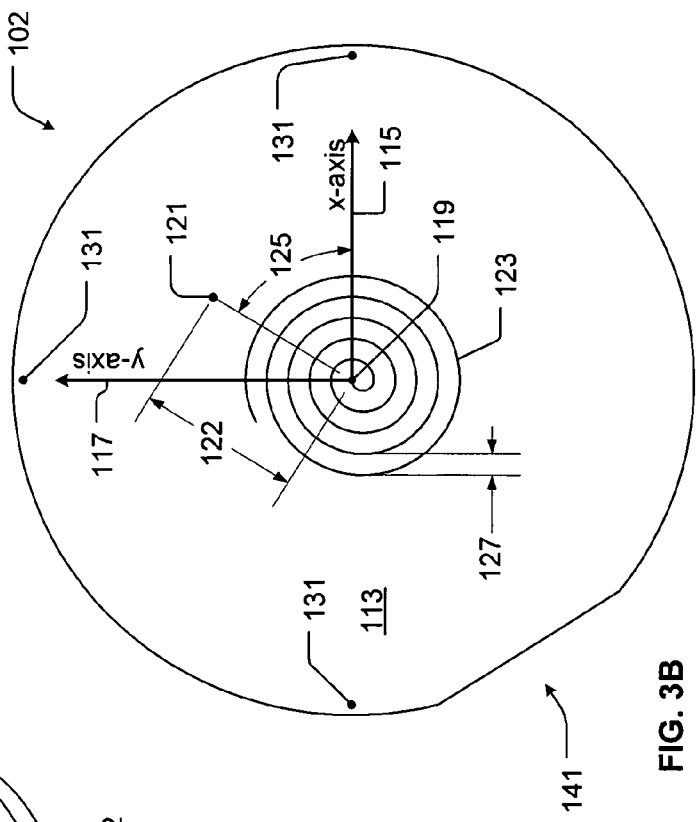

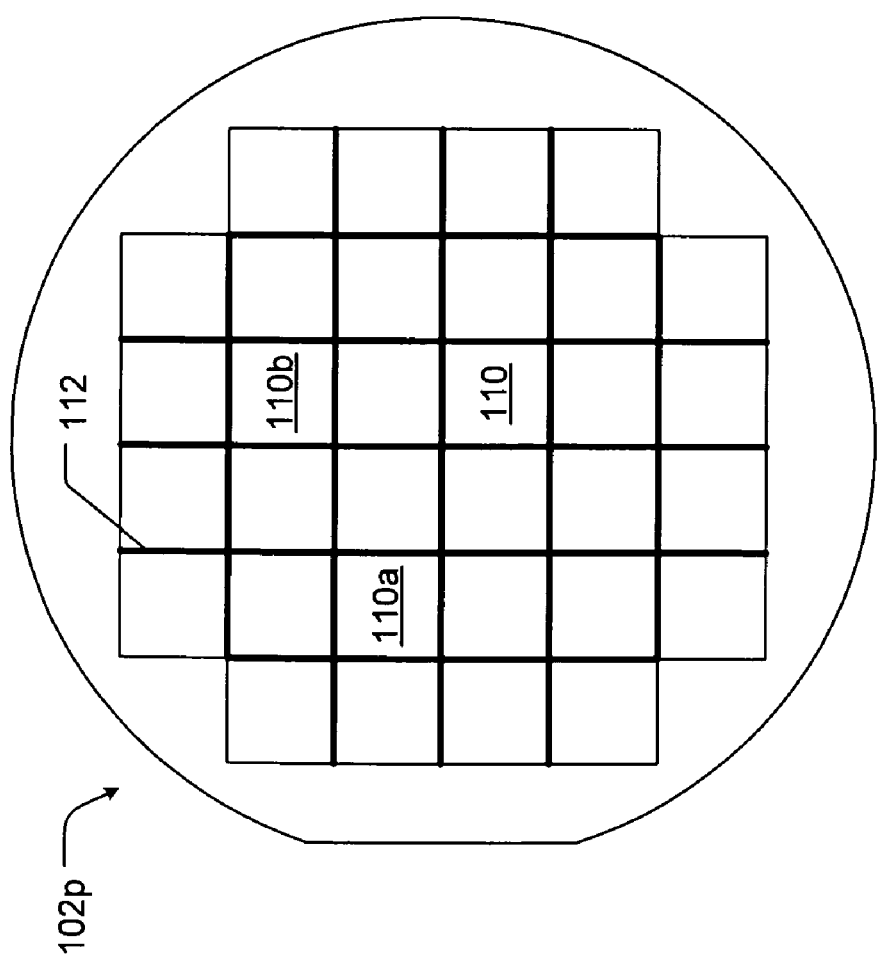

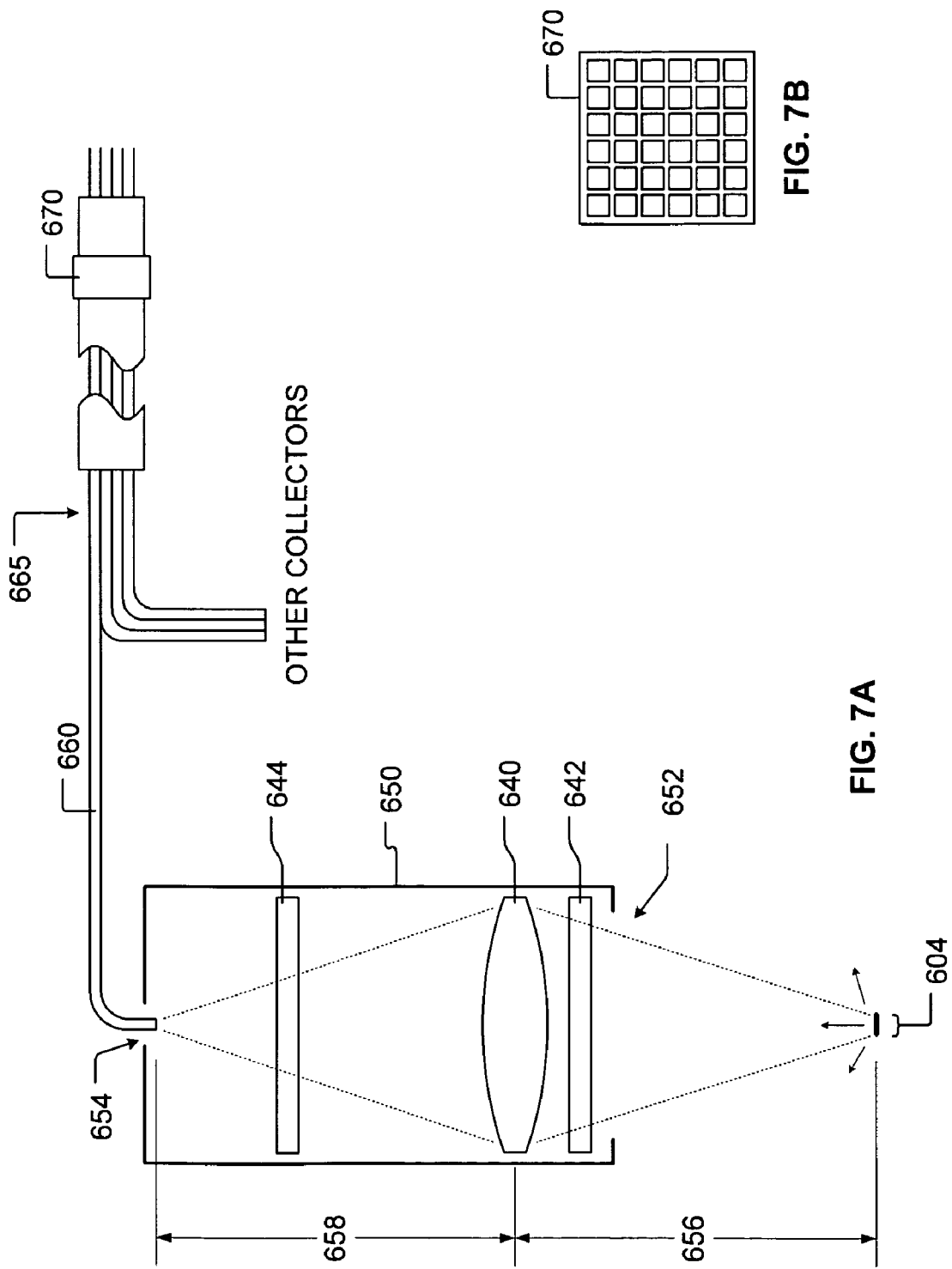

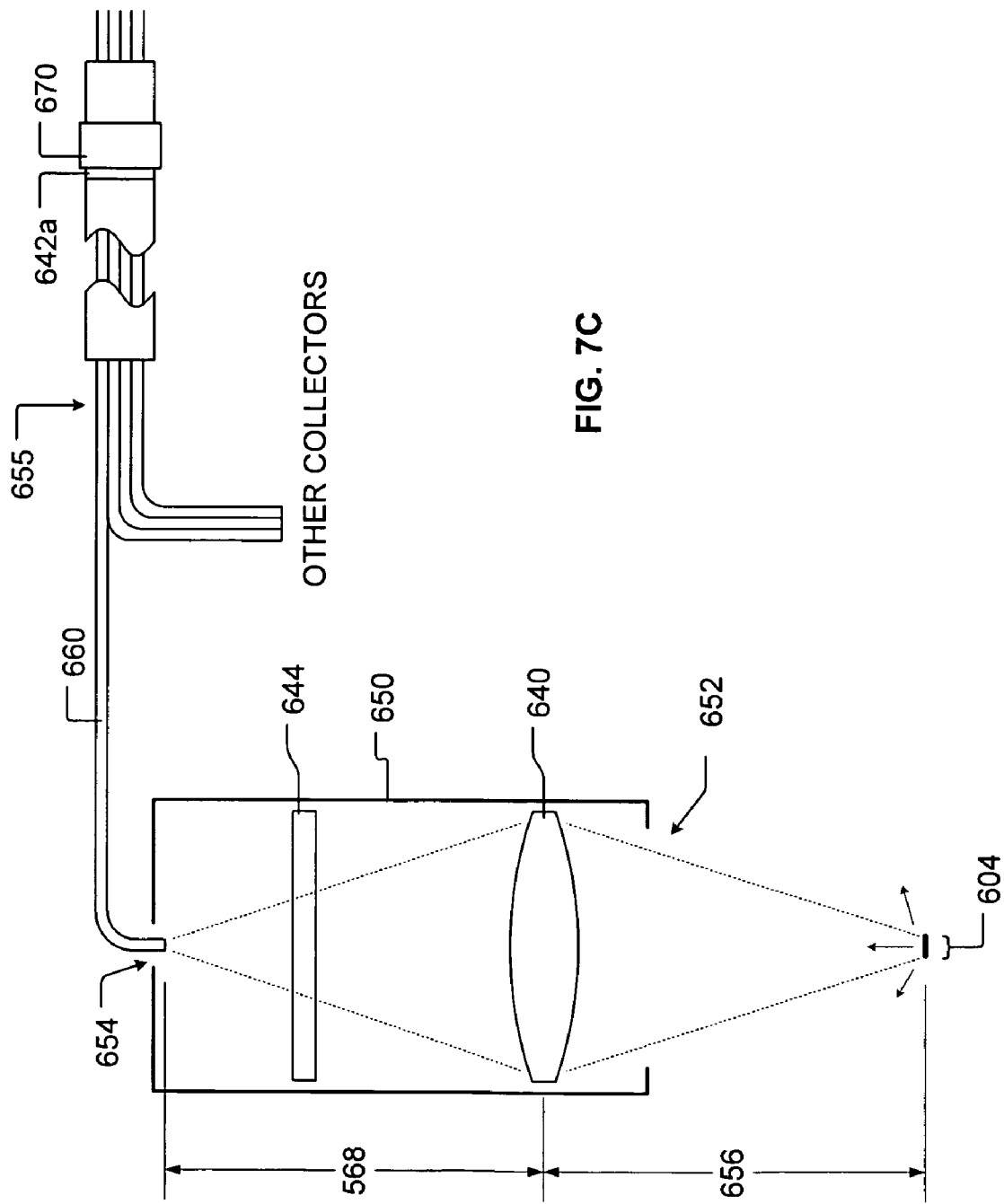

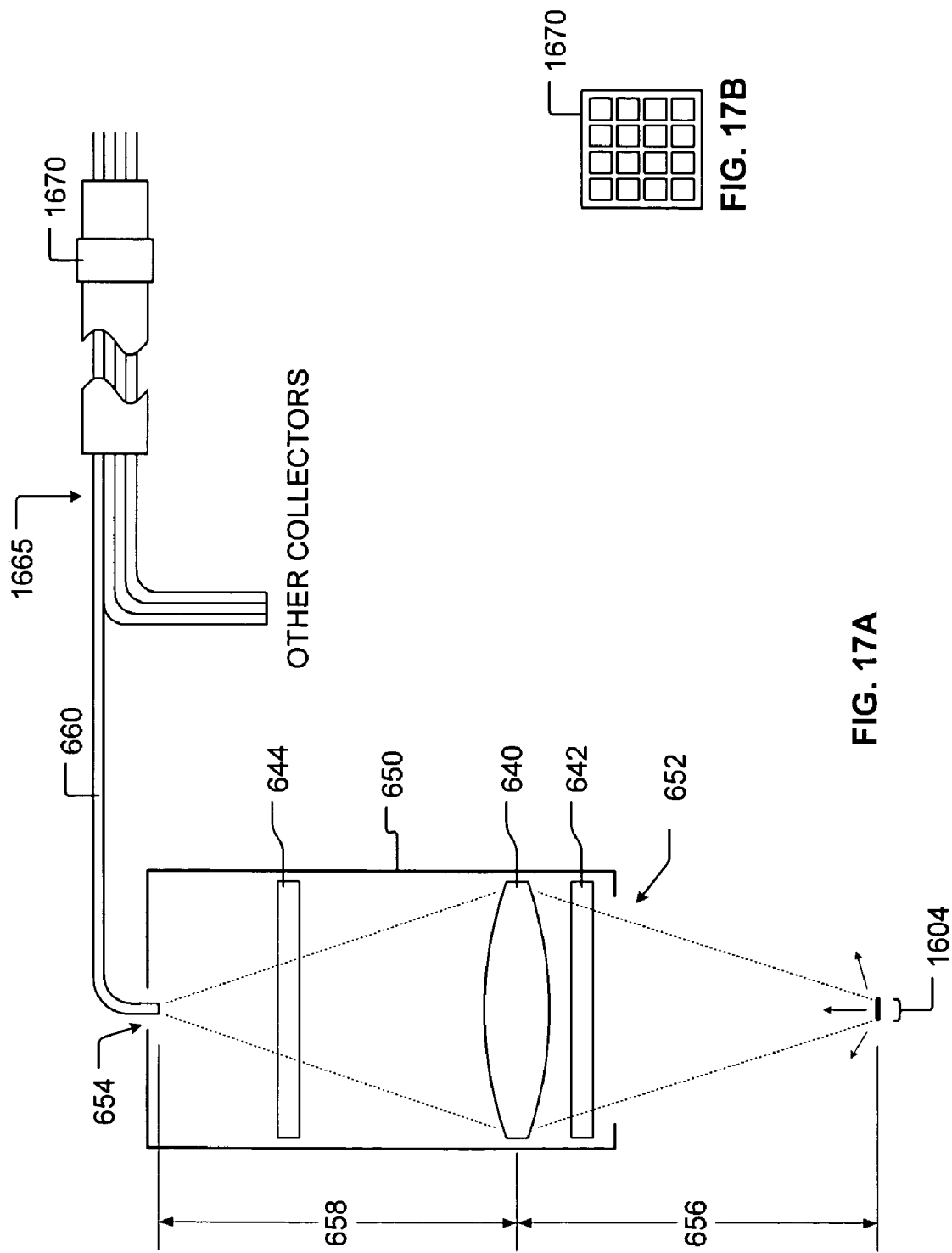

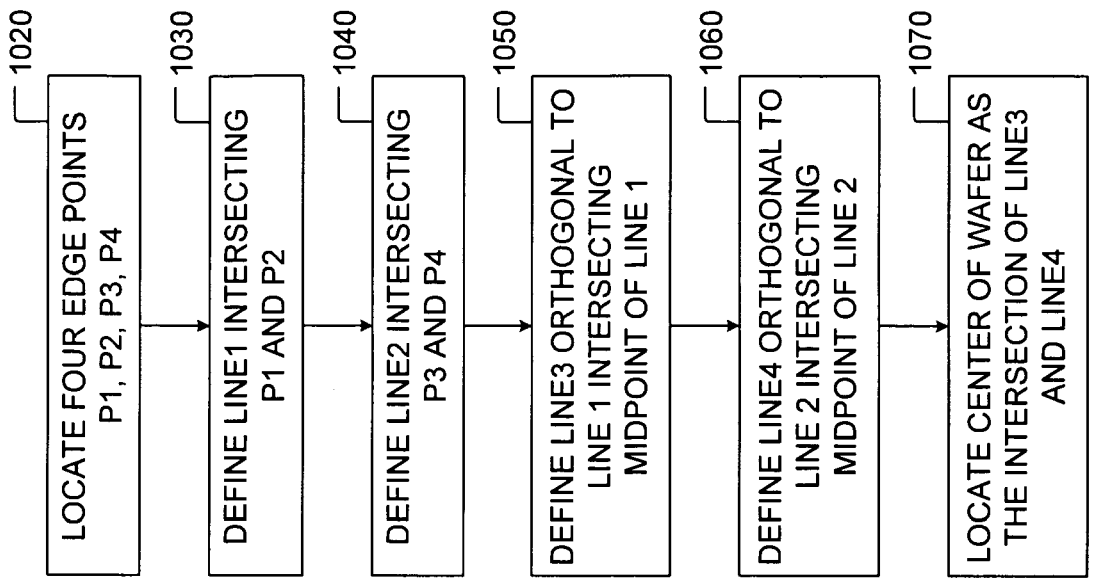
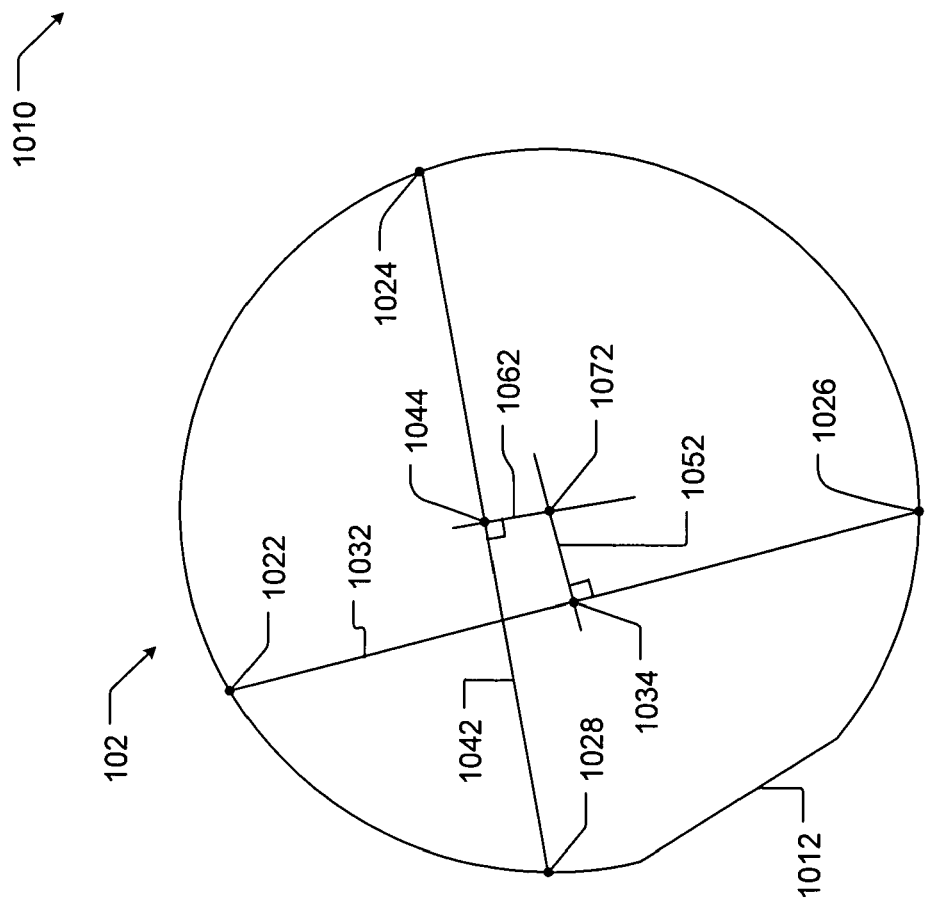

SURFACE INSPECTION SYSTEM

PRIORITY

This application claims the benefit of U.S. Provisional Patent Application No. 60/515,462 filed Oct. 29, 2003 entitled "Defect detection system optimized for both patterned and unpatterned wafer inspection."

BACKGROUND

The present invention generally relates to surface inspection and review systems and methods. In particular, the present invention relates to improved system and method for detecting and analyzing anomalies on surfaces such as surfaces of silicon wafers.

Surface inspection systems are widely used in the semiconductor manufacturing industry to inspect the surfaces of various material wafers to monitor and detect defects. These systems are typically based on an imaging method, a light scattering method, or a combination of both.

In the imaging method, the surface of a wafer under test is imaged (using an image sensor array) and the image analyzed. In general, imaging based inspection systems have higher sensitivity in inspecting patterned wafers compared to sensitivity of light scattering method based systems for patterned wafers.

In the light scattering method, light is introduced to the surface of a wafer under test and scattered light is captured and analyzed. In general, light scattering based inspection systems have higher sensitivity in inspecting unpatterned wafers compared to sensitivity of imaging method systems for unpatterned wafers.

Conventionally, imaging based systems have lower throughput than that of the light scattering based systems, and therefore are used to inspect wafers only on a sampling basis. Accordingly, it takes a relatively long time to image the entire wafer surface. It would be preferable to inspect all patterned wafers rather than inspecting merely a sampling of the wafers.

To increase the throughput of the inspection systems for inspecting patterned wafer surfaces, several approaches were proposed and implemented. In particular, efforts have been made to develop a light scattering based system that is optimized for both patterned and unpatterned wafer inspection.

However, each of these prior art systems presents its own set of shortcomings. For example, many prior art systems lack the polar and azimuthal angular resolution of the scattered signal. Without the angular resolution of the scattered signals, not only is it difficult to identify defects, but also difficult to categorize or classify defects if and when identified. Other prior art systems include many optical elements in complex configurations that lead to attenuation of collected scattering signals. With attenuated signals, it is difficult to identify defects. Yet other prior art systems use ellipsoidal mirrors to collect scattering light and to direct them to fibers or detectors. Such systems are overly sensitive to misalignments, present alignment and focusing challenges, and provides distorted scatter signal angular information due to the ellipsoidal mirrors.

Accordingly, there remains a need for a system and method that alleviates or overcomes these shortcomings.

SUMMARY

The need is met by the present invention. In a first embodiment of the present invention, an inspection system includes a stage, a light source and three rings of collectors. The stage to supports an article for inspection, the article having a surface. The light source provides light impinging on and scattering from an illumination area of the surface. A first ring of collectors collects the scattered light. The first ring of collectors is a set of collectors positioned at a first ring polar angle. A second ring of collectors collects the scattered light. The second ring of collectors is a set of collectors positioned at a second ring polar angle. A third ring of collectors collects the scattered light. The third ring of collectors is a set of collectors positioned at a third ring polar angle. The inspection system includes a plurality of channels with each collector of the three rings associated with a channel. The inspection system includes a processor, connected to the channels, adapted to process information from the channels.

In a second embodiment of the present invention, an inspection system includes a stage, a light source, and a light collection subsystem including a plurality of collectors. The stage supports an article for inspection, the article having a surface. The light source provides light impinging on and scattering from an illumination area of the surface. The light collection system includes a plurality of collectors arranged generally in a semi-spherical layout such that each collector collects at least a portion of the scattering light at a collection polar angle and a collection azimuthal angle that are unique relative to collection polar angle and collection azimuthal angle of other collectors. The inspection system includes a plurality of channels where each collector of the light collection subsystem is associated with a channel. The inspection system includes a processor connected to the channels. The processor is adapted to process information from the channels.

In a third embodiment of the present invention, an inspection system includes a stage, an edge imaging system, and a processor. The stage is operable to support and move an article for inspection, the article having a surface, the surface defining an edge. The edge imaging subsystem is operable to image a portion of the surface of the article, the portion proximal to the edge of the article. The processor is connected to the edge imaging subsystem, the processor being operable to process the image to determine location of the edge of the article.

Other aspects and advantages of the present invention will become apparent from the following detailed description, taken in conjunction with the accompanying drawings, illustrating by way of example the principles of the invention.

BRIEF DESCRIPTION OF THE DRAWINGS

FIG. 3A is a simplified perspective view of an article under inspection;

FIG. 3B is a simplified top view of the top surface of the article of FIG. 3A;

FIG. 3C is a simplified top view of the top surface of another article under inspection;

FIG. 7A is a diagram illustrating another portion of the inspection system of FIG. 1;

FIG. 7B is a more detailed view of another portion of the inspection system of FIGS. 1 and 7A;

FIG. 7C is a diagram illustrating alternative embodiment of the portions of the inspection system of FIG. 1 as illustrated in FIG. 7A;

FIGS. 17A is a diagram illustrating another of the defect review system of FIG. 13;

FIG. 17B is more detailed view of a portion of the defect review system of FIGS. 13 and 17A;

FIG. 18A is a flowchart illustrating a method according to a fourth embodiment of the present invention; and FIG. 18B illustrates the method illustrated in 18A as applied to an article under defect review.

DETAILED DESCRIPTION

Figure 1:
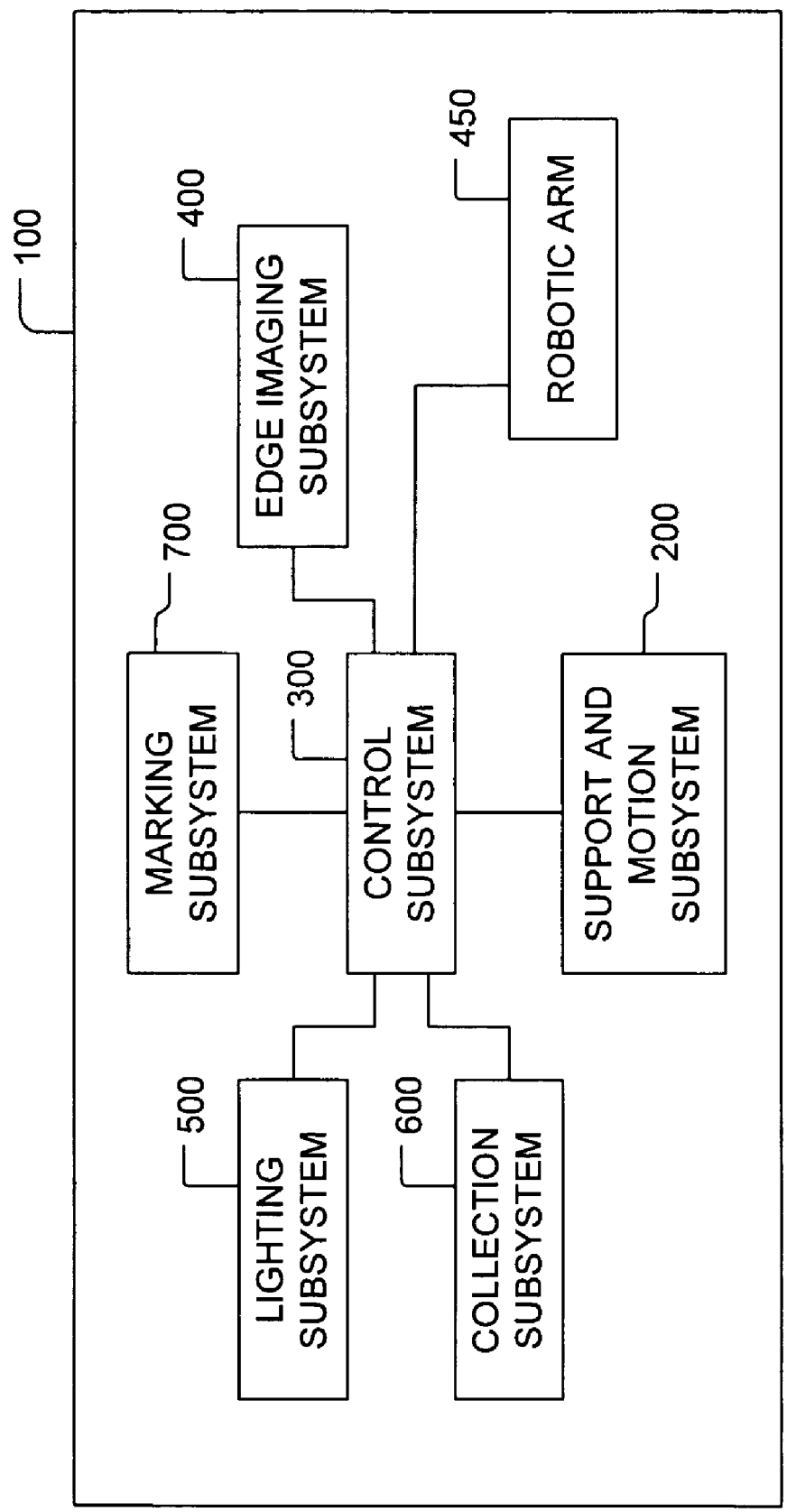
FIG. 1 is a block diagram illustrating an inspection system in accordance with a first embodiment of the present invention.

Outline of the Detailed Description:
I. Introduction
II. Invention Summary and Advantages
III. Inspection System 100 and Method 800
  A. Overview
  B. Support and Motion Subsystem 200
    1. Coordinate Systems
  C. Edge Imaging Subsystem 400
  D. Control Subsystem 300
  E. Lighting Subsystem 500
  F. Collection Subsystem 500
    1. First Ring
    2. Second Ring
    3. Third Ring
    4. Collectors and Channel
  G. Inspection Method—Unpatterned Wafer 810
    1. First Pass
    2. Second Pass
  H. Marking Subsystem 700—Defect Marking
  I. Marking Subsystem 700—Imaging
  J. Marking Subsystem 700—Coordinate System Marking
  K. Inspection Method—Patterned Wafer 820
    1. Patterned Wafer Spiral and Raster Scan
    2. Patterned Wafer Raster Scan
  L. Sample Scatter Signal Calculations
VI. Defect Review System 1000 and Method 1800
  A. Overview
  B. Support and Motion Subsystem 200
  C. Control Subsystem 1300
  D. Lighting Subsystem 1500
  E. Dark-field Subsystem 1400
  F. Collection Subsystem 1500
  G. Bright-field Subsystem 1500
  H. Marking Subsystem 1700—Marking
  I. Marking Subsystem 1700—Imaging
  J. Review Method 1800

I. Introduction

The present invention will now be described with reference to the Figures which illustrate various embodiments of the present invention. In the Figures, some sizes of structures or portions may be exaggerated relative to sizes of other structures or portions for illustrative purposes and, thus, are provided to illustrate the general structures of the present invention. Furthermore, various aspects of the present invention are described with reference to a structure or a portion positioned relative to others structures or portions. Such relative terms and phrases such as, for example, "on" or "above" are used herein to describe one structure's or portion's relationship to another structure or portion as illustrated in the Figures. It will be understood that such relative terms and phrases are intended to encompass different orientations of the device in addition to the orientation depicted in the Figures. For example, if the device in the Figures is turned over, rotated, or both, the structure or the portion described as "on" or "above" other structures or portions would now be oriented "below," "under," "left of," "right of," "in front of," or "behind" the other structures or portions.

II. Invention Summary and Advantages

As shown in the Figures for the purposes of illustration, embodiments of the present invention are exemplified by an inspection system includes a stage, a light source, and a light collection subsystem including a plurality of collectors. The stage supports an article for inspection, the article having a surface. The light source provides light impinging on and scattering from an illumination area of the surface. The light collection system includes a plurality of collectors arranged generally in a semi-spherical layout such that each collector collects at least a portion of the scattering light at a collection polar angle and a collection azimuthal angle that are unique relative to collection polar angle and collection azimuthal angle of other collectors. The inspection system includes a plurality of channels where each collector of the light collection subsystem is associated with a channel. The inspection system includes a processor connected to the channels. The processor is adapted to process information from the channels.

The plurality of the collectors of the present invention allows for collection of scattered light from various polar and azimuthal angles with a relatively high degree of angular resolution compared to the prior art systems. Accordingly, it is easier to identify defects and to even classify the identified defects. Further, each channel (associated with a single collector) provides scatter signal from a particular polar angle and a particular azimuthal angle. Thus, to identify or classify defects, scatter signals gather from only the desirable polar angle and azimuthal angle positions can be analyzed. This allows for even better distinction of and classification of defects found on the surface.

In addition, the inspection system of the present invention does not present ellipsoidal mirrors or other complex optics to gather scattered light or analysis. For this reason, unlike the prior art systems, the inspection system of the present invention minimizes or eliminates attenuation of the scattered light or the loss of signal strength of the scattered light to various insertion losses. Moreover, without mirrors or complex optical configurations, the inspection system of the present invention is relatively less sensitive to focal or alignment errors. For these reasons, again, the inspection system of the present invention provides for even better distinction of and classification of defects found on the surface.

III. Inspection System 100 and Method 800

A. Overview

FIG. 1 is a block diagram illustrating an inspection system 100 in accordance with one embodiment of the present invention including major components of the inspection system 100. The present invention includes the inspection system 100 for examining, analyzing, and marking a major surface of an article of manufacture such as a silicon wafer. The inspection system 100 includes many components and is, for the purposes of discussion herein, described as having subsystems illustrated in FIG. 1; however, it is understood that the discussion of the inspection system 100 in terms of the subsystems and the illustrations and discussions of various components of the inspection system 100 as a part of one of the illustrated subsystems is not intended to limit the structure of the inspection system 100 to the illustrated embodiment.

Referring to FIG. 1, the inspection system 100 includes a support and motion subsystem 200 adapted to support the wafer for inspection. Further, the support and motion subsystem 200 is adapted to move (rotate and laterally move) the wafer to allow the entire surface of the wafer to be inspected. The support and motion subsystem 200 is connected to a control subsystem 300 that includes a processor operable to control the movements of the support and motion subsystem 200.

To place the wafer onto the support and motion subsystem 200, a robotic arm 450 picks up the wafer from another device (not illustrated, and not a part of this present invention) and moves the wafer over the support and motion subsystem 200. For patterned wafer, the robotic arm first moves the patterned wafer to a predetermined intermediate position, so that the center of the patterned wafer is under the edge imaging subsystem 400. The control subsystem is configured to control the edge imaging subsystem 400 and to analyze the images from the edge imaging subsystem 400. From the analysis of these images, the control subsystem 300 commands the necessary corrective moves of the support and motion subsystem 200 so that after the robotic arm moves the patterned wafer to the nominal loading position, and the wafer is released from the robotic arm, the center of the patterned wafer is aligned with the center of the support and motion subsystem 200.

Once the wafer is placed on the support and motion subsystem 200, the inspection system 100 inspects the surface by providing incident light onto a portion of the surface, and collecting the scattered light, and then analyzing the collected light. The incident light is provided by the lighting subsystem 500. The scattered light is collected by a collection subsystem 600. The collection subsystem 600 also converts the collected scattered light into electrical signal. The control subsystem 300 is connected to the lighting subsystem 500 and the collection subsystem 600. The control subsystem 300 is operable to control the lighting subsystem 500 and to analyze the electrical signal to determine defective condition of the portion of the surface under inspection. If a defect is detected in the portion of the surface under inspection, the defect location is recorded, and the defect can be marked, if desired, using a marking subsystem 700, also connected to the control subsystem 300. In this document, the term "light" is intended to encompass visible light as well as to encompass radiation outside or beyond the visible light spectrum.

B. Support and Motion Subsystem 200

Figure 2:
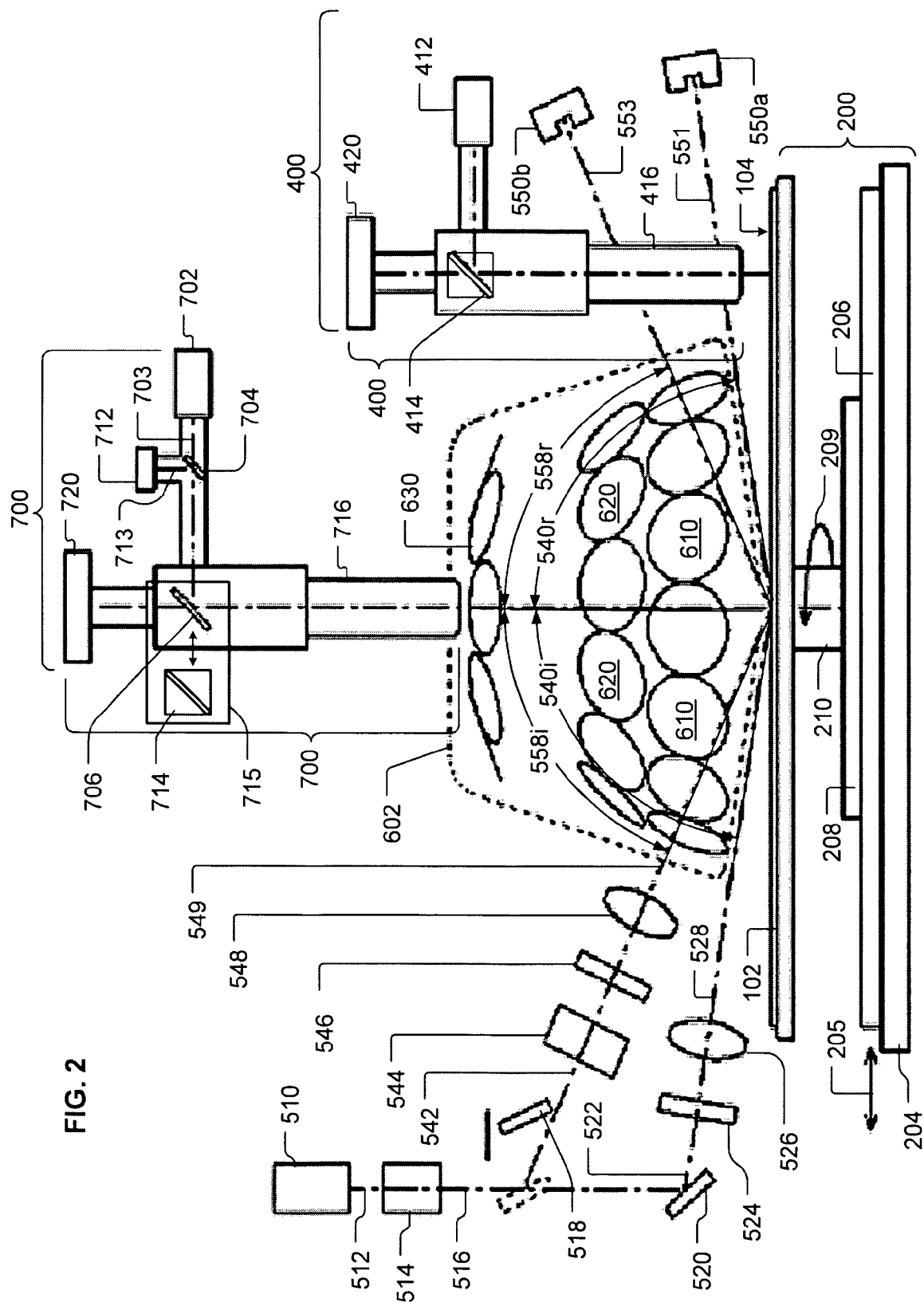
FIG. 2 is a more detailed view of portions of the inspection system of FIG. 1.

FIG. 2 illustrates portions of the inspection system 100 of FIG. 1 in more detail. The inspection system 100 includes the support and motion subsystem 200 adapted to support an article 102 for inspection such as a silicon wafer, the wafer 102 having a major surface 104 for inspection. The support and motion subsystem 200 is also referred to as a stage 200. The stage 200 is operable to rotate the article 102 about a center of rotation and to move the article 102 laterally in both x and y axes and vertically in z axis. The article 102, such as a silicon wafer 102, has a surface 104 defining a plane, surface plane. Both the surface 104 and the surface plane it defines are referred to herein using the same reference numeral 104. The surface 104 of the wafer 102 is inspected by the inspection system 100. For convenience, an unpatterned wafer is refer to as wafer 102u, a patterned wafer as wafer 102p, and a wafer, in a generic context, as 102.

The stage 200 includes several layers. A first layer 204 is operable to translate the wafer 102 along a first lateral axis of translation (for example, the x-axis illustrated in FIGS. 3A and 3B below). The first layer 204 is also referred to as the x-stage 204 and its movement direction is illustrated by as arrows 205. A second layer 206 is operable to translate the wafer 102 along a second lateral axis of translation (for example, the y-axis illustrated in FIGS. 3A and 3B below). The second layer 206 is also referred to as the y-stage 206. A third layer 208 is operable to translate the wafer 102 along a third axis of translation (for example, the z-axis illustrated in FIGS. 3A and 3B below). The third layer 208 is also referred to as the z-stage 208. A fourth layer (rotation stage) 210 is operable to rotate the wafer 102 about a center of rotation (for example about the origin 119 illustrated in FIGS. 3A and 3B). The rotation of the fourth layer 210 is illustrated by arrow 209. Rotations of the fourth layer 210 can be combined with translation of the x-stage 204 or the y-stage 206 to scan the surface 104 in the spiral pattern 123. Translation of the wafer 102 by the z-state 208 can be used to control focus of the collection subsystem 600 on the wafer 102.

1. Coordinate Systems

FIG. 3A is a perspective view of the wafer 102 illustrating spherical coordinate system used to discuss the present invention. FIG. 3B is a top view of the article 102 illustrating Cartesian coordinate system and polar coordinate system used to discuss the present invention. Referring to FIGS. 3A and 3B, locations on and portions of the surface 104 can be described using Cartesian coordinate system, polar coordinate system, or both. In the Cartesian coordinate system, a location, for example first location 121, on the surface 104 is specified by a coordinate (x, y) where x is distance of the first location 121 from an origin 119 along the x-axis 115 and y is distance of the first location 121 from the origin 119 along the y-axis 117 where the x-axis 115 and the y-axis 117 lie on the surface 104, share the same origin 119, and are orthogonal (that is, perpendicular) to each other. In the polar coordinate system, a location, for example first location 121, is specified by coordinate (r, $\phi$) where radius r 122 is distance of the first location 121 from the origin 119 and the angle $\phi$ 125 specifies rotation about the origin 119 on the surface 104 beginning at a reference line such as the x-axis 115 to the first location 121.

Locations in space above the surface 104 are specified using the spherical coordinate system. For example, second location 124 can be specified using three values (r, $\theta$, $\phi$) where radius r 120 is distance from the origin 119 to the second location 124, polar angle $\theta$ 126 is rotation around the origin 119 beginning at a polar angle reference such as the z-axis 129 and ending at the second location 124, and azimuthal angle $\phi$ 128 is rotation around the origin 119 on the surface plane 104 beginning at a reference line such as the x-axis 115 and ending at the second location 124.

C. Edge Imaging Subsystem 400

Referring FIGS. 2 and 3A through 3B, to initially place the wafer 102 on the stage 200, the wafer 102 is picked up by a robotic arm 450 and is moved (relative to the stage 200) over the stage 200 and released by the robotic arm 450 allowing the wafer 102 to be placed on the stage 200. Since the wafer 102 has a shape that is substantially round, it is desirable to place the wafer 102 such that the center of the wafer 102 and the center of the stage 200 are aligned. For unpatterned wafer, the exact placement of the wafer 102 to the center of stage 200 is less important (compared to the placement of a patterned wafer), as long as the defect detection steps cover the entire wafer surface, including the wafer edge. The scattered signal from the edge can be used to determine the wafer edge, and consequently the wafer center. For patterned wafer, the exact placement of the center pattern of wafer 102 to the center of stage 200 is relative more important (compared to the placement of the unpatterned wafer) for a wafer-to-wafer spiral scan image comparison.

FIG. 3C illustrates a top view of a patterned wafer 102p including a plurality of rectangular dies forming die patterns and also forming an array including major streets. A die or a die pattern on the wafer is designated reference numeral 110, and the major streets 112. In the Figures, to avoid clutter, only one die 110 and one major street 112 are indicated with reference numbers. Reference number 110 is used to indicate a generic die or die pattern 110 on the patterned wafer 102p. To specify a particular die, a letter such as an "a" or a "b" is appended to the generic die reference number 110.

To achieve the desired placement and orientation of a patterned wafer 102p relative to the stage 200, the wafer 102 is examined by an imaging subsystem 400 while the wafer 102 is still being held by the robotic arm 450. As the robotic arm 450 is moving the wafer toward the inspection system's nominal loading position, it first stops at a position such that the center pattern area of the wafer is under the imaging subsystem 400. The imaging subsystem 400 examines this center region of the wafer to determine the precise translational and rough angular deviations from previously established references. The system then moves the x and y stages 204 and 206 to correct for this translational deviation, so that the robot arm 450 can then move the wafer 102p to the nominal loading position and the center pattern of wafer 102p will be at the center of the stage 200. The imaging subsystem 400, as illustrated, is located near the edge of the wafer 102p when the wafer is at the nominal loading position, along the path of the robot arm movement. This allows for imaging of areas of the wafer 102p near the center and also near the edge of the wafer 102p.

To image a portion of the wafer 102 (at and near its edge when the wafer 102 is roughly at the center of the stage 200), a lamp 412 of the imaging subsystem 400 is activated to provide imaging light. A beam splitter cube 414 reflects 50 percent of the imaging light toward the portion of the wafer 102 (at and near its edge) via a first objective 416. The first objective 416 focuses the reflected imaging light at the portions of the wafer 102 (at and near its edge). Some of the focused imaging light is reflected from the portion of the wafer 102 back toward the beam splitter cube 414 via the first objective 416. Half of the light reflected form the portion of the wafer 102 passes through the beam splitter cube 416 and is captured by a first imaging array 420 adapted to capture images of various portions of the surface 104 of the wafer 102. The first imaging array 420 can be, for example, a CCD imaging device or a CMOS imaging device that converts the captured light to electrical signal.

For a patterned wafer 102p, the image ("test image") of the center of the wafer 102p from the first imaging array 420 is examined and a rough wafer orientation offset is determined from the prominent rectangular street features. Using a rough orientation offset, the inspection system 100 determines and retrieves a subset of reference images from a series of previously stored reference images taken around the center pattern area at different orientations, of the same type of wafer currently under test. The subset includes portions of the reference images that approximately correspond to the general area of the test image relative to the wafer 102p. These reference images are taken at known locations.

Comparing the test image with the reference image subset, the inspection system 100 can determine the precise translational offset between reference image subset and test image, and enhance the accuracy of the orientation offset. Using the precise translational offset, the control subsystem 300 (of FIG. 1) determines the amount of lateral movements needed to move the stage 200 so that when the robotic arm moves the wafer to the nominal loading position, the center pattern of the wafer is aligned with the center of stage 200. The wafer 102p is released (by the robotic arm 450) onto the stage 200 after the stage 200 makes the lateral correction. Subsequently, the wafer orientation is corrected by a rotational movement of the stage 200 based on the pre-determined orientation offset.

For an unpatterned wafer 102u, the use of the image subsystem 400 is optional. The image subsystem 400 can be used to determine, with increased precision, the wafer center and orientation by examining the wafer edges, and to locate the positions of wafer notch and wafer flat.

D. Control Subsystem 300

Figure 4:
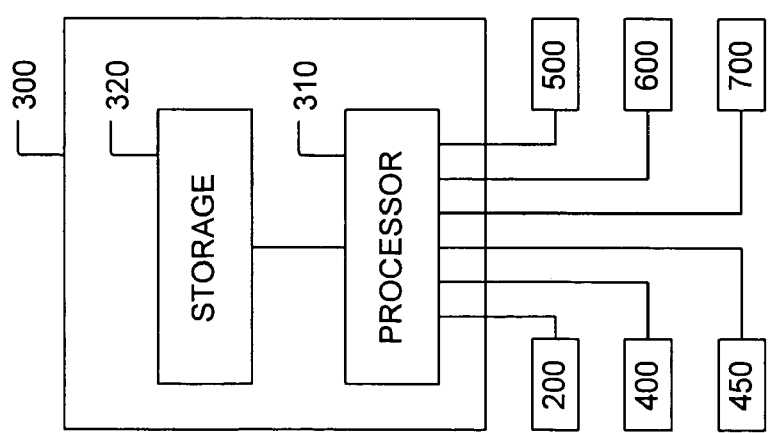
FIG. 4 is a block diagram illustrating a portion of the inspection system of FIG. 1 in more detail.

FIG. 4 illustrates the control subsystem 300 of FIG. 1 in greater detail. As illustrated in FIGS. 1 and 4, the control subsystem 300 is connected to the edge imaging subsystem 400, the lighting subsystem 500, the collection subsystem 600, and the marking subsystem 700 as well as to the robotic arm 450. The control subsystem 300 includes a processor 310 configured or operable to control these subsystems and the robotic arm 450. The control subsystem 300 may include memory 320 or storage 320 adapted to store of instructions for the processor 310, various data that is received, generated, or processed by the processor 310, or both.

E. Lighting Subsystem 500

Referring again to FIG. 2, the inspection system 100 includes an illumination source 510 such as a laser 510 adapted to emit light impinging on and scattering from the surface 104. The light source 510 can be, for example, a continuous wave (CW) laser at 266 nanometer (nm) or a CW laser at 532 nm. It is understood by those skilled in the art that other wavelengths in UV and visible range are also within the scope of this invention. The light source 510 is a source of electromagnetic radiation and may produce electromagnetic radiation ranging in the visible light spectrum or electromagnetic radiation ranging in invisible spectrum. Accordingly, the term "light" includes a wide range of electromagnetic radiation including, for example, various UV sources ranging from 200 nm to about 400 nm which are invisible.

Emitted light 512 from the light source 510 is expanded by a variable beam expander 514 which expands beam size of the emitted light 512 to meet the requirement of the inspection steps as discussed below. For example, the beam expander 514 expands the emitted light 512 to uniformly fill the aperture of a 2D beam scanner 544 located downstream. The expanded beam 516 can travel in one of two different paths depending on position of a turning mirror 518. For a first inspection step, the turning mirror 518 is positioned away from the expanded beam of light 516 allowing the expanded light 516 to pass to a first mirror 520. The light is directed, or reflected, by the first mirror 520 such that reflected light 522 impinges on the surface 104 at a first incident angle 540i. The first incident angle 540i is typically a large grazing angle that can be, for example, approximately 78 or approximately 80 degrees with respect to the z-axis 129 which is normal (orthogonal) to the surface plane 104.

Figure 5A:
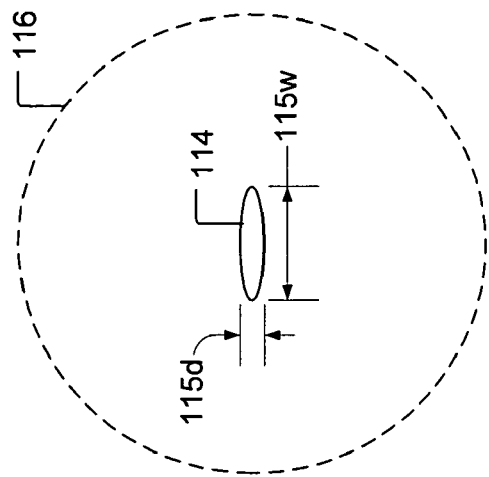
FIGS. 5A and 5B illustrate portions of the surface of the article of FIG. 3A under inspection.

A polarizer 524 filters the reflected light 522 to allow only p-polarized light to reach the surface 104. A focusing lens 526 focuses polarized light to an illumination area on the surface 104. FIG. 5A illustrates a first sample illumination area 114 within a portion 116 of the surface 104. For the first inspection step, a relatively large illumination area size is used. For example, axis lengths 115d (minor axis) and 115w (major axis) of the first illumination area 114 can be in the order of tens of microns, or even more. That is, for relatively coarse resolution inspection of the surface 104, the axis lengths 115d (minor axis) and 115w (major axis) of the first illumination area 114 are approximately 25 microns by 125 microns, respectively.

The axis lengths 115w and 115d of the first illumination area 114 are determined by cross sectional size of the laser light 512, configuration of the beam expander 514, focusing power of the lens 526, and the first incident angle 540i. The first illumination area 114 is typically elliptical in shape. In a second inspection step, discussed below in more detail, a smaller area is illuminated. For example, a second sample illumination area has dimensions of 8 microns by 20 microns, and is used to identify defects with greater resolution (higher accuracy). Illuminated area is often referred to as a "spot" or "laser spot," and the dimensions or the size of the illumination area is often referred to as a "spot size."

Referring to FIGS. 2 and 5A, focused light 528 impinges on the first spot 114. A portion 551 of the focused light 528 is reflected from the first spot 114 and other portions are scattered by defects, particles, and patterns of the first spot 114. The reflected portion 551 is directed at an angle of reflection 540r that has the same angular value as the first incident angle 540i. The reflected portion 551 in this direction is captured by a first beam dump 550a. The first beam dump 550a is electrically connected to a photo detector (specula beam detector) to convert the captured light to electrical signal. The converted electrical signal can be used to analyze and correct intensity fluctuations of the emitted light 512 from the light source 510. For example, a ratio of the intensity of the scattering light to the intensity of the light captured by the beam dump 550a can be used to normalize the scattering light intensity value. That is, the intensity of the scattering light can be divided by the intensity of the light received by the beam dump 550a to generate a ratio. The ratio is basically a normalized quantity unaffected by light source fluctuations.

Some of the impinging focused light 528 scatters and reflects off of defects, imperfections, particles, and patterns and is scattered. The scattered light is captured by collectors enclosed within a collection enclosure 602. The collection enclosure 602 encloses a plurality of collectors arranged in three rings of collectors as well as to prevent ambient light from reaching the collectors. The collection enclosure 602 defines a bottom opening toward the surface 104 of the wafer 102 and a smaller top opening to allow a portion of the marking subsystem 700 to enter the enclosure 602.

During the second inspection step, the turning mirror 518 is moved into the path of the expanded light 516 to deflect the expanded light 516 and direct the expanded light 516 toward the surface 104 at a second incident angle 558i. The second incident angle 558i is smaller than the first incident angle 540i and can be, for example, range from 60 degrees to 80 degrees, and can be, for example, approximately 65 degrees with respect to the z-axis 129 which is normal (orthogonal) to the surface plane 104.

Figure 5B:
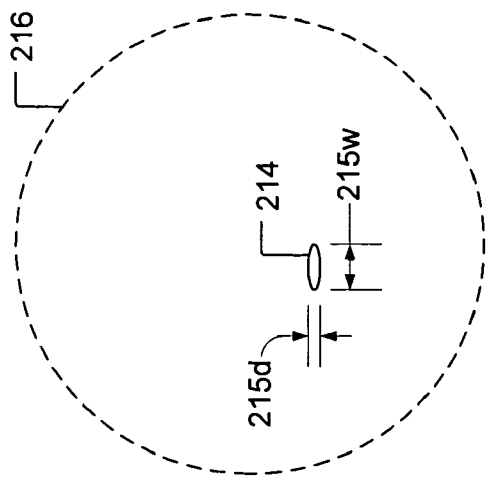

Deflected light 542 is redirected by the 2D scanner 544 to form a rectangular raster pattern on the surface 104. A polarizer 546 filters redirected light to allow only p-polarized light to reach the surface 104. A scan lens 548 focuses the polarized light to a second sample spot 214 on the surface 104. Focused light 549 impinges on the second spot 214. FIG. 5B illustrates the second sample spot 214 within another portion 216 of the surface 104. Referring to FIGS. 2 and 5B, for the second inspection step, a relatively small spot size is used. For example, axis lengths 215d (minor axis) and 215w (major axis) of the second spot 214 can be in the order of microns or tens of microns. That is, for relatively fine resolution inspection of the surface 104, the axis lengths 215d and 215w of the second spot 214 are approximately 8 microns by 20 microns, respectively. The axis lengths 215w and 215d of the second spot 214 are determined by cross sectional size of the laser light 512, configuration of the beam expander 514, $properties of the scan lens 548, and the second incident angle 558i. The scan lens 548 is configured to generate the spot 214 to provide minimal distortion of the rectangular scan area.

The second spot 214 is generally elliptical in shape. The 2D scanner 556 can be Acousto-Optic (AO) or a mechanical scanner. The 2D scanner 556 forms a rectangular scan pattern so that a defect falling within the scanned area can be accurately located. The 2D scanner pattern is further discussed below.

A portion 553 of the focused light 549 is reflected from the second spot 214 and other portions are scattered by defects, particles, and patterns of the second spot 214. The reflected portion 553 is directed at an angle of reflection 558*r* that has the same angular value as the first incident angle 558*i*. The reflected portion 553 in this direction is captured by a second beam dump 550*b*. The second beam dump 550*b* is also electrically connected to a photo detector (specula beam detector) to convert the captured light to electrical signal. The converted electrical signal can be used to analyze and correct intensity fluctuations of the emitted light 512 from the light source 510. Again, a ratio of the intensity of the scattering light to the intensity of the light captured by the beam dump 550*b* can be used to normalize the scattering light intensity value. That is, the intensity of the scattering light can be divided by the intensity of the light received by the beam dump 550*b* to generate a ratio. The ratio is basically a normalized quantity unaffected by light source fluctuations.

Again, some of the impinging focused light 549 scatters and reflects off of defects, imperfections, particles, and patterns and is scattered. The scattered light is captured by collectors enclosed within the collection enclosure 602. The collection enclosure 602 encloses a plurality of collectors arranged in three rings of collectors.

F. Collection Subsystem 500

1. First Ring

Figure 6A:
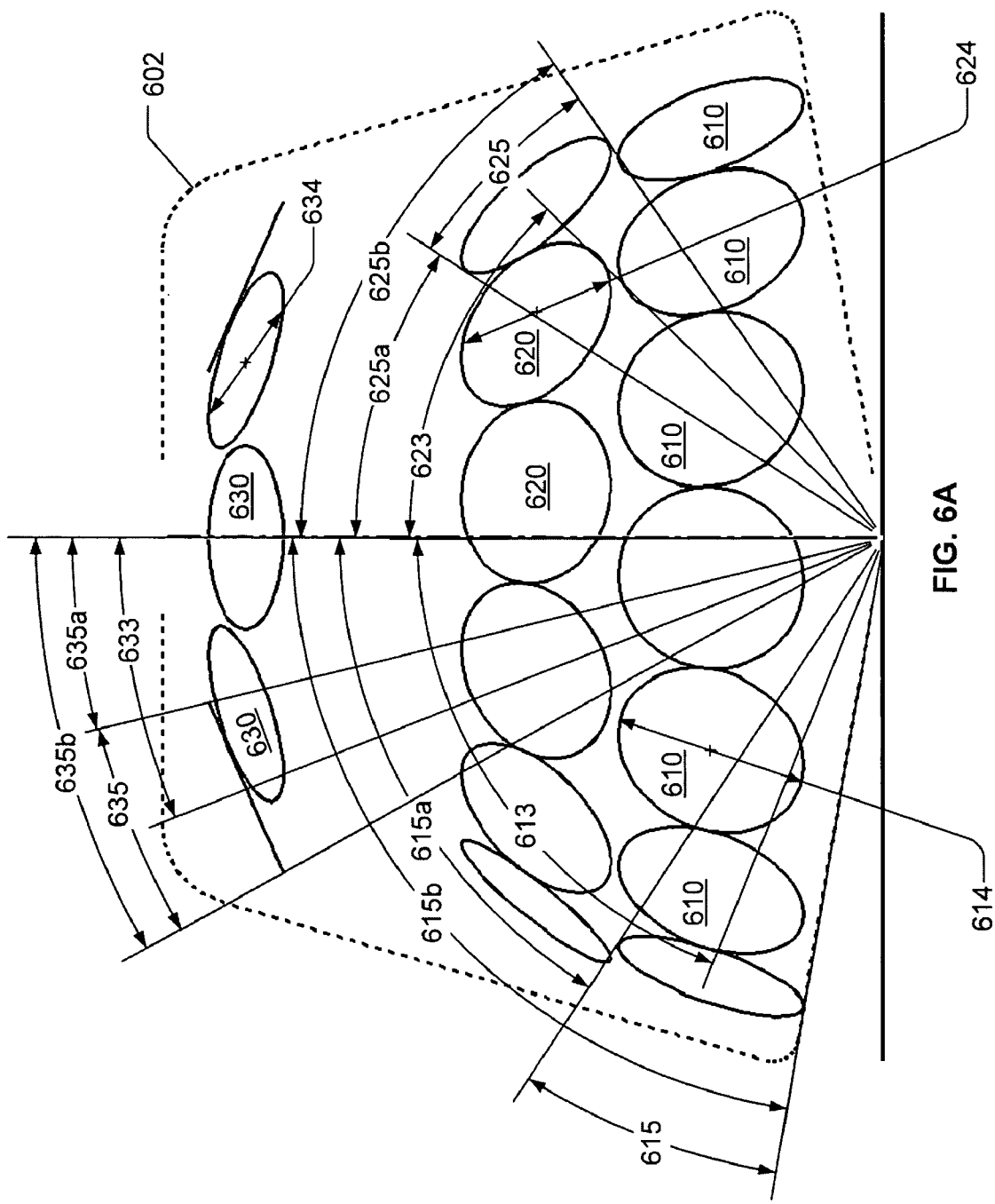
FIGS. 6A is a side view and 6B is a top view of portions of the inspection system of FIGS. 1 and 2 in greater detail.
Figure 6B:
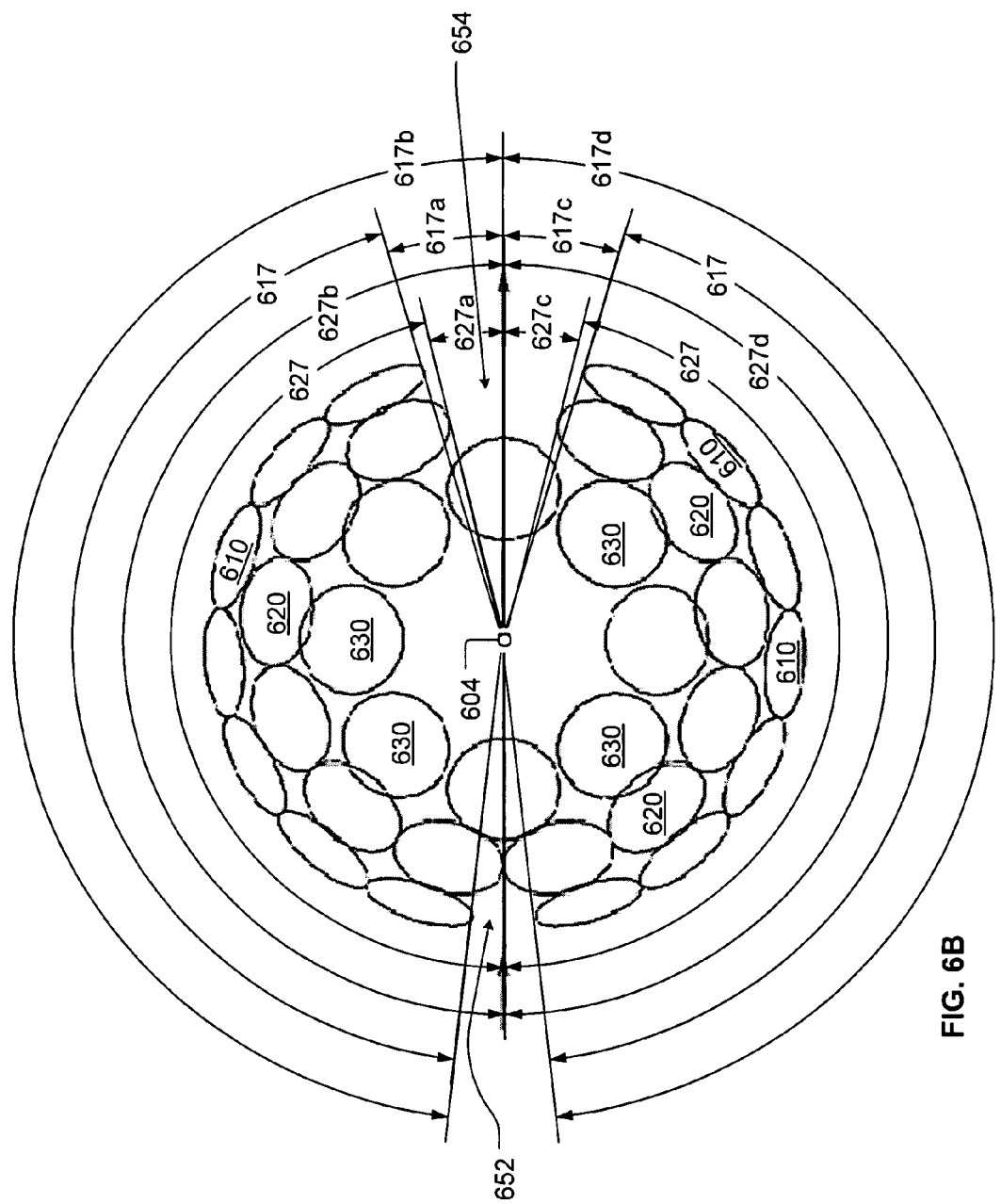

FIG. 6A illustrates a side view of the collectors and FIG. 6B illustrates a top view of the collectors. Referring to FIGS. 6A and 6B, a first set 610 of collectors adapted to collect the scattered light is arranged in a ring having a first polar angle 613. For this reason, the first set 610 of collectors is also referred to as the first ring 610 of collectors. Each individual collector of the first ring 610 of collectors has a first collector diameter 614 and is placed to collect scattering light between a first polar angle range 615. The first polar angle range 615 spans, for example, from approximately 60 degrees to approximately 80 degrees as illustrated by angles 615*a* and 615*b*. The first ring 610 of collectors can include any number of individual collectors. In the illustrated embodiment, the first ring 610 of collectors includes 14 collectors arranged in generally a circular pattern around a field of view 604. To avoid clutter, not all collectors of the first ring 610 of collectors are designated with the reference numeral 610.

The first (lower) ring 610 of collectors is located to collect scattering light within a first azimuthal angle range 617, for example, from approximately 16 degrees to approximately 174 degrees as illustrated by angles 617*a* and 617*b*, respectively as well as from approximately −16 degrees to approximately −174 degrees as illustrated by angles 617*c* and 617*d*, respectively. A first gap 652 allows injection of the focused light 528 and 549 toward the field of view 604. A second gap 654 allows the reflected portion 551 and 553 (illustrated in FIG. 1) of the focused light 528 and 549 (illustrated in FIG. 2) to travel from the field of view 604 to the beam dumps 550*a* and 550*b* (illustrated in FIG. 2) as well as to prevent collection of the reflected portion 551 and 553 (illustrated in FIG. 2) of the focused light 528 and 549 (illustrated in FIG. 2) by the collectors.

2. Second Ring

A second (middle) ring 620 of collectors adapted to collect the scattered light is arranged in a ring having a second polar angle 623. Each individual collector of the second ring 620 of collectors has a second collector diameter 624 and is placed to collect scattering light between a second polar angle range 625. The second polar angle range 625 spans, for example, from approximately 40 degrees to approximately 60 degrees as illustrated by angles 625*a* and 625*b*. The second ring 620 of collectors can include any number of individual collectors. In the illustrated embodiment, the second ring 620 of collectors includes 12 collectors arranged in generally a circular pattern around the field of view 604. To avoid clutter, not all collectors of the second ring 620 of collectors are designated with the reference numeral 620.

The second ring 620 of collectors is located to collect scattering light within a second azimuthal angle range 627, for example, from approximately 14 degrees to approximately 180 degrees as illustrated by angles 627*a* and 627*b*, respectively, as well as from approximately −14 degrees to approximately −180 degrees as illustrated by angles 627*c* and 627*d*, respectively. These angles are relative to x-axis line 115 as illustrated in FIG. 3A.

3. Third Ring

A third (upper) ring 630 of collectors adapted to collect the scattered light is arranged in a ring having a third polar angle 633. Each individual collector of the third ring 630 of collectors has a third collector diameter 634 and is placed to collect scattering light between a third polar angle range 635. The third polar angle range 635 spans, for example, from approximately five degrees to approximately 40 degrees as illustrated by angles 635*a* and 635*b*. The third ring 630 of collectors can include any number of individual collectors.

In the illustrated embodiment, the third ring 630 of collectors includes 8 collectors arranged in generally a circular pattern around the field of view 604. To avoid clutter, not all collectors of the third ring 630 of collectors are designated with the reference numeral 630. The third ring 630 of collectors is located to collect scattering light for the entire 360 degrees of the ring layout.

In the illustrated embodiment, the three rings of collectors combine to form generally a semi-hemispherical-shaped dome over the field of view 604 and collects vast majority of the light scattered from the field of view 604. In alternative embodiments of the present invention, the number of rings, the number of collectors for each ring, or both can vary depending on angular resolution desired from the inspection system. Such variations are within the scope of this invention.

To increase angular resolution of information available by collection of scattering lights, it is understood that the number of collectors each ring, the number of rings, or both may by varied as desired within the scope of this invention.

4. Collectors and Channel

In the illustrated embodiment, each collector of the three rings of collectors is an optical lens having diameters 614, 624, and 634 in the order of tens of millimeters (mm), for example 20 mm. Of course, sizes of these collectors may vary depending on implementation and the desired resolution. Each collector can be coated with antireflective (AR) coating to reduce reflection noise of the inspection system 100 the three rings 610, 710, and 810 of collectors combine as a light collection subsystem.

Each collector lens is focused on and collects light from a field of view (FOV) 604 area on the surface 104 as illustrated in FIG. 7A. Referring to FIGS. 7A and 2, the FOV 604 is located generally on the same plane as the surface plane 104 and is centrally located relative to the three rings 610, 620, and 630 of collectors. The FOV 604 is generally circular in shape. The size of the FOV 604 is a function of lens property within each ring of collectors as well as the polar angle of the rings. In the illustrated embodiment, the FOV 604 is approximately 0.7 mm in diameter. The FOV 604 is larger than the spots 114 and 214 (illustrated in FIGS. 5A and 5B). Initially, when the article 102 such as a wafer 102 is placed on the stage 200 (illustrated in FIG. 2), the FOV 604 coincides with the origin 119 which is the center of the wafer 102. As the stage 200 moves relative to the rings of collectors 610, 620, and 630, the FOV 604 is moved across the surface 104 to allow for the scanning and examination of the entire surface 104 of the wafer 102; thus, the FOV 604 is not always coincident with the origin 119 (illustrated in FIGS. 5A and 5B) of the wafer 102.

FIG. 7A illustrates additional portions of the inspection system 100 along with some portions of the inspection system 100 illustrated in FIG. 2. Referring to FIG. 7A, an individual collector lens 640 can be preceded or followed by a band-pass filter 642 and followed by a retractable polarization filter 644 (also, "polarizer" 644). The collector lens 640 represents any one of the collectors from the three rings 610, 620, and 630 of collectors illustrated in FIGS. 2, 6A, and 6B. The band-pass filter 642 is used to block unwanted light to decrease noise, thus increasing signal-to-noise (S/N) ratio in the collected information. For example, when using 266 nm laser as the illumination source 510 (of FIG. 2), the band-pass filter 642 allows 266 nm wavelength light to pass while blocking light having different wavelengths including visible light. This reduces collection of ambient light leaked into the inspection system 100 and other light noise by the collection lens 640. The polarization filter 644 can block s-polarized light (allowing p-polarized light to pass) or block p-polarized light (allowing s-polarized light to pass) depending on the desired implementation from reaching the next stage.

The retractable polarizing filter 644 can be used for selected collector lens to improve S/N ratio for certain application. For example, for inspecting unpatterned wafers for defects, angular information in the polar and azimuthal directions is unique depending on surface texture, polarization state of the light, and defect properties. For inspecting unpatterned wafers (with micro roughness surface texture), the signal-to-noise ratio between defect and micro-roughness improves significantly in some azimuthal directions than in others.

The collection lens 640, the band-pass filter 642, and the polarization filter 644, when used, are enclosed in a light shroud 650 having two openings 652 and 654 with a first opening 652 in the direction toward the field of view (FOV) 604 and a second opening 654 in a direction opposite the first opening 652 and toward a waveguide 660 such as optical fiber 660. The optical fiber 660 has a first end where light enters the optical fiber 660, the first end proximal to the first opening 652 of the light shield, and a second end where the light exits the optical fiber 660, the second end proximal to a photo detector array 670. The collection lens 640 focuses the field of view (FOV) 604 onto the first end of the optical fiber 660. The collection lens 640 has a focal length of ranging from 30 mm to 40 mm. Coupling from the FOV 604 to the first end opening of the optical fiber 660 is a 4-f coupling. That is, distance 656 from the FOV 604 to the collection lens 640 is twice the focal length of the collection lens 640. Further, distance 658 from the collection lens 640 to the opening of the first end of the optical fiber 660 is also twice the focal length of the collection lens 640. That is, magnification between the field of view 604 and the first end of the optical fiber 660 is one-to-one.

The optical fiber 660 is a single mode fiber with 0.22 numerical aperture (N.A.) and approximately 1.0 mm silica core. Length of the optical fiber 660 is approximately 0.5 meters, but this can vary. Transmission efficiency through the optical fiber 660 is above 95 percent for 266 nm deep ultra-violet (DUV) light and even higher for 532 nm light. The collection lens 640 has numerical aperture slightly less than that of the optical fiber 660 and produces a focus spot smaller than the optical fiber 660 core within the entire depth of focus of the collection lens 640. Thus, with the relatively large depth of field of the collector lens 640, coupling between the collection lens 640 and the optical fiber 660 is optimized and little light is lost. Further, the relatively large depth of field (DOF) of the collector lens 640 makes the system less sensitive to slight shifts in focus due to slight z-axis movements of the wafer 102 or due to unevenness of the wafer 102. Such focal shifts have minimal impact on collection of the scattered light. For example, in one embodiment, the lens 640 has a maximum lateral aberration of 0.7 mm and maximum longitudinal aberration of 10 mm. That is, if the focus shifts by 1 mm (which is within the 10 mm longitudinal aberration range), the light spot at the collection fiber will remain at 0.7 mm diameter.

Scattered light (collected by the collector lens 640 and filtered by the band-pass filter 642 and the polarization filter 644) is focused onto and inserted into the optical fiber 660 which carries the collected scattered light. The light carried by the optical fiber 660 is also referred to as optical signal. The optical fiber 660 guides the optical signal to a photo detector.

As illustrated in FIG. 7A, the optical fiber 660 is bundled 665 with other optical fibers each of which is coupled with a collector lens from the three rings 610, 620, and 630 of collectors, and each of which is carrying optical signal collected by the collection lens coupled to it. The bundled optical fiber 665 is coupled to the array 670 of photo detectors. FIG. 7B illustrates a front view of the photo detector array 670. Referring to FIGS. 7A and 7B, the photo detector array 670 can be an array of photo multiplier tubes (PMTS) or an array of photo detector diodes. Each photo multiplier tube (or each photo detector diode) of the array 670 is adapted to convert optical signal from an optical fiber into corresponding electrical signal. Each photo multiplier tube is referred to as a pixel. The electrical signal represents the light scattered from the wafer and collected by the collectors. Thus, each pixel value represents the light scattered from the wafer and collected by the collector corresponding to the pixel. Here, a PMT represents a basic angular resolving light sensing element. In light detection terms, a pixel is the smallest light sensing element. The size and the number of such elements in a detector usually determine the resolution of a system either in space or in angular terms.

In the illustrated embodiment, the photo detector array 670 includes at least 34 PMTS, one PMT for each optical fiber 660, each optical fiber carrying optical signal from one of the collector lenses of the three rings of collectors 610, 620, and 630 illustrated in FIGS. 2, 5A, and 5B. For convenience, an individual collector lens of the inspection system 100 (for example the collector lens 640), optical components associated with it (such as the polarization filter 644 or a band-pass filter 642), and the optical fiber coupled to it (such as the optical fiber 660) is referred to as a "channel." Thus, each collector lens is associated with and is a component of a channel. Further, a channel carries optical signal representing the scattered light that its associated collector lens collects. Consequently, the 34 channel inspection system 100 of the present invention provides 34 pixel resolution of the scattering light signal collected by the collectors. Each of the pixels includes information regarding scattered light for a particular channel associated with a particular collector. Thus, the three rings 610, 620, and 630 of collectors preserve angular information regarding the captured scatter light in both polar and azimuthal angles.

Each collector collects scattered light from a unique range of collection polar angles and collection azimuthal angles relative to the range of collection polar angles and collection azimuthal angles of all other collector of the inspection system 100. This arrangement provides a useful segmentation of angular detection because this arrangement results in no cross talk between the channels of the inspection system 100.

FIG. 7C illustrates an alternative embodiment of the additional portions of the inspection system 100 illustrated in FIG. 7A. In FIG. 7A, one or more collector lens 640 can be preceded or followed by a band-pass filter 642. This configuration allows for the application of a band pass filter 642 for selected collector lenses of the inspection system 100. If a band pass filter 642 is desired for all of the channels of the system 100, then, a single band pass filter 642a can be used to reduce complexity and cost. The single band pass filter 642a is placed between the second end of the optical fiber 660 and the photo detector array 670. The single band pass filter 642a is sufficiently large to filter all of the optical fibers 660 directed toward the photo detection sensor array 670.

In FIG. 7A, only one fiber bundle 665 is illustrated, the fiber bundle 665 including optical fibers of all of the channels. In alternative embodiments, the optical fibers of the channels can be grouped to form multiple bundles, each bundle having optical fibers from a plurality of channels. For example, a lower ring fiber bundle includes optical fibers for the channels associated with the lower ring 610 of collectors. The lower ring fiber bundle includes 14 optical fibers (one for each collector) coupled to a 4×4 PMT detector array. Such a PMT array has 16 detection units or 16 pixels. For the lower ring, two pixels of the 4×4 PMT array is unused.

A middle ring fiber bundle includes optical fibers for the channels associated with the middle ring 620 of collectors. The middle ring fiber bundle includes 12 optical fibers coupled to a 4×4 PMT detector array with four unused pixels in the detector array. An upper ring fiber bundle includes optical fibers for the channels associated with the upper ring 630 of collectors. The upper ring fiber bundle includes eight optical fibers coupled to a 2×2 PMT detector array. Here, there are eight channels for only four pixels, or detectors. Thus, two optical fibers are assigned to each pixels of the PMT detector array. Optical fibers associated with collectors having symmetrical azimuthal angles within the upper ring 630 are combined to a single pixel. In the alternative embodiment, this is acceptable because at the upper ring location, azimuthal angular resolution is relatively less important than the azimuthal angular resolution of the lower ring 610 of collectors or the middle ring 620 of collectors.

In the alternative embodiment, since a 2×2 detector array is used for the upper ring 630 of collectors, then the 34 channel inspection system 100 of the present invention provides 30 pixel resolution of the scattering light signal collected by the collectors.

Figure 7D:
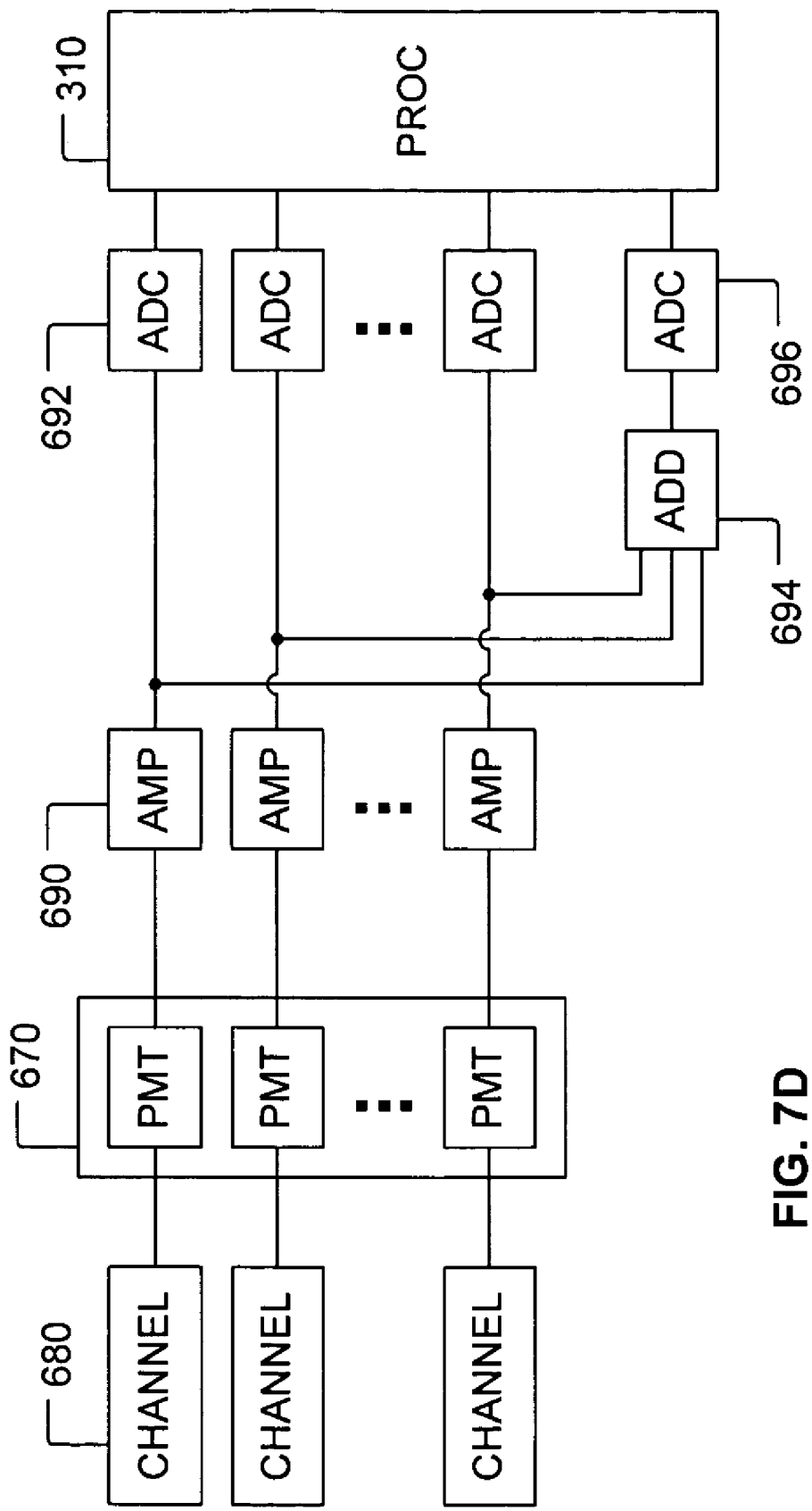
FIG. 7D is a more detailed view of yet another portion of the inspection system of FIG. 1 in block diagram form.

Continuing to refer to FIG. 7A, optical signal from each optical fiber, for example the optical fiber 660, of the optical fiber bundle 665 is converted to electrical signal by at least one PMT of the PMT 670. The electrical signal from each PMT is operated on by electrical circuits as illustrated in FIG. 7D. Referring to FIGS. 7A and 7D, a channel is referred to using reference numeral 680. The electrical signal from each PMT is amplified by an amplifier 690 and converted to digital electrical signal by analog-to-digital converter (ADC) 692. Finally, the digitalized electrical signal is sent to the processor 310. The amplified electrical signal from the amplifiers 690 for each of the PMTS can also be integrated, or summed, by an adding circuit 694, digitized by an ADC 696, and forwarded to the processor 310 for further analysis.

The processor 310 is programmed to analyze the digitalized electrical signal received from the ADC 692, each ADC 692 connected to a channel. Again, each channel carries optical signals collected by one of the collectors of the three rings 610, 620, and 630 of collectors. Each collector collects scattered light from a unique range of polar angles and azimuthal angles relative to all other collector of the inspection system 100. Accordingly, the processor 310 is programmed to recognize defects (such as surface imperfections, undesired particles, or defective patterns) on the surface 104 of the article 102 (illustrated in FIGS. 2, 3A, and 3B).

The signal from each channel can either be summed up or processed separately as shown in FIG. 7D and discussed above. Referring to FIG. 7D, for scatter signal from unpatterned wafer where angular information is less important (than the angular information of scatter signal for patterned wafer), the electrical signal from the photo detector 670 are often summed for further analysis. Here, as illustrated in 7D, the summation is performed (by the adding circuit 694) before the electrical signal is converted to digital signal by an analog-to-digital convert 696. This minimizes electronic noise. For scatter signal from patterned wafer where angular information is relatively more important, electrical signal (from the photo detector 670) from each channel is digitized by the ADC 692 for analysis by the processor 310. For scatter signal from unpatterned wafer with significant microroughness, electrical signal (from the photo detector 670) from selected channels are digitized by the ADC 692 for analysis by the processor 310. Here, the selected channels are those with polarizers, with bypass-filters, or both.

G. Inspection Method—Unpatterned Wafer

Figure 8A:
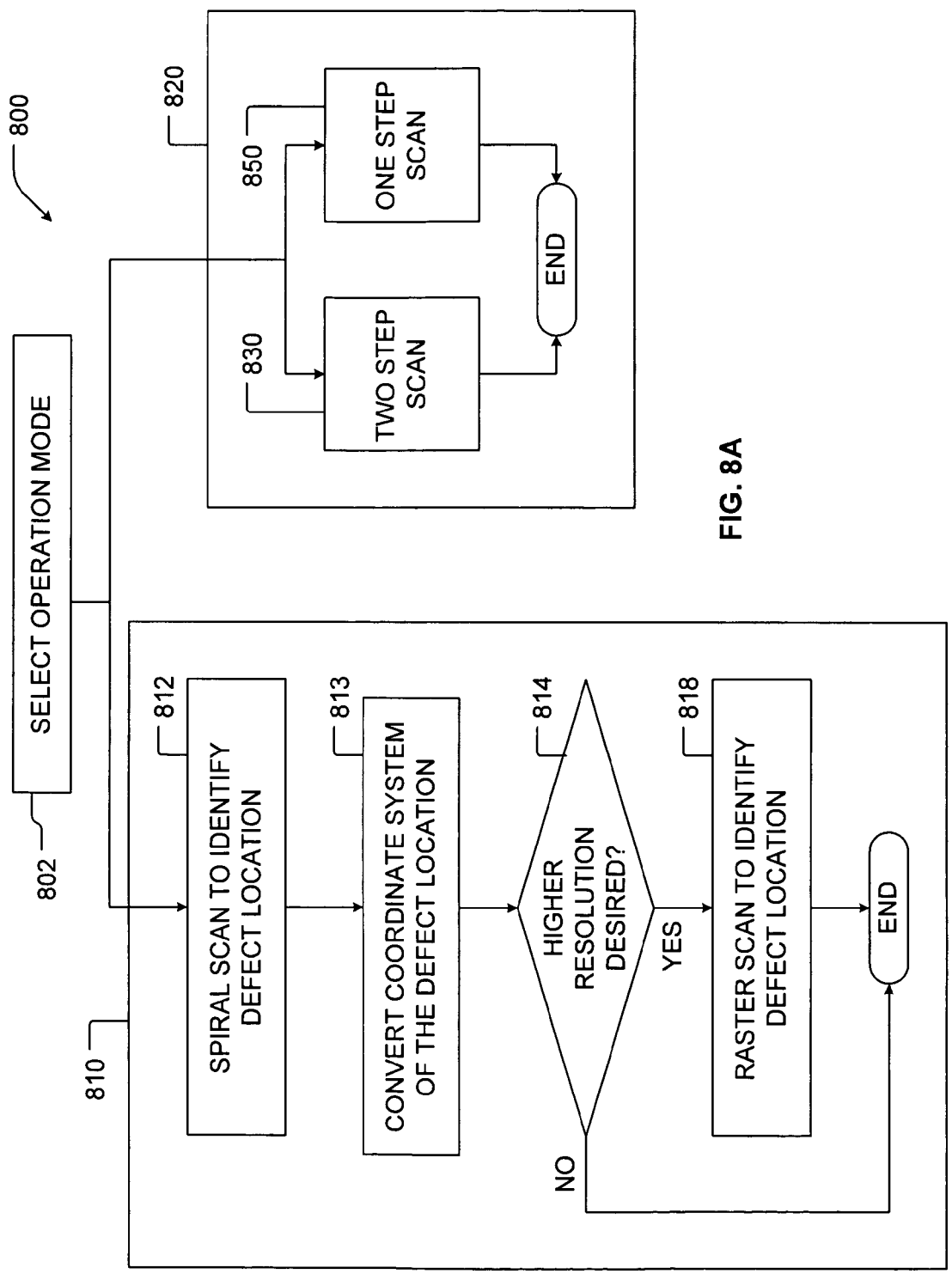
FIGS. 8A and 8B are flowcharts outlining an inspection method according to a second embodiment of the present invention.

FIG. 8A illustrates a flowchart 800 outlining operating modes for inspecting the wafer 102 in accordance with the present invention. Referring to FIGS. 1, 2, 4, and 8A, the flowchart 800 illustrates operation modes and the steps of the operation modes of the present invention. The inspection system 100 of the present invention provides for a first mode of operation 810 and a second mode of operation 820 for inspecting the surface 104 of the wafer 102 and a means for selecting between the first mode 810 of operation and the second mode 820 of operation. The first mode 810 of operation is intended for inspecting unpatterned or bare wafer. The second mode 820 is intended for inspecting patterned wafer. For convenience, the unpatterned wafer is designated 102u and the patterned wafer is designated 102p. Both the unpatterned and patterned wafers 102u and 102p are placed on the inspection system 100 in the similar manner. A switching means can be provided to allow an operator to switch between the first mode 810 and the second mode 820 of operations for inspecting the wafer 102.

In the first mode 810, a first unpatterned wafer inspection step 812 is intended to quickly locate defects on the unpatterned wafer 102u, and a second unpatterned wafer inspection step 818 is intended for providing more accurate defect coordinates on the surface 104 of the wafer 102u.

1. First Pass

Referring to FIGS. 2, 3B, 5A, and 8A, during the first unpatterned inspection step 812, also referred to as the first inspection pass 812, the surface of the wafer 102u is scanned in a spiral pattern 123 to identify defect locations at a first resolution. This is achieved by first activating the illumination source 510. The turning mirror 518 is positioned away from the expanded light 516 allowing the expanded light 516 to be reflected by the first mirror 520 such that reflected light 522 impinges on the surface 104 at a first incident angle 540i. This results in a spot 114 on the surface of the wafer 102 proximal to the center of the stage 200. Then, the stage 200 rotated and moved in one of the lateral directions (x-axis or the y-axis) to effectuate a movement of the spot 114 relative to the surface 104 of the wafer 102u. The spiral pattern 123 scan is intended to quickly locate defects on the smooth surface 104 of the unpatterned wafer 102u.

During the first inspection step 812, the spot 114, in the illustrated embodiment, defines an elliptical area having axis lengths 115d (minor axis) and 115w (major axis) of approximately 25 microns by 125 microns, respectively. This is also referred to as the resolution of the location. Again, the size of the spot 114, also referred to as a spot size 114, can vary in alternative embodiments. Interval 127 of the spiral pattern 123 is related to the size of the spot 114. In the illustrated sample embodiment, the interval 127 of the spiral pattern 123 is approximately 100 microns (the width of 115w, less overlap of approximately 25 microns). The rotation stage 210 can spin at a speed as high as 40 revolutions per second. Typically, the lateral, linear stages 204 and 206 can move at a speed of up to 200 mm per second. Actual radial scan speed is equal to spot size, less overlap multiplied by revolutions per second. For 125 micron spot size at 30 revolutions per second, the radial scan speed is three mm per second. Thus, a 12 inch wafer can be scanned in approximately 50 seconds.

When the focused incident light 528 impinges on the spot 114 of the surface 104, the light is reflected, scattered, or both depending on the condition of the portions of the surface 104 being illuminated. Any scattered light is collected by the collectors of the three rings 610, 620, and 630 and directed to the PMT array 670 as optical signal. The optical signal is converted to electrical signal by the PMT array 670. The electrical signal represents the light scattered from the wafer and collected by the collectors.

The electrical signal is analyzed by the processor 310 to determine whether or not the electrical signal (representing the scattering light) suggests that the illuminated area 114 includes defects. For example, if the electrical signal from a location is greater than a threshold, then the location is designated as a defect location. In the illustrated embodiment, the analysis of the electrical signal is performed concurrently with the spiral scan pass 812. In an alternative embodiment, the electrical signal is stored in the storage 320 during spiral scan pass 812, and the stored information can analyzed later for defect identification.

A defect on the wafer 102u can vary in type, shape, and size. As for type, the defect can be foreign particle or a scratch on the surface 104. As for shape, the defect can have spherical or elongated shape. For example, the defect can be a scratch line. As for size, the defects of interest typically range from 10 nanometers (nm) and larger, and is generally smaller than the spot size of the spot 114. Since the shape and to some extent the composition of a defect affects the directional scattering profile of its scattering, the information provided by the fine resolution of the present invention can help defect identification. For example, a round defect would have a symmetrical angular distribution with respect to the incident plane 104, while a scratch would have a strong directional component.

The inspection system 100 takes advantage of the fine azimuthal resolution by collecting and analyzing azimuthal channel signals separately. The inspection system 100 can have individual thresholds for each azimuthal channel signal. The inspection system 100 can identify a defect using many criteria. For example, if maximum sensitivity of all defects is desired, then the criterion can be that the signal of all azimuthal channels together exceeds a threshold. Alternatively, to detect only scratch defects, the criterion can be that a ratio of the number of strong signal channels and weak signal channels is over a predetermined threshold If the illuminated area 114 includes defects, then the location of the illuminated area 114 is identified as a defect location and the location information is saved in polar coordinates, for example $(r_1, \phi_1)$. The first inspection step 812 is continued until the entire surface 104 of the wafer 102u is examined, and every defect location identified and saved. For example, additional identified defect locations are saved as $(r_2, \phi_2)$, $(r_3, \phi_3)$, and so on until the last defect location $(r_N, \phi_N)$ where N is the total number of defect locations. All defect locations are saved in the memory 320. A set of defect locations is also referred to as a defect location map. The defect locations $(r_i, \phi_i)$ (in polar coordinate notation) are converted to equivalent Cartesian coordinate notation $(x_i, y_i)$ for all i from 1 to N where N is the number of the identified defect locations. Step 813. The coordinate system conversion techniques are known in the art.

For some applications, it is sufficient to determine the total number of defect locations, N. For other applications, it is sufficient to determine the defect locations with the resolution available in the first unpatterned wafer inspection step 812. For these applications, where higher resolution of the defect location is not desired, the first mode of operation 810 is completed for the wafer under inspection. This decision process is indicated in FIG. 8A by the decision block 814. However, if higher resolution of the defect location is desired, then a second unpatterned wafer inspection step 818 is performed.

2. Second Pass

Continuing to FIGS. 2 and 8A, during the second inspection step 818, also referred to as the second inspection pass 818, each identified defect location is scanned in a raster pattern to identify the defect location at a second resolution. To scan the defect location identified during the first pass 812 at the second resolution, the turning mirror 518 is moved into the path of the expanded beam 516 to deflect the expanded light 516 and direct the expanded beam 516 toward the surface 104 at a second incident angle 558i. The second incident angle 558i is smaller than the first incident angle 540i and can be, for example, approximately 65 degrees with respect to the z-axis 129 which is normal (orthogonal) to the surface plane 104 and can range between 60 and 70 degrees.

Figure 9:
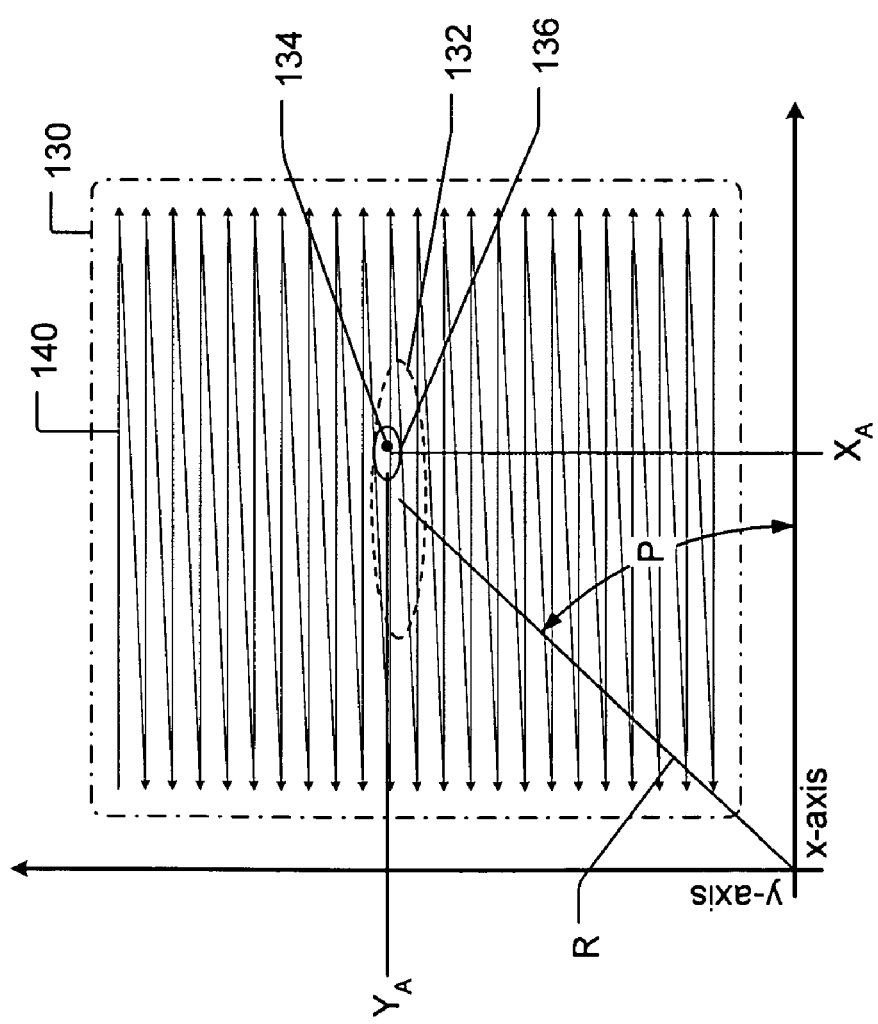
FIG. 9 illustrates a raster scan pattern in accordance with a first aspect of the present invention.

The deflected light 542 is redirected by a 2D scanner 544 to form a rectangular raster pattern on the surface 104. FIG. 9 illustrates a rectangular portion or area 130 of the surface 104 surrounding a sample defect location 132 (identified during the first pass 812) including a defect 134. Referring to FIGS. 2, 4, 7A, 8A, and 9, since the defect location 132 is identified during the first pass 812, the defect location 132 is identified with the first resolution. The redirected light reaches the surface 104 of the wafer 102u as already discussed at the second incident angle 558i as the focused light 549. The spot of the focused light 549 is illustrated in FIG. 9 as illumination spot 136. The illumination spot 136, like the spot 214 of FIG. 5B, has elliptical shape and has axis lengths in the order of microns or tens of microns, for example, 8 microns (minor axis) by 20 microns (major axis). The raster scan pattern is indicated by raster scan pattern vectors 140 in FIG. 9. The rectangular scan area portion 130 can have varying size. In the illustrated embodiment, the rectangular scan area portion 130 has lateral dimensions of approximately 300 microns by 300 microns. In alternative embodiments, the rectangular scan area portion 130 can have lateral dimensions of approximately 600 microns by 600 microns or even larger.

To realize the raster scan pattern in the rectangular scan area 130, the 2D scanner 544 forms raster scan pattern by quickly directing the deflected light 542 in x-axis and y-axis thereby moving the illumination spot 136 relative to the surface 104 of the wafer 102u. In another embodiment, the 2D scanner 544 can be used to move the illumination spot 136 in one axis (for example, in x-axis) while the stage 200 is moved in the other axis. In yet another embodiment, the stage 200 moves in both the x-axis and the y-axis thereby moving the wafer 102u relative to the illumination spot 136. In this case, the 2D scanner 544 is not needed.

As the illumination spot 136 scans the rectangular scan area 130 by moving in the raster pattern, the focused incident light 549 (illuminating portions of the rectangular scan area 130) is reflected, scattered, or both depending on the condition of the portion being illuminated. Scattered light is collected by the collectors of the three rings 610, 620, and 630 and directed to the PMT array 670 as optical signal. The optical signal is converted to electrical signal by the PMT array 670. The electrical signal is analyzed by the processor 310 to determine whether or not the electrical signal (representing the scattering light) suggests that the illuminated spot 136 includes defects. If the illuminated spot 136 includes defects, then the location of the illuminated spot 136 is identified as a defect location 136. The defect location is computed by adding the position of stage 200 and the position of the laser spot within the scan area 130 as reflected by reading the 2D scanner. The location information is saved in Cartesian coordinates, for example $(x_A, y_A)$.

As indicated in FIG. 9, the defect location as identified during the second pass 818, for example defect location 136 $(x_A, y_A)$ for the defect 134, is more precise or accurate compared to the defect location, for example defect location 132 $(r_i, \phi_i)$ identified during the first pass 812. In FIG. 9, for the defect location 132 $(r_i, \phi_i)$, radius $r_i$ is represented as R and angle $\phi_i$ is represented as P. This is because a smaller spot size of the illumination spot 136 is used for the second pass 818 compared to the larger spot size of the illumination are 132 used for the first pass 812. Thus, the defect 134 is identified in higher resolution in the second inspection pass 818. In the illustrated sample, the defect 134 lies within the illumination spot 136, and thus the location of the spot is deemed the defect location $(x_A, y_A)$ for the defect 134.

In fact, the second inspection pass 818 also operates to confirm or deny, as the case may be, the actual existence of the defect identified during the first inspection pass 812. Therefore, the second inspection step 818 reduces false defects, if any, which may have been identified during the first inspection pass 812.

The second inspection pass 818 is continued until each defect location identified in the first inspection pass 812 is scanned in the raster pattern to more accurately locate the identified defects at the second, higher resolution. Then, the memory 320 is updated with the more accurate defect locations. The defect location map, following the second inspection pass 818, is saved in the Cartesian coordinate format.

H. Marking Subsystem 700—Defect Marking

Figure 10:
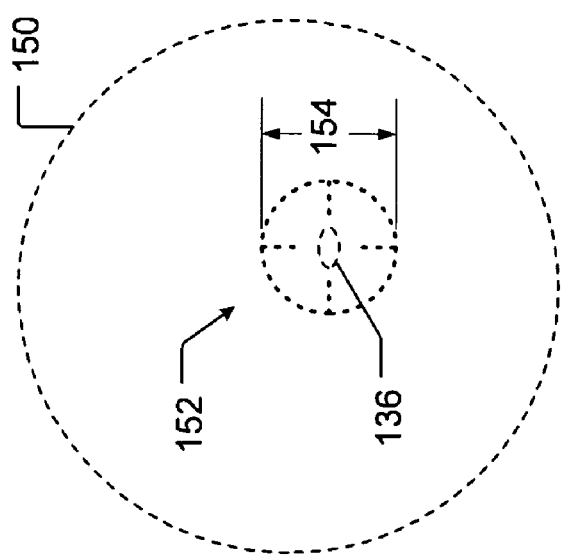
FIG. 10 illustrates a defect mark as a second aspect of the present invention.

Referring to FIGS. 1, 2, 4, 8A, and 10, following the second unpatterned inspection pass 818, the inspection system 100 provides for marking of the defects on the surface 104 of the wafer 102u. FIG. 10 illustrates a portion 150 of the surface 104 of the wafer 102u, the portion 150 including sample defect location 136 of FIG. 9, the location $(x_A, y_A)$. In FIG. 10, the defect location 136 is indicated as a dashed ellipse.

A defect mark helps an analytical system such as a secondary electron microscope (SEM) to easily locate the defect in subsequent processing stages. The marking subsystem 700 is mounted on a vertical moving stage (not shown). During inspection of the surface 104 of the article 102u, the marking subsystem 700 is positioned outside of the collection enclosure 602.

To mark the defect location, the marking subsystem 700 is lowered such that its marking subsystem objective 716 is lowered into the collection enclosure 602 toward the surface 104 of the article 102u. At the same time, the stage 200 is moved to position the article 102 such that the defect location 136 to be marked, for example $(x_A, y_A)$, is proximately under and generally aligned with the marking subsystem objective 716.

To mark the defect, a marking laser 702 is pulsed, or fired, a number of times. Each time the marking laser 702 is pulsed, marking laser beam 703 is generated. The marking laser beam 703 is directed toward the surface 104 where the marking laser beam 703 produces a small crater, or a dot, on the surface 104. Between each pulse of the marking laser 702, the wafer 102u is moved slightly such that, the sequence of dots results in dotted shape a sample of which is illustrated in FIG. 10 as a defect mark 152 including a circular mark around the defect location 136 and an incomplete cross-hair mark within the circular mark.

Before pulsing the marking laser 702, a marking subsystem first mirror 704 is moved away from the path of the marking laser beam 703 such that the marking laser beam 703, when generated by the marking laser 702, moves unimpeded toward a marking subsystem second mirror 706. The marking subsystem second mirror 706 reflects the marking laser beam 703 from the marking laser 702 toward the defect location 136 on the surface 104. The laser beam 703 blasts the surface 104 of the wafer 102u to produce the defect mark using a sequence of dots. The marking time for a single dot mark is determined by the laser pulse width (typically a few nanoseconds). However, the marking time for a patterned mark like a cross-hair is decided by the number of individual dot marks required and the amount of time it takes to move to each marking locations. For the present example, the time it takes to generate the defect mark 152 is in the order of a few seconds.

The marking laser 702 provides pulsed beam from either a $N_2$ (Nitrogen) laser or a 532 nm DPSS (Diode Pumped Solid State) laser. The marking laser 702 is connected to the processor 310. The processor 310 controls the operations of the marking subsystem 700 including all the components of the marking subsystem 700, for example, by controlling the amount of average laser power and the type of pattern for the defect mark 152. The laser beam 703 is focused on the surface 104 by the marking subsystem objective 716 to a narrow beam. The marking subsystem objective 716 can be, for example, a 20× long working distance objective lens.

The defect mark 152 can be any suitable pattern. In the illustrated embodiment, the defect mark 152 has dimensions 154 in the order of tens of microns or more, for example 50 to 100 microns in diameter.

I. Marking Subsystem 700—Imaging

Continuing to refer to FIGS. 1, 2, 4, 8A, and 10, the defect location 136, the defect mark 152, or both can be imaged using a marking subsystem imaging array 720 of the marking subsystem 700. Images taken by the marking subsystem imaging array 720 can be used for defect analysis and defect mark analysis as well as for calibration purposes. The marking subsystem imaging array 720 can be, for example, a CCD camera or a CMOS camera.

For the purposes of imaging the defect location 136, the defect mark 152, or both, additional light can be provided by a marking subsystem lamp 712 such as a halogen lamp. To image the defect location 136, the defect mark 152, or both, the marking subsystem lamp 712 is activated to provide imaging light 713. The marking subsystem first mirror 704 is positioned to reflect the imaging light 713 toward a marking subsystem beam splitter cube 714. The marking subsystem beam splitter cube 714 is on a slider assembly 715 with the marking subsystem second mirror 706 such that either the marking subsystem second mirror 706 or the marking subsystem beam splitter cube 714 can be positioned to intercept and redirect the imaging light (reflected by the marking subsystem first mirror 704) or the laser beam from the marking laser 702 toward the first objective 716.

To image the defect location 136, the defect mark 152, or both, the slider 715 is operated to place the marking subsystem beam splitter cube 714 to reflect the imaging light (reflected by the marking subsystem first mirror 704 toward the marking subsystem beam splitter cube 714) toward the surface 104 through the marking subsystem objective 716. The marking subsystem beam splitter cube 714 reflects 50 percent of the imaging light 713 toward the surface 104 via the marking subsystem objective 716. The imaging light is reflected from the defect location back toward the marking subsystem beam splitter cube 714 again via the marking subsystem objective 716. Half of the reflected light passes through the marking subsystem beam splitter cube 714 to be captured by the marking subsystem imaging array 720. The marking subsystem imaging array 720 is connected to the processor 310. The captured image is forwarded to the processor 310 for analysis.

J. Marking Subsystem 700—Coordinate System Marking

Continuing to refer to FIGS. 2 and 3A through 3B, the defect locations of the wafer 102*u* are designated relative to a reference coordinate system defined on the surface 104 of the wafer 102*u* by the inspection system 100. Thus, in order to locate the defect locations on the wafer, it is desirable for the wafer to include reference coordinate system marks. The reference coordinate system marks is useful for locating the marks when the wafer 102*u* is inspected by another inspection system or even by the same inspection system 100 but at a later time.

The marking subsystem 700 is used to make the reference coordinate system marks on the surface 104 of the wafer 102. For example, three coordinate system reference marks 131 can be made—all three marks near the edge but in different directions. For instance, illustrated in the FIGS. 3A and 3B are three marks 131, one each on the East edge, North edge, and West edge of the wafer 102 thus allowing the x-axis and the y-axis to be determined from the coordinate system reference marks 131. The coordinate system reference marks 131 are illustrated in FIGS. 3A and 3B as craters. The crater marks 131 are near the edge of the surface 104 as to avoid waste of useful wafer surface area. In alternative embodiments, the coordinate system reference marks 131 can have other shapes.

K. Inspection Method—Patterned Wafer

As already discussed, FIG. 8A illustrates the flowchart 800 outlining the operating modes for inspecting the wafer 102 in accordance with the present invention. The second mode 820 for inspecting patterned wafer includes two sub-modes of operation illustrated in more detail in FIG. 8B. Referring to FIGS. 2, 3B, 3C, and 8B, in the first submode 830, the patterned wafer 102*p* is scanned in the spiral pattern first then, if desired, scanned in the raster pattered in portions, thus a two scan step. In the second submode 850, the entire patterned wafer 102*p* is scanned in the raster pattern.

During patterned wafer inspection, optimal focus is achieved by using the electrical signal from the specula beam detector of a specula beam dump 550*a* or 550*b* signal to adjust the Z stage in a close loop fashion. That is, depending on the level of the electrical signal from the specula beam detector relative to a threshold, the Z stage can be raised or lowered to achieve the optimal focus.

1. Patterned Wafer Spiral and Raster Scan

Referring to FIGS. 2, 3B, 3C, 8B, and 9, in the first submode 830, the patterned wafer 102*p* is scanned in the spiral pattern, also referred to as the first patterned wafer inspection pass 832. Step 832. The first patterned wafer inspection pass 832 is performed in the similar manner as the unpatterned wafer first inspection pass 812 of FIG. 8A and 3B. In the first patterned wafer inspection pass 832, for each location (illuminated spot), pixel values ("test pixel data") from the channels are compared to its corresponding wafer position spiral scan reference pixel values that are read from a reference database. In another alternative embodiment, the spiral scan reference pixel values are stored pixel values from a spiral scan of another wafer.

Since there are variations of rotational speed and errors in wafer placement, the corresponding pixel data at the same position is not always the right match for the test pixel data. Accordingly, the inspection system 100 stores some recent pixel values and use them together as a pattern to compare the test pixel data to the corresponding pixel data neighboring around the same position to locate the right match. For each particular scanning position, and for each individual channel, the presence of a potential defect is detected if the signal difference of each matching channel pair, after normalized for illumination strength, is above a predefined fixed or adaptive threshold. A defect for this position is detected if the number of channels with potential defect is above a limit. Once a defect is detected, signal from each channel is recorded as part of the defect information.

Alternatively, pixel values from the channels are stored in the storage 320 as reference channel data or for later analysis rather than analyzed on the fly. As discussed, in the spiral scanning pattern, each location (illuminated spot) on the surface 104 is specified in polar coordinates, for example ($r_1$, $\phi_1$). For the patterned wafer 102*p*, signal from all azimuthal channels are individually collected and stored for all polar coordinate positions of the entire wafer.

For the first patterned wafer inspection pass 832, the rotation stage 210 spins the wafer 102p while one of the lateral movement stages 204 or 206 moves in a horizontal direction to effectuate the spiral scanning of the surface 104 of the wafer 102p. At the same time, an auto focus mechanism (a part of the z-stage 208) moves Z to keep the disc 102p at an optimal focus position. As before, the illumination spot size is around 25 microns by 125 microns.

Unlike an unpatterned wafer, the patterned wafer 102p includes patterns, typically a plurality of rectangular dies 110 arranged in a rectangular grid as illustrated in FIG. 3C. Accordingly, more of the incident focused light 528 is scattered from the surface of the patterned wafer 102p compared to the amount of the incident focused light 528 scattered by an unpatterned wafer. In fact, due to strong scattering signal from the light scattered by the patterns on the surface 104 of the patterned wafer 102p, it is difficult to distinguish light scattered by a defect from the light scattered by the patterns on the wafer 102p.

However, light scattering from a pattern (pattern-scattered light) can be recognized because pattern-scattered light has strong preference in discernable azimuthal direction. This is because of the rectangular grid layout of the patterns on the surface 104. In contrast, light scattering from a defect (defect-scattering light) is generally less directional and weaker in signal magnitude than the pattern-scattered light. The weaker defect scattering (of the defect-scatting light) is generally spread out in all directions, and the pattern-scattering light is concentrated to some distinct direction. For this reason, the inspection system 100 of the present invention includes multiple collectors at different azimuthal angles to collect data while preserving azimuthal angle information of the scattered light and to provide sufficient azimuthal angle resolution of the scatter pattern. Thus, the azimuthal resolution provided by the rings 610, 620, and 630 of the inspection system 100 of the present invention allows for distinction between the two types of scattering light.

The spiral scan reference wafer pixel database can be stored in the storage 320. The spiral scan reference wafer pixel database can be built from a spiral scan of a defect-free patterned wafer (reference wafer) having the same pattern as the patterned wafer 102p under test. For the reference wafer, signal from all azimuthal channels are individually collected and stored for all polar coordinate positions of the entire wafer.

Storage requirements for one such spiral scan reference pixel database depend on wafer size, data resolution, illumination spot size and number of data channels. For example, for a 300 mm wafer, 8 bit data, and a 25 micron by 100 micron illumination spot size, and 30 channels would be around 1,000 Megabytes. Various combinations of illumination spot size, number of channels, and data resolutions are within the scope of this invention. Alternatively, instead of using a defect-free wafer to build the spiral scan reference wafer pixel database, two almost-defect-free wafers can be spiral scanned, and the resulting pixel values can be combined to form a single defect-free spiral scan reference wafer database. Differences in scattering between the pixel values from the two scans can be resolved by an operator.

However, before each comparison is made, the matching reference pixel data from database is first identified and retrieved. Because of variations in scan speed, and wafer placement errors, the reference pixel data with the same sample position $(r_1, \phi_1)$ may not be the right match. The inspection system 100 stores some recent pixel values and uses them together as a pattern to compare the corresponding pixel data neighboring around the same position to locate the right match. The pixel values from the wafer 102p under test may also require intensity normalization to compensate for differences in the strength of the illumination source 510 from wafer to wafer.

After scanning is completed, all saved defect locations $(r_i, \phi_i)$ (in polar coordinate notation) are converted to equivalent Cartesian coordinate notation $(x_i, y_i)$ for all i from 1 to N where N is the number of the identified defect locations. Step 833. Coordinate system conversion techniques are known in the art. All defect locations are saved in the memory 320. A set of defect locations is also referred to as a defect location map.

Figure 8B:
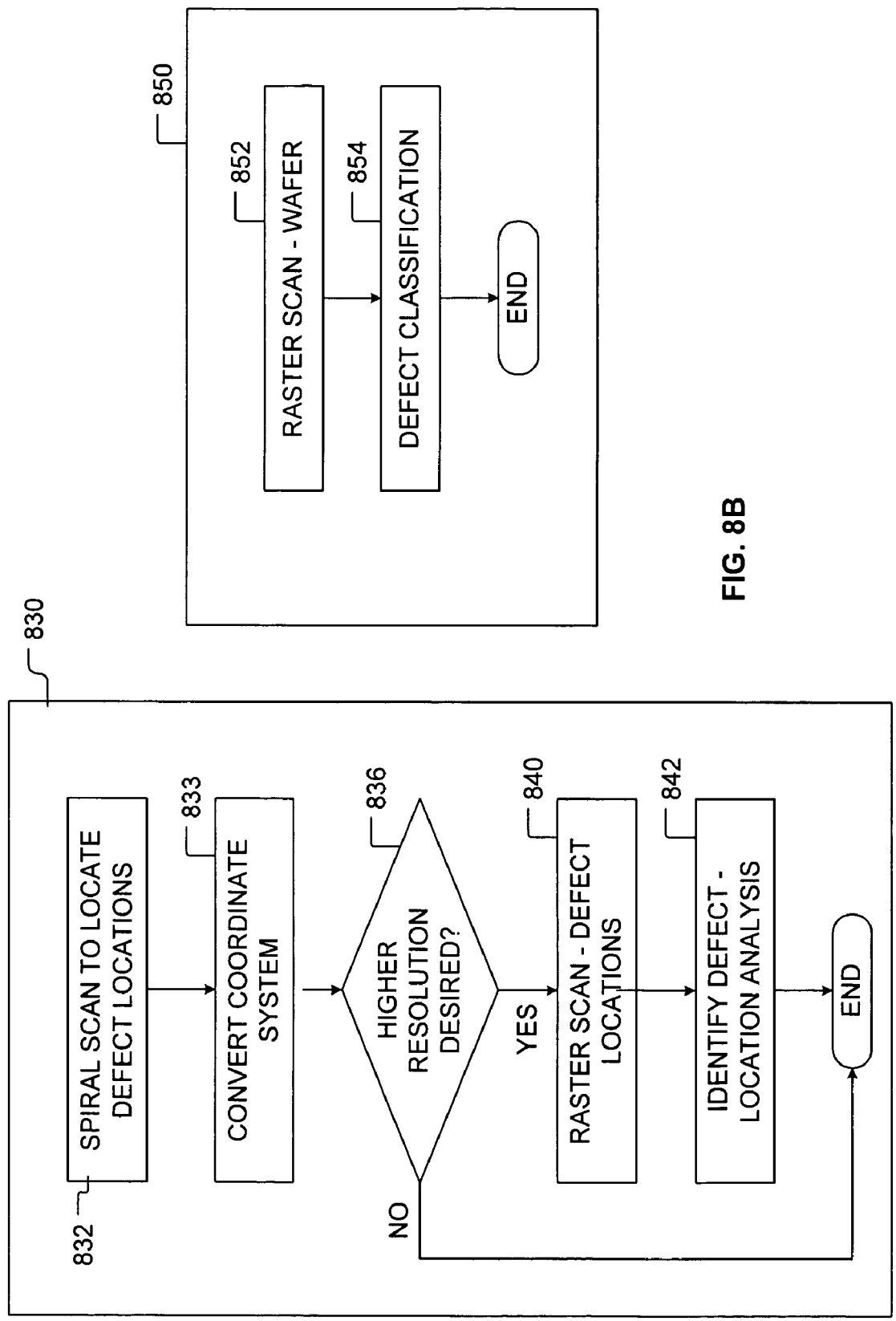

For some applications, it is sufficient to determine the total number of defect locations, N. For other applications, it is sufficient to determine the defect locations with the resolution available from the first patterned wafer inspection pass 832. For these applications, where higher resolution of the defect locations is not desired, the first submode 830 of the second mode of operation 820 is completed for the patterned wafer 102p under inspection. This decision process is indicated in FIG. 8B by the decision block 836. However, if higher resolution of the defect locations is desired, then a second patterned wafer inspection step 840 is performed.

For the first submode 830, the first patterned wafer inspection step 832 is intended to quickly locate defects on the patterned wafer 102p, and the second patterned wafer inspection step 840 is intended for providing more accurate defect coordinates on the surface 14 of the wafer 102p. For the second patterned wafer inspection step 840, also referred to as the second patterned wafer inspection pass 840, each identified defect location (from the step 832) is scanned in a raster pattern to identify the defect location at an increased resolution, to classify the defect type, or both. The second patterned wafer inspection step 840 for the patterned wafer 102p is performed in the similar manner as the raster pattern scan step 818 of the first mode 810 of operation discussed above using the smaller illumination spot size of 8 microns (minor axis) by 20 microns (major axis). That is, for the second patterned wafer inspection step 840, only scan regions 130 (of FIG. 9) around and encompassing the defect locations $(x_i, y_i)$ are scanned.

During the second patterned wafer inspection step 840 for the patterned wafer 102p, resulting pixel values (for all channels) for each illuminated spot location in Cartesian coordinates, for example $(x_A, y_A)$, are examined on the fly or stored in the storage 320. Then, the pixel values are compared to raster scan reference pixel values of corresponding Cartesian coordinates of a raster scan reference wafer pixel database to identify defect spots on the wafer 102p with higher degree of accuracy compared to the accuracy available using the polar coordinate defect locations $(r_i, \phi_i)$.

Alternatively, the raster scan reference pixel values are corresponding pixels values from corresponding location of another die on the surface of the patterned article 102p. In another alternative embodiment, the raster scan reference pixel values are stored pixel values from a spiral scan of another wafer.

During this second inspection pass of a patterned wafer, the X-Y stages move the wafer to those defect locations identified during the first pass 832. At each site, the Z stage is set to the optimal focus position by the auto focus mechanism. The 2D scanner scans the laser spot in a raster pattern to generate an image set. The collection subsystem 600 and the scanner are running in sync, so each pixel corresponds to a precise polar and azimuthal coordinate of a particular XY stage position. The scan area can be about 600 microns by 600 microns. The spot size is about 8 microns by 20 microns. Number of pixels for each image is 512 by 512. Each azimuthal channel generates one image, and images from all azimuthal channels make up the image set for the particular defect location.

A die-to-die comparison scheme can be used to subtract signal from the background features so the defect signal can be detected. Many die-to-die comparison methods are possible and have been described in the prior art cited. Typically, an image from current stage position is compared with image from adjacent dies. A defect is detected if test pixel value is greater than those from both adjacent die by a threshold, or test pixel value is less than those from both adjacent die by a threshold. This invention takes advantage of the many azimuthal channels available. Scattering signal from each azimuthal detection channel is compared to its corresponding channel signal from adjacent die for each pixel in the XY scan image. A potential defect is detected if the difference between the signal strength of an azimuthal channel and its corresponding channel exceeds a certain threshold. A defect for this defect location is detected if the number of channels with potential defect is above a limit. Since there are many detection channels, the system 100 can use a variety of detection criteria, for example: (a) threshold of individual channels, and (b) minimum number of required channels with signal above threshold.

Again, the pixel values can be compared to pixel values of corresponding positions of a nearby die, or pixel values can be compared to raster scan reference pixel values.

The raster scan reference wafer pixel database can be stored in the storage 320. The raster scan reference wafer pixel database can be built from a raster scan of a defect-free die of a patterned wafer (reference wafer) having the same pattern as the patterned wafer 102p under test. For the reference wafer, signal from all azimuthal channels are individually collected and stored for all Cartesian coordinate $(x_i, y_i)$ positions of the whole die. Storage requirements for one such raster scan reference pixel database depend on wafer size, data resolution, illumination spot size and number of data channels.

For example, a 10 mm by 10 mm die, 8 bit data, and an 8 micron by 25 micron illumination spot size for a 6 micron by 20 micron effective spot size (allowing some overlap between spots), and 30 channels require approximately $(10000 \times 10000 \times 30)/(6 \times 20) = 25$ Megabytes of storage space. Various combinations of illumination spot size, number of channels, and data resolutions are within the scope of this invention. Alternatively, instead of using a defect-free wafer to build the raster scan reference wafer pixel database, two almost-defect-free wafers can be raster scanned, and the resulting pixel values can be combined to form a single defect-free raster scan reference wafer database. Differences in scattering between the pixel values from the two scans can be resolved by an operator.

As indicated in FIG. 9, the defect location as identified following the second patterned wafer inspection step 840, for example defect location 136 $(x_A, y_A)$ for the defect 134, is more precise or accurate compared to the defect location, for example defect location 132 $(r_i, \phi_i)$ identified during the first pass 812. In FIG. 9, for the defect location 132 $(r_i, \phi_i)$, radius $r_i$ is represented as R and angle (pi is represented as P. This is because a smaller spot size of the spot 136 is used for the second patterned wafer inspection step 840 compared to the larger spot size of the illumination are 132 used for the first patterned wafer inspection pass 832. Thus, the defect 134 is identified in higher resolution following the second patterned wafer inspection step 840. In the illustrated sample, the defect 134 lies within the illumination spot 136, and thus the location of the spot is deemed the defect location $(x_A, y_A)$ for the illustrated defect 134.

In fact, the second patterned wafer inspection step 840 also operates to confirm or deny, as the case may be, the actual existence of the defect 134 identified during the first patterned wafer inspection pass 832. Therefore, the second patterned wafer inspection step 840 reduces false defects, if any, that may have been identified during the first patterned wafer inspection pass 832.

2. Patterned Wafer Raster Scan

Referring to FIGS. 1–3C, 8B, 9, and 11, in the second submode 850, the entire surface 104 of the patterned wafer 102p is scanned in the raster pattern, also referred to as the patterned wafer raster inspection pass 852. Step 852.

Figure 11:
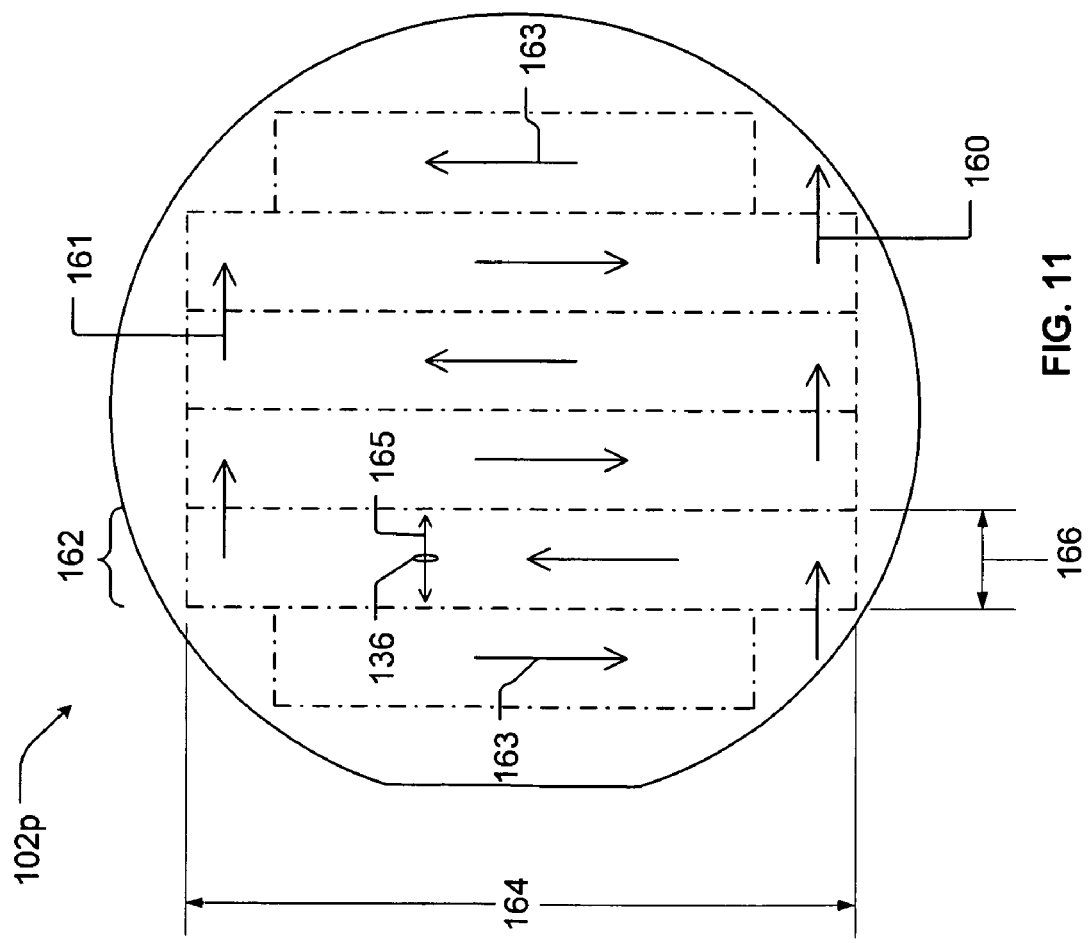
FIG. 11 illustrates a wafer scan pattern as a third aspect of the present invention.

There are various ways to raster scan the entire surface 104 of the patterned wafer 102p. For the illustrated embodiment of the inspection system 100 of the present invention, the patterned wafer raster inspection pass 850 is achieved by having a first lateral stage (for example, the x-stage 204) step 161 through columns 162. In FIG. 11, to avoid clutter, only one column is designated with reference numeral 162; however, each the reference numeral 162 is used to indicate any column or all columns, and column steps are indicated by horizontal vectors 161. At each column 162, the second lateral stage (for example, the y-stage 206) moves the entire length 164 of the column 162 such that the illumination spot 136 produced by the focused light 549 traverses the length 164 of the column 162. In FIG. 11, the traversal of the illumination spot 136 for the entire width 166 of each of the columns 162 is indicated by horizontal vectors 165. The column 162 can have width 166 of, for example, 1,000 microns. The column width 166 is limited by the scan angle of 2D scanner 544, and the field-of-view of the light collection subsystem 600.

Within a column 162, the second lateral stage (for example, the y-stage 206) moves in the vertical direction (in the illustration) while the 2D scanner 544 directs the illumination spot 136 in a line 165 bounded by the column edges as indicated by vector 165 to scan across the column 162 thereby causing the illuminating light to scan a scan area on the surface. The illumination spot 136 has elliptical shape and has axis lengths that can range in the order of microns or tens of microns, for example, 8 microns (minor axis) by 20 microns (major axis) to 25 microns by 60 microns. Size of the illumination spot 136 can be set by the operator. At each location of the wafer (addressable by the Cartesian coordinate $(x_A, y_A)$), as scanned by the two lateral stages (for example, the y-stage 206, and the x-stage 204) and the 2D scanner 544, pixel values from each of the channels are stored in the storage 320.

As scattering light is collected at each spot location, a die-to-die comparison scheme can be used to subtract signal from the background features so the defect signal can be distinguished from the background signal. Many die-to-die comparison methods are possible and are known in the art. Typically, the pixel data ("test pixel value") from current stage position is compared with pixel data from adjacent dies. A defect is identified if test pixel value is greater than those from both adjacent die by a threshold, or test pixel value is less than those from both adjacent die by a threshold.

This invention takes advantage of the many azimuthal channels available. Scattering signal from each azimuthal detection channel is compared to its corresponding channel signal from adjacent die for each spot in the raster scan. A potential defect is identified if the difference between the signal strength of an azimuthal channel and its corresponding channel exceeds a certain threshold. A defect for this defect location is identified if the number of channels with potential defect is above a limit. Since there are many detection channels, the system 100 can use a variety of detection criteria, for example: (a) threshold of individual channels, and (b) minimum number of required channels with signal above threshold. Again, as an alternative, the pixel values can be compared to stored pixel values of corresponding positions from a reference die.

Defect classification step 854. The shape and composition of each defect generate different scattering pattern. The azimuthal resolution provided by the rings 610, 620, and 630 of the inspection system 100 of the present invention can resolve these differences and use them to identify defects into difference classes.

L. Sample Scatter Signal Calculations

The three rings 610, 620, and 630 of collectors provide a good resolution of scatter signals at various azimuthal and polar angles. For detection of various defects, scatter signals from certain azimuthal and polar angles are more useful than scatter signals from other azimuthal and polar angles.

Figure 12A:
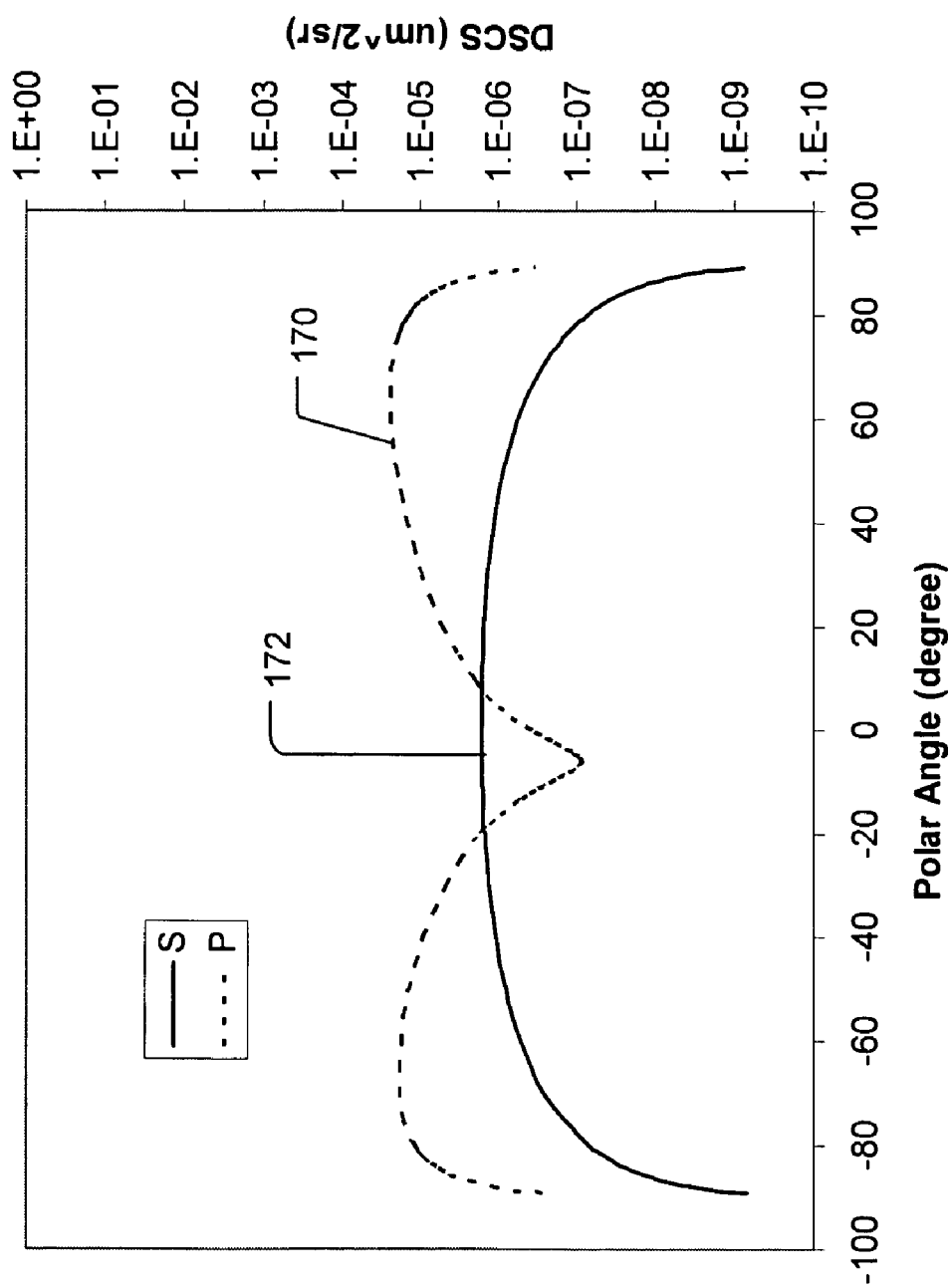
FIGS. 12A, 12B, and 12C are graphs representing results of analysis as a fourth aspect of the present invention.
Figure 12B:
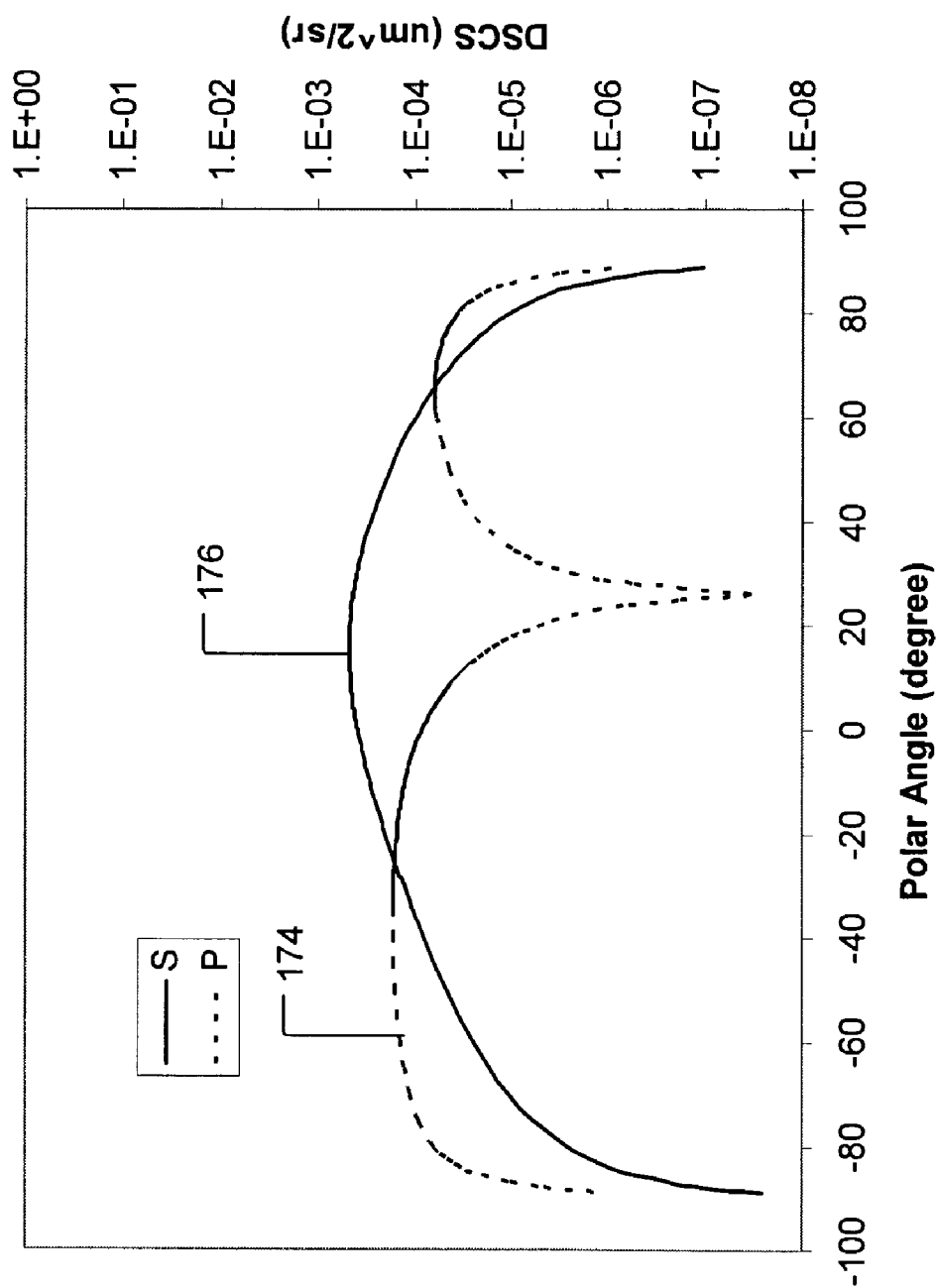
Figure 12C:
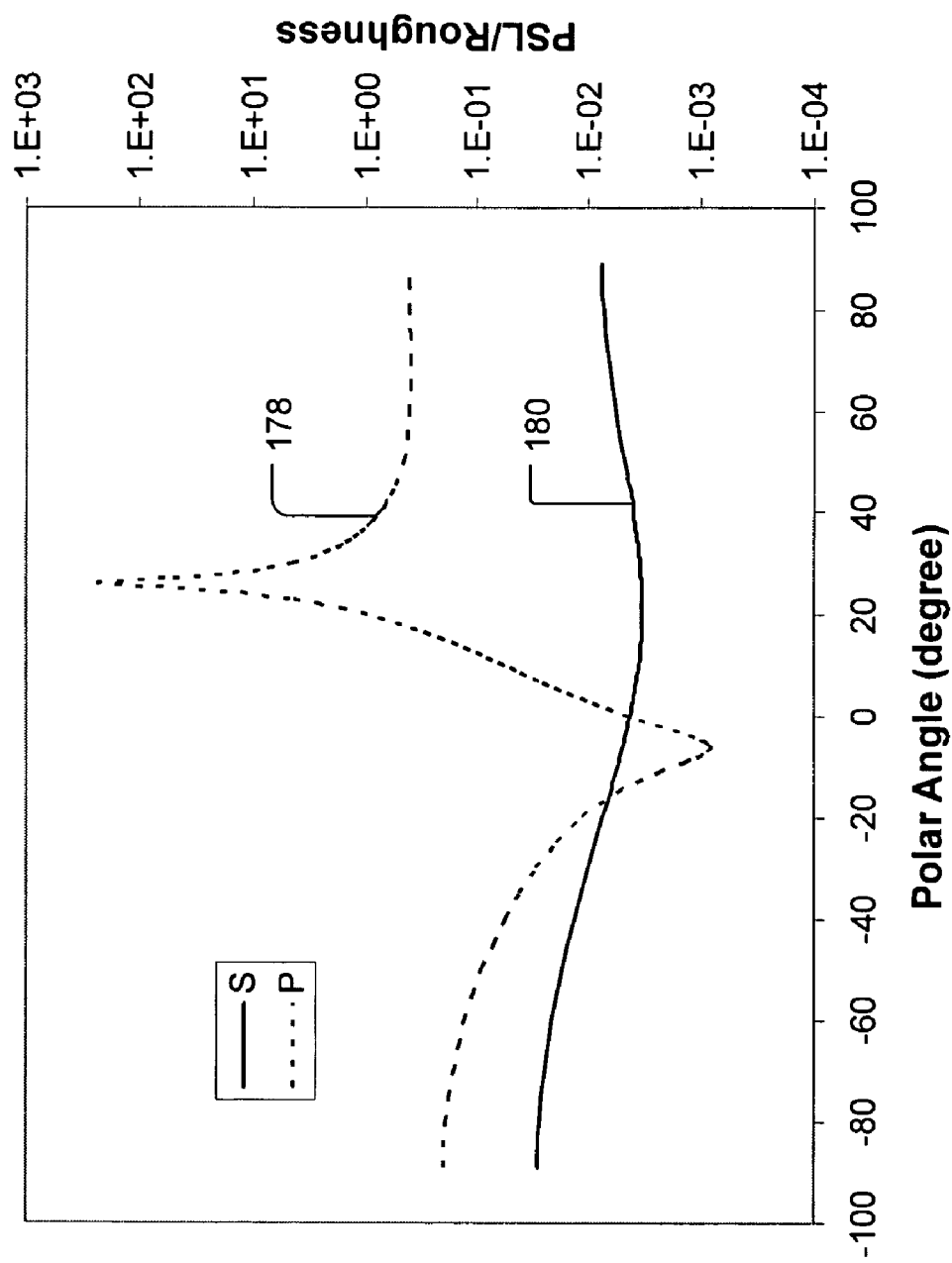

FIGS. 12A, 12B, and 12C illustrate theoretical calculation of laser scattering differential cross-section (DSCS) of a smooth wafer surface with a 50 nm polystyrene latex (PSL) sphere as a sample defect in FIG. 12A; DSCS of a silicon wafer having surface with micro-roughness in FIG. 12B; and ratio of the DSCS of FIG. 12A to the DSCS of FIG. 12B in FIG. 12C. Referring to FIGS. 2, 12A, 12B, and 12C, in the present example, the illumination used is p-polarized 266 nm light from the laser 510. The incident angle 540$i$ is approximately 78 degrees with respect to the surface normal. The azimuthal angle is at 65 degrees relative to x-axis line 115 as illustrated in FIG. 3A.

In the present example, power spectral density function for micro-roughness is $0.01/[1+(360f)^2]^{(3.13/2)}$. The parameters used to describe micro-roughness vary with sample. The present set of parameters is merely one possible set of parameters and are valid for the present example.

FIG. 12A shows the differential scattering cross section (DSCS) of a smooth bare silicon surface with a 50 nm polystyrene latex sphere (PSL), as a sample defect particle, on a smooth unpatterned silicon wafer surface as a function of polar angle at fixed azimuthal angle of 65 degrees. In FIGS. 12A, 12B, and 12C, the polar angle ranges from −90 to 90 degrees for a total of 180 degrees with respect to the z-axis marker 129 of FIG. 3A. The first DSCS curve 170 represents signal strength of scattered light on a particular test location (including the PSL sphere) of the surface of an unpatterned wafer illuminated with p-polarized illumination light. The second DSCS curve 172 represents signal strength of scattered light on the test location of the surface of the smooth unpatterned wafer with 50 nm PSL illuminated with s-polarized illumination light. As illustrated by the first DSCS curve 170, for p-polarized illumination light, the scattering pattern peaks at polar angles of approximately 60 to 80 degrees, and is minimal near zero polar angle (normal to the surface) and at 90 and −90 degrees. As illustrated by the second DSCS curve 172, for s-polarized illumination light, the scattering pattern peaks between −30 and 30 degrees and is minimal near 90 and −90 degrees.

FIG. 12B shows the differential scattering cross section (DSCS) of an unpatterned silicon wafer surface having micro-roughness as a function of polar angle at fixed azimuthal angle of 65 degrees. The third DSCS curve 174 represents signal strength of scattered light on a particular test location of the surface of the unpatterned wafer with micro-roughness illuminated with p-polarized illumination light. The fourth DSCS curve 176 represents signal strength of scattered light on the test location of the surface of the unpatterned wafer with micro-roughness illuminated with s-polarized illumination light. As illustrated by the third DSCS curve 174, for p-polarized illumination light, the scattering pattern valleys at polar angles of approximately 20 to 30 degrees as well as near 90 and −90 degrees. As illustrated by the fourth DSCS curve 176, for s-polarized illumination light, the scattering pattern peaks near 20 degrees and is minimal near 90 and −90 degrees.

As illustrated in FIGS. 12A and 12B, scattering signal strength (DSCS values represented by curves 174 and 176) from the wafer with micro-roughness surface is generally greater than scattering signal strength (DSCS values represented by curves 170 and 172) from the wafer with a PSL sphere (sample defect).

For this reason, it is difficult to identify small defects on a silicon wafer having surface with micro-roughness. This is because the scattering signal strength (unwanted signal, noise) from the micro-rough surface overwhelms scattering signal strength (desired signal) from the defect.

However, by comparing the PSL sphere (defect) curves 170 and 172 to the micro-roughness surface curve 174 and 176, respectively, a defect pattern can be determined. FIG. 12C shows a first ratio curve 178 representing the ratio of values of the curve 170 to that of the curve 174, and a second ratio curve 180 representing the ratio of values of the curve 172 to that of the curve 176. As illustrated in FIG. 12C, with p-polarized illumination light, a sharp peak exists in the ratio of the defect scatter curve 170 to the micro-roughness scatter curve 174 near polar angles near 24 to 28 degrees. That is, if the p-polarized scattering light is collected near 26 degrees polar angle and 65 degrees (present in this example) azimuthal angle, it is easier to distinguish defect signal from noise (from a rough surface).

Therefore, under the set of parameters outlined above, calculation for the present example shows that the best signal to noise ratio for determination of surface defect occurs at 26 degree polar angle and 65 degrees azimuthal angle. Thus, it is easier to determine the existence of defects from mere surface roughness when scatter signal is collected from collectors near 65 degrees azimuthal angle and near 26 degree polar angle. Furthermore, additional calculations show that such sharp peak (illustrated in FIG. 12C for the curve 178 near 26 degrees) also exists among channels with various combinations of azimuthal angles and polar angles. A summary of the additional calculations is shown by TABLE 1 below:

TABLE 1

| Azimuthal Angle Φ | Peak Ratio: PSL/Micro-roughness | Polar Angle θ at the peak |
|---|---|---|
| 20° | 5 | 81° |
| 25° | 10 | 72° |
| 30° | 18 | 65° |
| 35° | 30 | 59° |
| 40° | 46 | 53° |
| 45° | 63 | 48° |
| 50° | 99 | 42° |
| 55° | 119 | 37° |
| 60° | 147 | 31° |
| 65° | 239 | 26° |
| 70° | 218 | 21° |
| 75° | 88 | 16° |
| 80° | 59 | 10° |
| 85° | 64 | 5° |

To take advantage of this phenomenon (the sharp peak), linear polarizers can be placed in front of or behind selected channels having a predetermined polar and azimuthal position so as to collect p-polarized light. Again, as illustrated in FIG. 12C and demonstrated in TABLE 1, signals from the selected channels provides the sharp peaks allowing easier detection of the defect.

FIG. 7A illustrates that, in one embodiment, the polarizer 644 is placed behind the lens 640. Further, a band-pass filter 642 is placed in front of the collection lens 640 to allow 266 nm wavelength radiation (in the present example) to pass while blocking other radiation including visible light. This configuration reduces background noise caused by ambient light leaks since most production environment has little exposure to 266 nm light.

IV. Defect Review System 1000 and Method 1800

A. Overview

Figure 13:
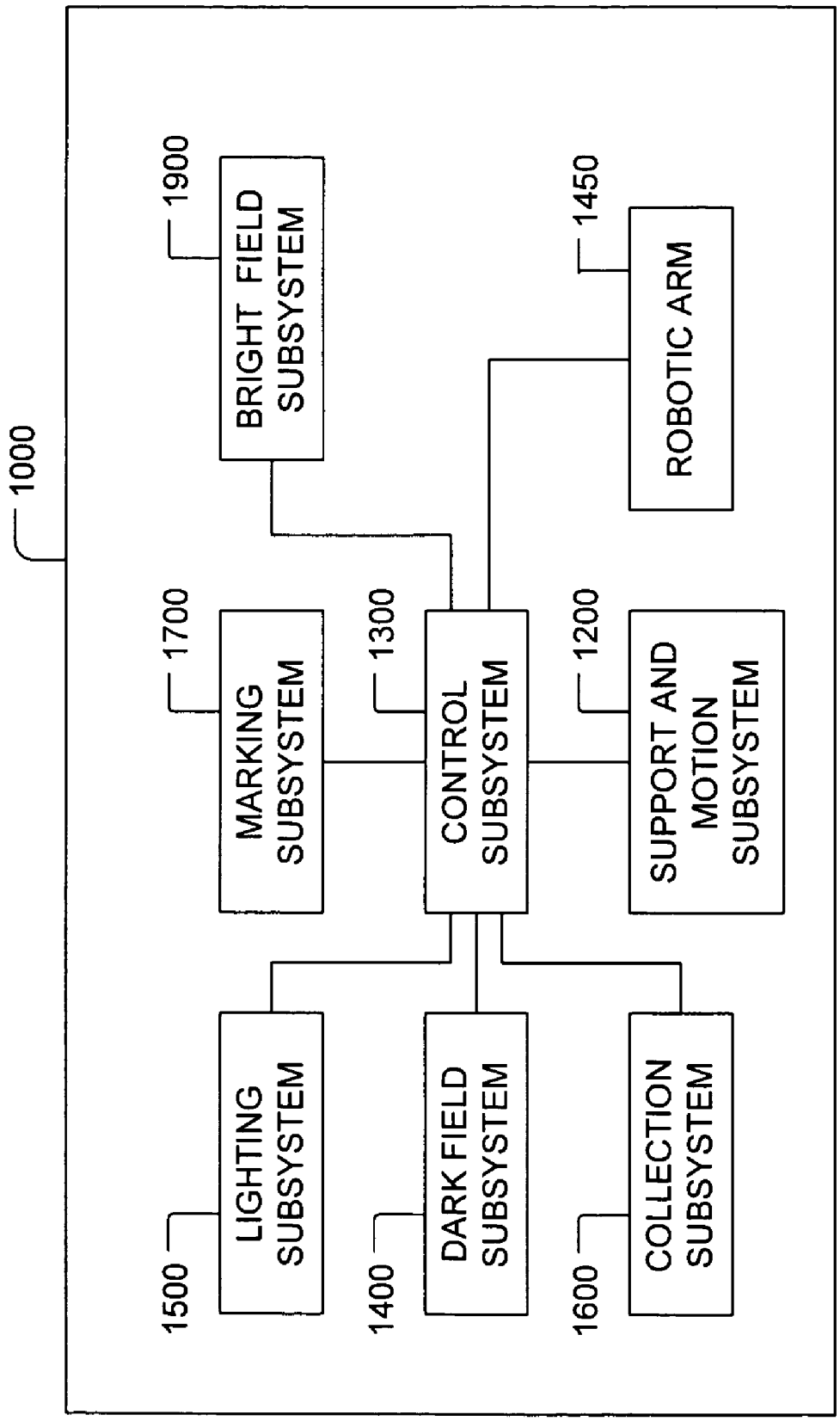
FIG. 13 is a defect review system in accordance with a third embodiment of the present invention.

FIG. 13 is a block diagram illustrating a defect review system 1000 in accordance with one embodiment of the present invention including major components of the defect review system 1000. The defect review system 1000 is an improved system for reviewing defects on silicon wafers, the defects found previously by various types of defect inspection systems such as the inspection system 100 of FIG. 1.

Portions or components of the defect review system 1000 as illustrated in FIGS. 13–18B and discussed below are similar to corresponding portions or components of the inspection system 100 as illustrated in FIGS. 1–12 and discussed above. To avoid clutter or repetition, those portions or components of the defect review system 1000 (FIGS. 13–18B) that are similar to corresponding portions or components of the inspection system 100 (FIGS. 1–12) are assigned the same reference numerals.

The defect review system 1000 includes many components and is, for the purposes of discussion herein, described as having subsystems illustrated in FIG. 13; however, it is understood that the discussion of the defect review system 1000 in terms of the subsystems and the illustrations and discussions of various components of the defect review system 1000 as a part of one of the illustrated subsystems are not intended to limit the structure of the defect review system 1000 to the illustrated embodiment.

Referring to FIG. 13, the defect review system 1000 includes a support and motion subsystem 1200 adapted to support an article such as a silicon wafer for inspection. Further, the support and motion subsystem 1200 is adapted to move (translate laterally (horizontally and vertically), and translate vertically) the wafer to allow any and all portions of the surface of the wafer to be inspected. The support and motion subsystem 1200 is connected to a control subsystem 1300 that includes a processor operable to control the movements of the support and motion subsystem 1200.

To place the wafer onto the support and motion subsystem 1200, a robotic arm 1450 picks up the wafer from another device and moves the wafer over the support and motion subsystem 1200. It is desirable to place the wafer on the support and motion subsystem 1200 in a known or in a predetermined location and orientation. For this purpose, the robot system 1450 includes a pre-aligner to align the wafer orientation with respect to the defect review system 1000.

Once the wafer is placed on the support and motion subsystem 1200, its surface is reviewed and analyzed using dark-field illumination technique, bright-field illumination technique, or both. The dark-field illumination review and analysis are performed using the dark-field subsystem 1400 and a collection subsystem 1600. The bright-field illumination analysis review and analysis are performed using the bright-field subsystem 1900.

For both the dark-field analysis and the bright-field analysis, a lighting subsystem 1500 provides the necessary radiation for illumination of the wafer. In this document, the term "light" is intended to encompass visible light as well as to encompass radiation outside or beyond the visible light spectrum. When a defect is located, the defect location may be marked using a marking subsystem 1700, also connected to the control subsystem 300.

B. Support and Motion Subsystem 1200

Figure 14:
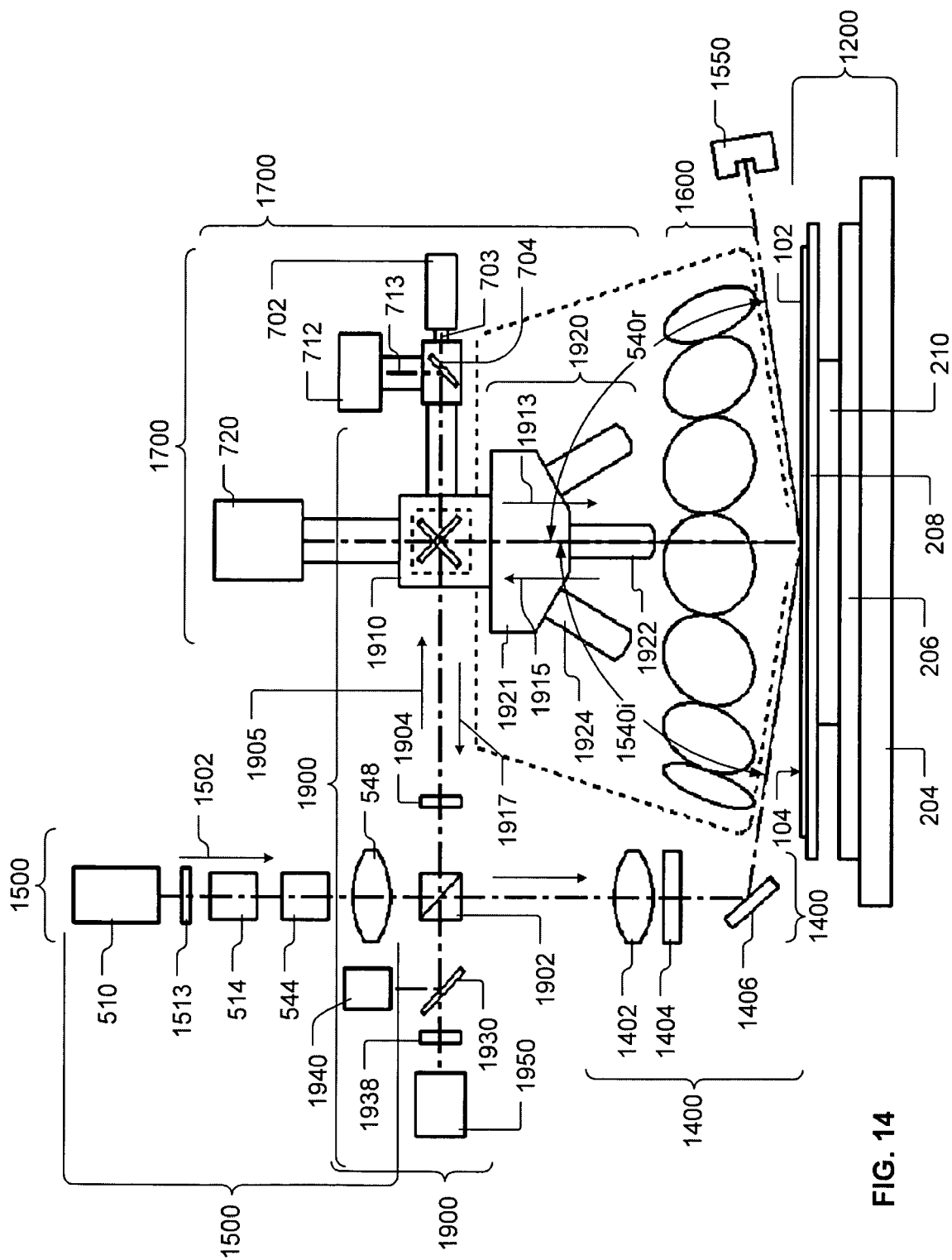
FIG. 14 is a more detailed view of portions of the defect review system of FIG. 13.

Portions of the defect review system 1000 of FIG. 13 are illustrated in greater detail in FIG. 14. Referring to FIGS. 13 and 14, the support and motion subsystem 1200 is similar to the support and motion subsystem 200 of FIGS. 1 and 2. The x-stage 204, the y-stage 206, the z-stage 208 of the support and motion subsystem 1200 are configured and operate similar to the x-stage 204, the y-stage 206, the z-stage 208, and the rotation stage 210 of the support and motion subsystem 200 illustrated in FIGS. 1 and 2 and discussed above. For the defect review system 1000, the rotation stage 210 is not required.

Coordinate systems used for the defect review system 1000 are the same coordinate systems used for the inspection system 100 of FIG. 1. These coordinate systems—Cartesian, polar, and spherical coordinate systems—are illustrated in FIGS. 3A and 3B and discussed above.

C. Control Subsystem 1300

Figure 15B:
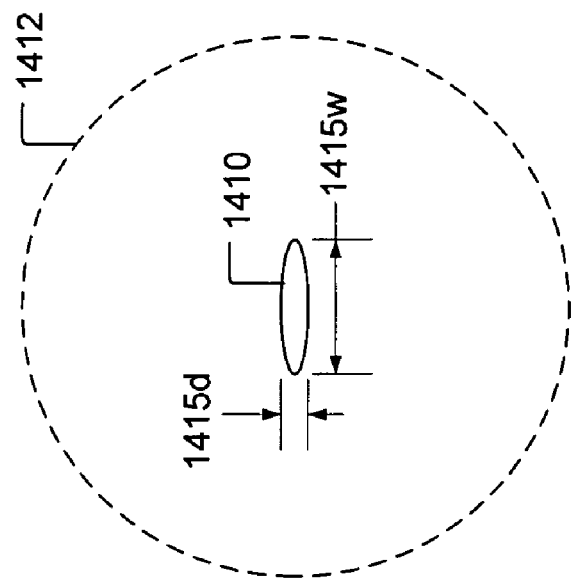
FIG. 15B illustrates a portion of the surface of an article under review.
Figure 15A:
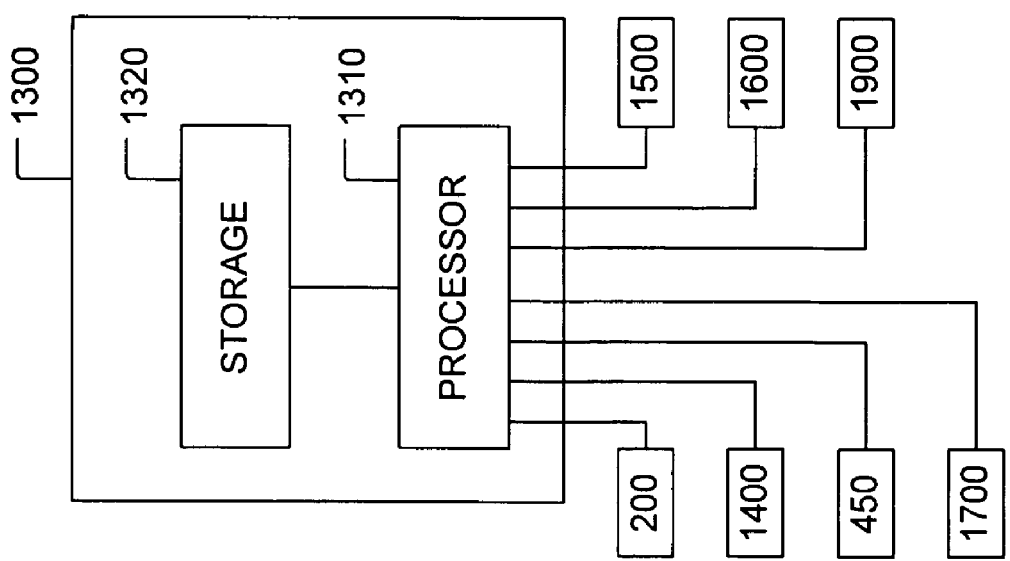
FIG. 15A is a more detailed view of another portion of the defect review system of FIG. 13.

FIG. 15A illustrates the control subsystem 1300 of FIG. 13 in greater detail. As illustrated in FIGS. 13 and 15A, the control subsystem 1300 is connected to all the other subsystems of the defect review system 1000 as well as to the robotic arm 1450. The control subsystem 1300 includes a processor 1310 configured or operable to control these subsystems and the robotic arm 1450. The control subsystem 1300 may include memory 1320 or storage 1320 adapted to store of instructions for the processor 1310, various data that is received, generated, or processed by the processor 1310, or both.

D. Lighting Subsystem 1500

Continuing to refer to FIGS. 13 and 14, light for the defect review system 1000 is provide by the lighting subsystem 1500 including an illumination source 510, a illumination source shutter 1513, a beam expander 514, a 2D scanner 544, and a scan lens 548. The illumination source 510 can be, for example, a laser adapted to emit illuminating light, and can be, for example, a continuous wave (CW) laser at 266. The laser 510, the beam expander 514, the 2D scanner 544, and the scan lens 548 are also illustrated in FIG. 2 and discussed in more detail above. The laser shutter 1513 is used to control whether or not the emitted illuminating light from the laser 510 reaches the beam expander 514 and the rest of the system. A vector 1502 illustrates the general flow of the illuminating light from the laser 510 toward the other subsections of the defect review system 1000. The 2D scanner 544 can be used to scan the beam in a 2D raster pattern on the wafer surface.

E. Dark-field Subsystem 1400

For dark-field illumination of the wafer 102, the illuminating light from the lighting subsystem 1500 is allowed to reach the dark-field subsystem 1400 by moving a polarizing beam splitter 1902 away from the path of the illuminating light from the lighting subsystem 1500.

The dark-field subsystem includes a relay lens 1402, polarizer 1404, and a turning mirror 1406. The relay lens 1402 relays the illuminating light from the lighting subsystem 1500 toward the turning mirror 1406. Here, the polarization filter 1404 filters out s-polarized light to reduce noise and allows only p-polarized light to pass toward the turning mirror 1406. The turning mirror 1406 turns the light toward the surface 104 of the wafer 102 at an incident angle 1540$i$. The incident angle 1540$i$ is typically an oblique and large grazing angle that can be, for example, approximately 80 degrees with respect to the z-axis 129 (illustrated in of FIG. 3A) which is normal (orthogonal) to the surface plane 104.

The turned light is incident on and illuminates an area of the surface 104 of the wafer 102. The illuminated area is often referred to as a "spot" or "laser spot," and the dimensions or the size of the illumination area is often referred to as a spot size. FIG. 15B illustrates a sample illumination area 1410 within a portion 1412 of the surface 104 of the wafer 102. In the present example, the laser spot 1410 has elliptical shape and has minor axis 1415$d$ length of approximately 8 microns and major axis 1415$w$ length of approximately 45 microns. The laser spot 1410 is scanned across a rectangular area by the 2D scanner 544. This is scanning dark field review.

Much of the incident light is reflected having a reflection angle 1540$r$ that has the same angular value as the first incident angle 1540$i$. This specula reflection of light is captured by a beam dump 1550. The beam dump 1550 also includes a photo detector (specula beam detector) to convert the captured light to electrical signal. The electrical signal can be used to analyze and correct intensity fluctuations of the emitted light from the light source 510.

A portion of the incident light is scattered by defects at the laser spot on the surface 104 of the wafer 102. The scattered light is captured by collectors of the collection subsystem 1500 further discussed below. The dark-field subsystem 1400, in combination with the collection subsystem 1500 described below with additional details, is typically used to review defects of unpatterned wafers.

F. Collection Subsystem 1500

Figure 16A:
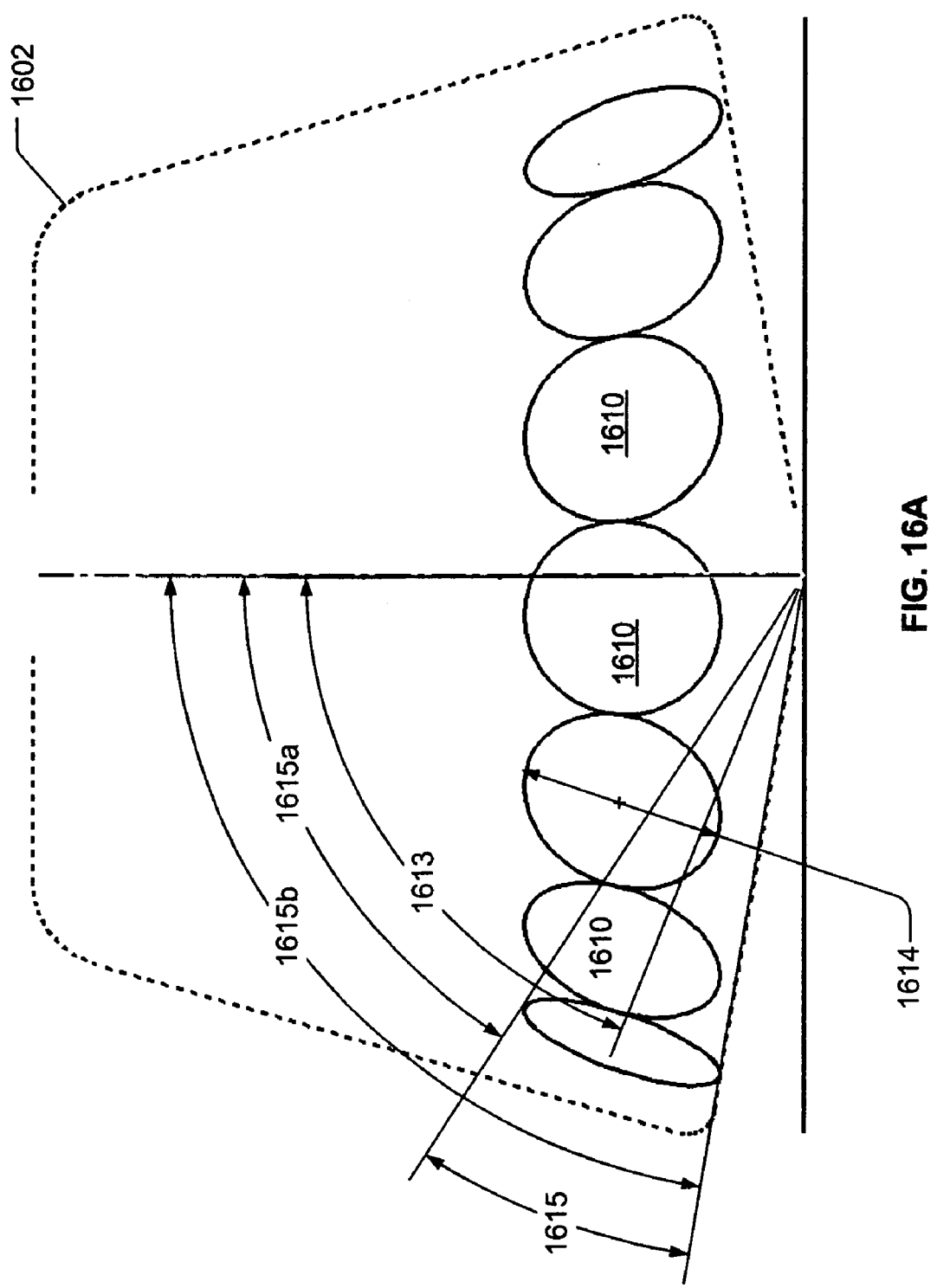
FIGS. 16A is a side view and 16B is a top view of portions of the defect review system of FIG. 13 in greater detail.
Figure 16B:
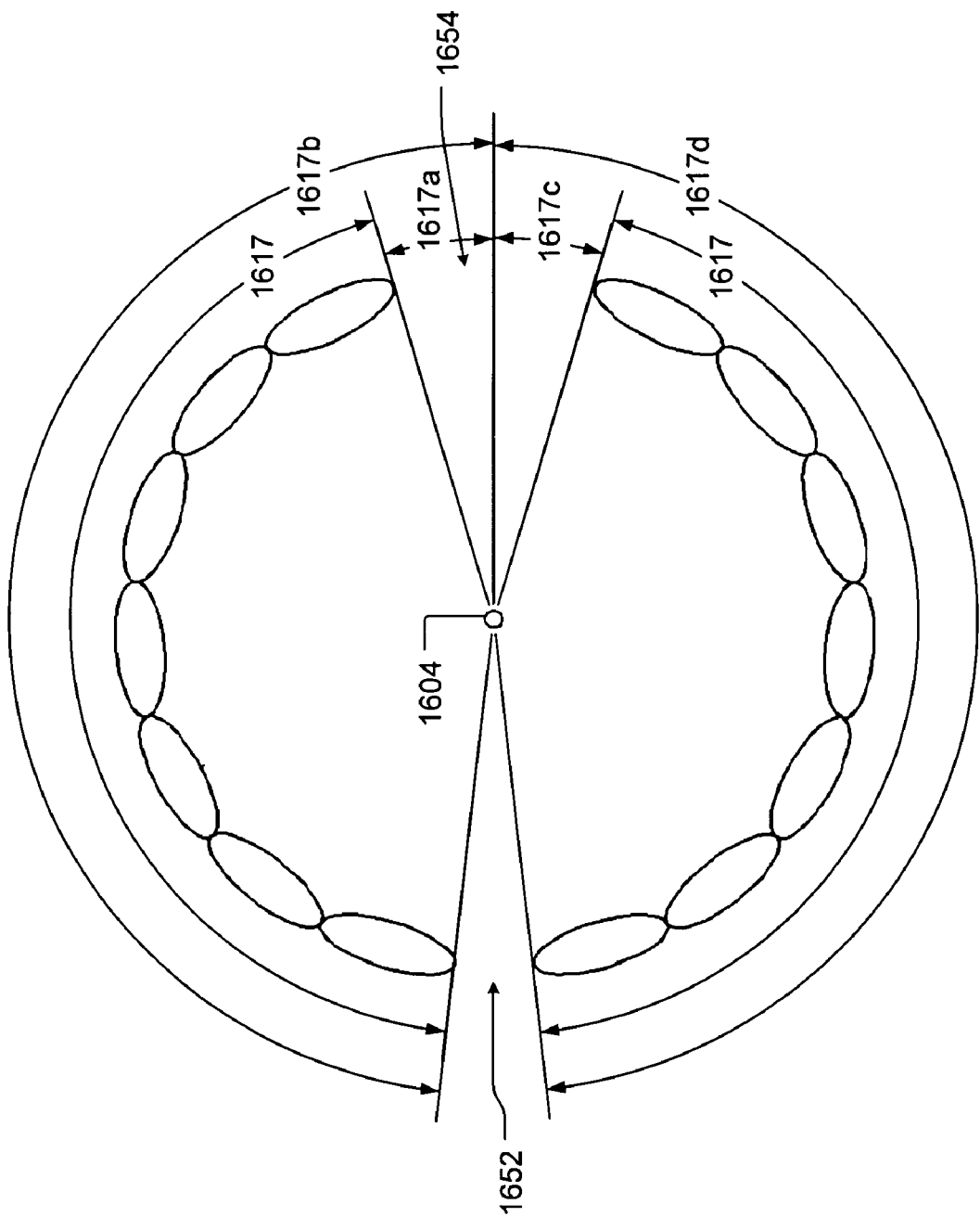

FIG. 16A illustrates a side view of the collector subsystem 1500 and FIG. 16B illustrates a top view of the collector subsystem 1500. Referring to FIGS. 14, 16A, and 16B, a set 1610 of collectors adapted to collect the scattered light is arranged in a ring having a first polar angle 1613. For this reason, the set 1610 of collectors is also referred to as the ring 1610 of collectors. Each individual collector of the ring 1610 of collectors has a collector diameter 1614 and is placed to collect scattering light between a polar angle range 1615. The polar angle range 1615 spans, for example, from approximately 60 degrees to approximately 80 degrees as illustrated by angles 1615$a$ and 1615$b$, respectively. The ring 1610 of collectors can include any number of individual collectors. In the illustrated embodiment, the ring 1610 of collectors includes 14 collectors arranged in generally a circular pattern around a field of view 1604. To avoid clutter, not all collectors of the ring 1610 of collectors are designated with the reference numeral 1610. For those skilled in the art, it is understood that the number of collectors, or lenses, in the ring 1610 may vary depends on angular resolution required by a specific application. Such variations are within the scope of this invention.

The ring 1610 of collectors is located to collect scattering light within an azimuthal angle range 1617, for example, from approximately 16 degrees to approximately 174 degrees as illustrated by angles 1617$a$ and 1617$b$, respectively as well as from approximately −16 degrees to approximately −174 degrees as illustrated by angles 617$c$ and 617$d$, respectively. A first gap 1652 allows injection of the light from the turning mirror 1406 toward the field of view 1604. A second gap 1654 allows the specula reflection of the light from the turning mirror 1406 to travel from the field of view 1604 to the beam dump 1550 as well as to prevent collection of the reflected portion of the light from the turning mirror 1406 by the collectors. Each collector lens is focused on and collects light from the field of view (FOV) 1604 area on the surface 104 as illustrated in FIG. 17A.

The collection optics are enclosed (except an opening at the bottom straight above the wafer at the inspection site) in a light shield 602 to keep ambient light from reaching the collectors. Every collector lens can be coated with anti-reflection coating to reduce reflection noise.

Referring to FIGS. 13, 14, and 17A, the FOV 1604 is located generally on the same plane as the surface plane 104 and is centrally located relative to the ring 1610 of collectors 1610. The FOV 1604 is generally circular in shape. The size of the FOV 1604 is a function of lens property of the collectors as well as the polar angle of the rings. In the illustrated embodiment, the FOV 1604 is approximately 0.7 mm in diameter. The FOV 1604 is larger than the spot 1410 (illustrated in FIG. 15B).

Initially, when the wafer 102 is placed on the stage 1200, the FOV 1604 coincides with the origin which is the center of the wafer 102. As the stage 200 moves relative to the ring 1610 of collectors, the FOV 1604 moves across the surface 104 to allow for the scanning and examination of the entire surface 104 of the wafer 102; thus, the FOV 1604 is not always coincident with the origin 119 (illustrated in FIGS. 5A and 5B) of the wafer 102.

FIG. 17A illustrates additional portions of the collection subsystem 1600. Portions or components of FIG. 17A are similar to corresponding portions of FIG. 7A. Again, similar corresponding portions or components are assigned the same reference numerals. Referring to FIG. 17A, an individual collector lens 640 can be preceded or followed by a band-pass filter 642 and followed by a retractable polarizing filter 644 (also, "polarizer" 644). The collector lens 640 represents any one of the collectors from the ring 1610 of collectors. A collector 640 is a lens adapted to gather scattering light from the FOV 1604.

The band-pass filter 642 is used to block unwanted light to decrease noise, thus increasing signal-to-noise (S/N) ratio in the collected information. For example, when using 266 nm laser as the illumination source 510 (of FIG. 13), the band-pass filter 642 allows 266 nm wavelength light to pass while blocking light having different wavelengths including visible light. This reduces collection of ambient light leaked into the defect review system 1000 and other light noise by the collection lens 640.

The retractable polarizing filter 644 can be used for selected collector lenses to improve the S/N ratio for certain application. For example, for inspecting unpatterned wafers for defects, angular information in the polar and azimuthal directions is unique depending on surface texture, polarization state of the light, and defect properties. For reviewing unpatterned wafers (with micro roughness surface texture), the S/N ratio between defect and micro-roughness improves significantly in some azimuthal directions than in others.

TABLE 2 below shows the S/N ratio as a function of azimuthal angle. The parameters used for calculation resulting in the figures for TABLE 2 are: 266 nm p-polarized laser beam, 50 nm PSL on bare silicon wafer with the presence of micro-roughness. Power spectral density function for micro-roughness is $0.01/[1+(360f)^2]^{(3.13/2)}$. The polar angle used in the calculation is 70 degrees. In the illustrated embodiment, the first polar angle 1613 of FIG. 16, is 70 degrees.

In TABLE 2, the peak ratio is ratio of the signal S (from the PSL sphere as a sample defect) to the signal N of micro-rough surface (noise). As illustrated, the ratio is greatest at 25 degrees azimuthal angle. This means that it is easiest to distinguish a defect from background noise due to rough surfaces at that angle. Accordingly, in the present example, placement of a retraceable polarizer in front of collectors with 25 degrees azimuthal angle increases the S/N ratio, even in the presence of micro-roughness. Higher S/N ratio is desirable because it is easier to distinguishing defects with higher S/N ratio.

TABLE 2

| Azimuthal Angle $\Phi$ | Peak Ratio: PSL/Micro-roughness | Average Polar Angle $\theta$ of the ring detector |
|---|---|---|
| 15° | 0.2 | 70° |
| 20° | 1.3 | |
| 23° | 4.2 | |
| 25° | 8.1 | |
| 30° | 4.7 | |
| 35° | 1.9 | |
| 40° | 1.1 | |
| 45° | 0.7 | |
| 50° | 0.6 | |
| 60° | 0.4 | |
| 70° | 0.3 | |
| 80° | 0.2 | |

The collection lens 640, the band-pass filter 642, and the polarization filter 644, when used, are enclosed in a light shroud 650 having two openings 652 and 654 with a first opening 652 in the direction toward the field of view (FOV) 1604 and a second opening 654 in a direction opposite the first opening 652 and toward a waveguide 660 such as optical fiber 660. The optical fiber 660 has a first end where light enters the optical fiber 660, the first end proximal to the first opening 652 of the light shield, and a second end where the light exits the optical fiber 660, the second end proximal to a photo detector array 670. The collection lens 640 focuses the field of view (FOV) 1604 onto the first end of the optical fiber 660. The collection lens 640 has a focal length of ranging from 30 mm to 40 mm. Coupling from the FOV 1604 to the first end opening of the optical fiber 660 is a 4-f coupling. That is, distance 656 from the FOV 1604 to the collection lens 640 is twice the focal length of the collection lens 640. Further, distance 658 from the collection lens 640 to the opening of the first end of the optical fiber 660 is also twice the focal length of the collection lens 640. That is, magnification between the field of view 1604 and the first end of the optical fiber 660 is one-to-one.

The optical fiber 660 is a single mode fiber with 0.22 numerical aperture (N.A.) and approximately 1.0 mm silica core. Length of the optical fiber 660 is approximately 0.5 meters, but this can vary. Transmission efficiency through the optical fiber 660 is above 95 percent for 266 nm DUV deep ultra-violet (DUV) light and even higher for 532 nm light. The collection lens 640 has numerical aperture slightly less than that of the optical fiber 660 and produces a focus spot smaller than the optical fiber 660 core within the entire depth of focus of the collection lens 640. Thus, coupling between the collection lens 640 and the optical fiber 660 is optimized and little light is lost and relatively large depth of focus. That is, slight shifts in focus due to slight z-axis movements of the wafer 102 or due to unevenness of the wafer 102 have minimal impact on collection of the scattered light. For example, in one embodiment, the lens 640 has a maximum lateral aberration of 0.7 mm and maximum longitudinal aberration of 10 mm. That is, if the focus shifts by 1 mm (which is within the 10 mm longitudinal aberration range), the light spot at the collection fiber will remain at 0.7 mm diameter.

Scattered light (collected by the collector lens 640 and filtered by the band-pass filter 642 and the polarization filter 644) is focused onto and inserted into the optical fiber 660 which carries the collected scattered light. The light carried by the optical fiber 660 is also referred to as optical signal. The optical fiber 660 guides the optical signal to a photo detector.

As illustrated in FIG. 17A, the optical fiber 660 is bundled 1665 with other optical fibers each of which is coupled with a collector lens from the ring 1610 collectors, and each of which is carrying optical signal collected by the collection lens coupled to it. Here, since the ring 1610 of collectors includes 14 collectors, the bundle 1665 includes 14 fibers.

The bundled 1665 optical fiber is coupled to the array 1670 of photo detectors. FIG. 17B illustrates a front view of the photo detector array 1670. Referring to FIGS. 17A and 17B, the photo detector array 1670 can be an array of photo multiplier tubes (PMTS) or an array of photo detector diodes. Each photo multiplier tube (or each photo detector diode) of the array 1670 is adapted to convert optical signal from an optical fiber into corresponding electrical signal. Each photo multiplier tube or the signal from each photo multiplier tube is often referred to as a pixel. The electrical signal represents the light scattered from the wafer and collected by the collectors. Thus, each pixel value represents the light scattered from the wafer and collected by the collector corresponding to the pixel. The PMT array 1670 is a 4 by 4 array having a PMT for each of the optical fibers.

For convenience, an individual collector lens of the defect review system 1000 (for example the collector lens 640), optical components associated with it (such as the retractable polarization filter 644 or a band-pass filter 642) and the optical fiber coupled to it (such as the optical fiber 660) is referred to as a "channel." Thus, each collector lens is associated with and is a component of a channel. Consequently, the 14-channel defect review system 1000 of the present invention provides 14 pixel resolution of the scattering light signal collected by the collectors. Each of the pixels includes information regarding scattered light for a particular channel associated with a particular collector. Thus, the ring 1610 of collectors preserves angular information regarding the captured scatter light in azimuthal angles within their polar angles.

Each collector collects scattered light from a unique range of collection azimuthal angles relative to the range of collection azimuthal angles of all other collector of the defect review system 1000. This arrangement provides a useful segmentation of angular detection because this arrangement results in no cross talk between the channels of the defect review system 1000.

Figure 17C:
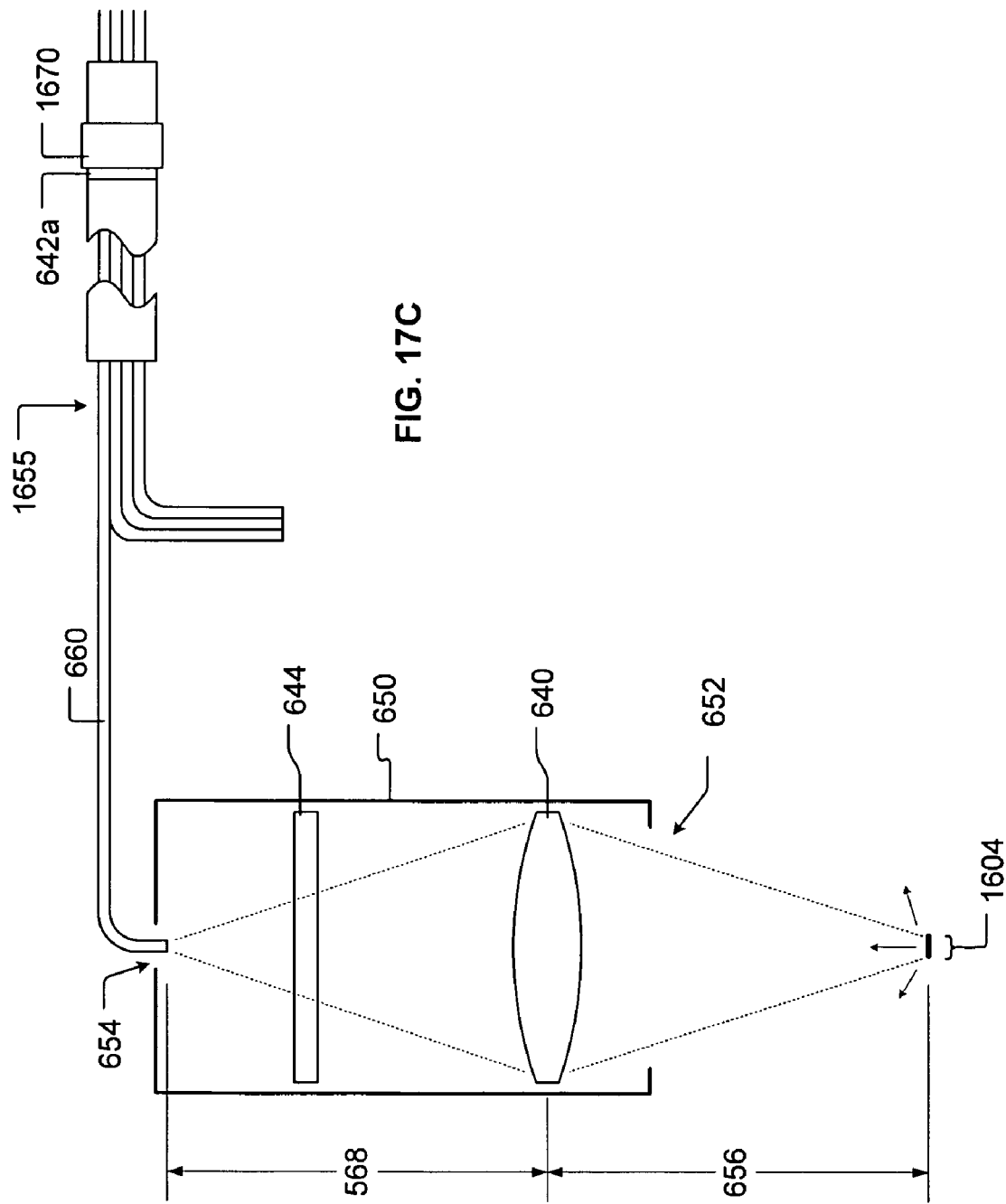
FIG. 17C is a diagram illustrating alternative embodiment of the portion of the defect review system of FIG. 13 as illustrated in FIG. 17A.

FIG. 17C illustrates an alternative embodiment of the additional portions of the defect review system 1000 illustrated in FIG. 17A. In FIG. 17A, one or more collector lens 1640 can be preceded or followed by a band-pass filter 642. This configuration allows for the application of a band pass filter 1642 for selected collector lenses of the defect review system 1000. If a band pass filter 642 is desired for all of the channels of the defect review system 1000, then, a single band pass filter 642a can be used to reduce complexity and cost. The single band pass filter 642a is placed between the second end of the optical fiber 660 and the photo detector array 1670. The single band pass filter 642a is sufficiently large to filter all of the optical fibers 660 directed toward the photo detection sensor array 1670.

Figure 17D:
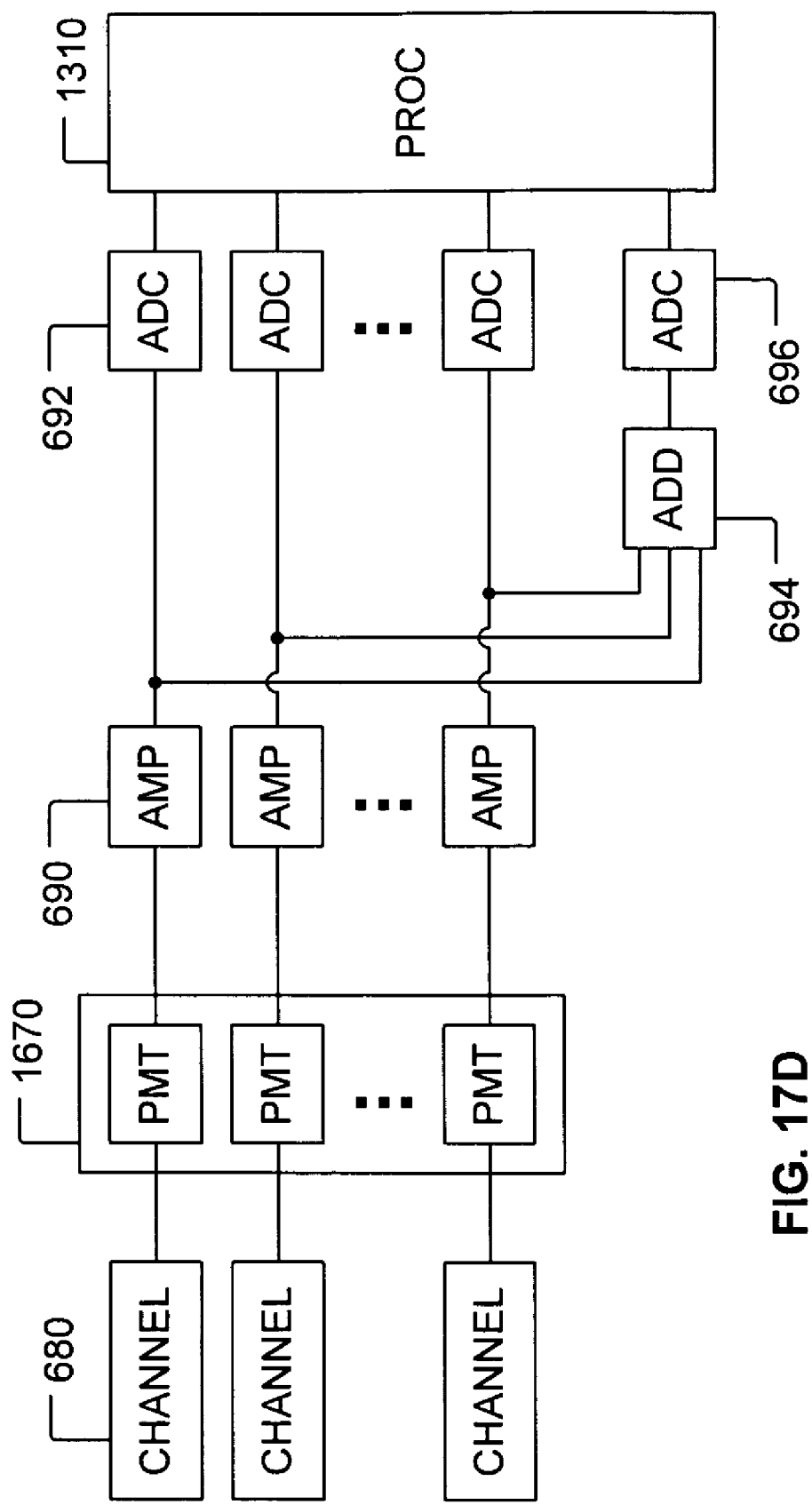
FIG. 17D is a more detailed view of another portion of the defect review system of FIG. 13 in block diagram form.

Referring again to FIG. 17A, optical signal from each optical fiber, for example the optical fiber 660, of the optical fiber bundle 1665 is converted to electrical signal by at least one PMT of the PMT 1670. The electrical signal from each PMT is operated on by electrical circuits as illustrated in FIG. 17D. Referring to FIGS. 17A and 17D, a generic channel is referred to using reference numeral 680. The electrical signal from each PMT is amplified by an amplifier 690 and converted to digital electrical signal by analog-to-digital converter (ADC) 692. Finally, the digitalized electrical signal is sent to a processor 1310. The amplified electrical signal from the amplifiers 690 for each of the PMTS can also be integrated, or added, by an adding circuit 694, digitized by an ADC 696, and forwarded to the processor 1310 for further analysis. That is, the processor 1310 is adapted to process information from the channels.

The processor 1310 is programmed to analyze the digitalized electrical signal received from the ADCS 692, each ADC 692 connected to a channel. Again, each channel carries optical signals collected by one of the collectors of the ring 1610 of collectors. Each collector collects scattered light from a unique range of azimuthal angles relative to all other collector of the defect review system 1000. Accordingly, the processor 1310 is programmed to recognize defects (such as surface imperfections, undesired particles) on the surface 104 of the article 102.

The signal from each channel can either be summed up or processed separately as shown in FIG. 17D and discussed above. Referring to FIG. 17D, for scatter signal from smooth unpatterned wafer where angular information is less important (than the angular information of scatter signal for rough unpatterned wafer), the electrical signal from the photo detector 1670 are often summed for further analysis. Here, as illustrated in 17D, the summation is performed (by the adding circuit 694) before the electrical signal is converted to digital signal by an analog-to-digital convert 696. This minimizes electronic noise.

For scatter signal from rough unpatterned wafer where angular information is relatively more important, electrical signal (from the photo detector 670) from each channel is digitized by the ADC 692 for analysis by the processor 1310. For scatter signal from unpatterned wafer with significant micro-roughness, electrical signal (from the photo detector 670) from selected channels are digitized by the ADC 692 for analysis by the processor 1310. Here, the selected channels are those with polarizers, with bypass-filters, or both.

The dark-field subsystem 1400, in combination with the collection subsystem 1600 and the control subsystem 1300 provides a dark-field mode of operation adapted to inspect the surface by illuminating a spot on the surface at an oblique angle and collecting scattering light from the surface.

G. Bright-field Subsystem 1900

Referring again to FIG. 14, for bright-field illumination of the wafer 102, the polarizing beam splitter 1902 is moved into the path of the light from the lighting subsystem 1500. The light from the lighting subsystem 1500 is reflected by the polarizing beam splitter 1902 toward a quarter wave plate 1904.

The polarizing beam splitter 1902 reflects light polarized in a first direction (for example, p-polarized light) only; thus, at the polarizing beam splitter 1902, approximately 98 percent of the light from the lighting subsystem 1500 is reflected toward the quarter wave plate 1904 while the other 2 percent is lost toward the dark-field subsystem 1400. This is because, the laser 510 can and does, in the present example, generates p-polarized light.

The quarter wave plate 1904 transforms the linearly p-polarized light into a circularly polarized light. Reference numeral 1905 indicates the incoming circularly-polarized light.

The light 1905 is reflected by a mirror within a slider cube assembly 1910 toward the surface 104 of the wafer. The reflected light 1913 from the slider cube assembly 1910 passes though an objective of an objective turret 1920 to impinge on a portion of the surface 104 of the wafer 102 and reflects off from the surface 104 as reflected light 1915.

The reflected light 1915 is again reflected by the mirror of the slider cube assembly 1910 but, this time, toward the quarter wave plate 1904 as returning light 1917. The quarter wave plate 1904 transforms the returning light 1917 back into linearly polarized in such away that the returning light is now 90 degrees rotated relative to the first polarized (p-polarized) light. In fact, the returning light 1917, after passing through the quarter wave plate 1904, is polarized in the second direction (s-polarized).

The s-polarized returning light passes through the polarizing beam splitter 1902 toward a movable bright-field mirror 1930. The movable bright-field mirror 1930 reflects the s-polarized returning light toward an optical sensor 1940. The sensor 1940 converts the reflected light to electrical signal that represent an image of the portion of the surface 104 the light 1913 reflected off from. The sensor 1940 is connected to the processor 1310 (of FIG. 15A). The image analyzed to determine the condition of the portion of the portion of the surface 104 the light 1913 reflected off from such as for existence or location of defects within that portion.

The turret 1920 can include any number of objectives, for example 5. In one embodiment, at least one of the objectives, for example, the first objective 1922 has a numerical aperture of 0.9 and a magnification of 100×. This objective is capable of generating a diffraction limited illumination laser spot on the surface 104 which is about 0.18 microns in diameter. For some applications, a relative small spot size is an important factor in creating a high resolution deep ultra-violet (DUV) light scanning image.

In one embodiment the following objectives are attached to the turret 1920: 8×DUV, 50×LWD (long working distance) DUV, 100×DUV, and 100×Visible. All objectives are infinity corrected. A tube lens is optimized for both 266 nm and 532 nm wavelength radiation. The tube lens is a part of an infinitely corrected microscope system and is within the body 1921 of the turret 1920. The 100×DUV objective is used for high resolution DUV imaging and micro-Raman analysis. The 100× visible objective is used for white light imaging. The 8×DUV is used for wafer alignment, and the 50×LWD DUV is used for redetection of a defect. The turret is motorized and controlled by the processor 1310 (FIG. 15A). When re-detecting defects on an unpatterned wafer, the turret 1920 switches to an empty slot so that no objective is in the vertical beam path. This set up provides the ring 1610 detectors with an unobstructed view to collect scattering light emanating from the field of view.

The returning light 1917 can also be analyzed using a spectrometer 1950. This is accomplished by moving the movable bright-field mirror 1930 out of the path of the returning light 1917 allowing the returning light 1917 to reach the spectrometer 1950. Before reaching the spectrometer 1950, a notch filter 1938 filters the returning light 1917 by blocking 266 nm laser light so that relatively much weaker Raman light can be detected. The spectrometer 1950 detects and records micro-Raman, micro-photoluminescence, and micro-fluorescence spectra of the returning light 1917. The DUV Raman spectroscopy has an advantage over visible Raman analysis in that the later often suffers from overwhelming fluorescence interference while the former does not. In fact, in order for the DUV micro-Raman to work, the 2D scanner 544 needs to stop scanning. A stationary laser spot falls right on top of the defect under analysis.

The bright-field subsystem 1900, in combination with the control subsystem 1300, the turret 1920 and its objectives, provides a bright-field mode of operation adapted to inspect the surface.

H. Marking Subsystem 1700—Marking

Referring to FIGS. 13 and 14, typically, the defect review system 1000 obtains defect location information from a defect inspection system such as the defect inspection system 100 of FIGS. 1–12. Then, the defect review system 1000 is used to further review and analyze these defect locations using the dark-field review technique, the bright-field technique, or both to classify defects and to locate the defects with further accuracy. The defect review system 1000 can also improve the defect coordinate accuracy by identifying and locating the defects with increased resolution using a raster pattern scan technique similar to the raster pattern scan technique used by the inspection system 100 of FIGS. 1–2 and discussed above as the second pass inspection of an unpatterned wafer.

For defects in need of even more analysis by specialized machines such as secondary electron microscope (SEM) with energy dispersive x-ray analysis (EDX) capability, the defect review system 1000 provides more precise defect location coordinate and marks, if necessary, the defect. Moreover, locations of the defects are saved in the storage 1320 of the control subsystem 1300 (of FIG. 15A) as a defect map. In addition, the defect review system 1000 creates several coordinate system reference laser marks at the peripheral of the wafer 102 and includes their locations in the defect map. These marks can be used by a SEM to align its coordinate system with that of the defect review system 1000.

The making of the defect marks and the coordinate system reference marks is performed using a marking subsystem 1700. Portions of the marking subsystem 1700 of the defect review system 1000 is similar to corresponding portions of the marking subsystem 700 of the inspection system 100 of FIGS. 1–12. To avoid clutter or repetition, those portions of the marking subsystem 1700 of the defect review system 1000 that are similar to corresponding portions of the marking subsystem 700 of the inspection system 100 of FIGS. 1–12 are assigned the same reference numerals.

FIG. 10 illustrates a portion 150 of the surface 104 of the wafer 102, the portion 150 including sample defect location 136 to be marked. In FIG. 10, the defect location 136 is indicated as a dashed ellipse.

Referring to FIGS. 10 and 14, to mark the defect location 136, a marking laser 702 is pulsed, or fired, a number of times. Each time the marking laser 702 is pulsed, marking laser beam 703 is generated. The marking laser beam 703 is directed toward the surface 104 where the marking laser beam 703 produces a small crater, or a dot, on the surface 104. Between each pulse of the marking laser 702, the wafer 102 is moved slightly such that, the sequence of dots results in a dotted shape a sample of which is illustrated in FIG. 10 as a defect mark 152 including a circular mark around the defect location 136 and an incomplete cross-hair mark within the circular mark.

Before pulsing the marking laser 702, a marking subsystem first mirror 704 is moved away from the path of the marking laser beam such that the marking laser beam 703, when generated by the marking laser 702, moves unimpeded toward the slider cube assembly 1910. Also, before pulsing the marking laser 702, the mirror of the slider cube assembly 1910 is adjusted to a new position to reflect the marking laser beam 703 toward the surface 104 of the wafer 102 turret or the mirror of the slider cube assembly 1910 is removed and replaced with another mirror to reflect the marking laser beam 703 toward the surface 104 of the wafer 102. For simplicity, the positionally-adjusted mirror or the replacement mirror within the slider cube assembly 1910 is referred to as "the slider cube assembly 1910 mirror."

The slider cube assembly 1910 mirror reflects the marking laser beam 703 from the marking laser 702 toward the surface 104. The laser beam 703 blasts the surface 104 of the wafer 102 to create a single dot. The defect mark 152 is created using a sequence of dots. The marking time for a single dot mark 152 is determined by the laser pulse width (typically a few nanoseconds). However, the marking time for a patterned mark like a cross-hair is decided by the number of individual dot marks required and the amount of time it takes to move to each marking locations. For the present example, the time it takes to generate the defect mark 152 is in the order of a few seconds.

The marking laser 702 provides pulsed beam from either a $N_2$ (Nitrogen) laser or a 532 nm DPSS (Diode Pumped Solid State) laser. The marking laser 702 is connected to the processor 1310 (FIG. 15A). The processor 1310 controls the operations of the marking subsystem 1700 including all the components of the marking subsystem 1700, for example, by controlling the amount of average laser power and the type of pattern for the defect mark 152.

The laser beam 703 is focused on the surface 104 by one of the objectives of the turret 1920. A marking subsystem objective 1924 can be, for example, a 50× long working distance objective lens which is rotated (by the turret 1920) in position to focus the marking laser beam 703 onto the surface 104 of the wafer 102.

The defect mark 152 can have any suitable pattern or shape. In the illustrated embodiment, the defect mark 152 has dimensions 154 in the order of tens of microns, for example 50 microns in diameter.

Coordinate system reference laser marks are illustrated in FIG. 3B as coordinate system reference marks 131. These marks are also created by the marking subsystem 1700 using the marking laser beam 703. For example, three coordinate system reference marks 131 can be made—all three marks near the edge but in different directions. For instance, illustrated in the Figures are three marks, one each on the East edge, North edge, and West edge of the wafer 102 thus allowing the x-axis and the y-axis to be determined from the reference coordinate system marks 131. The coordinate system reference marks 131 are illustrated in FIGS. 3A and 3B as craters. The crater marks 131 are near the edge of the surface 104 as to avoid waste of useful wafer surface area. In alternative embodiments, the coordinate system reference marks 131 can have other shapes.

I. Marking Subsystem 1700—Imaging

Continuing to refer to FIGS. 13 and 14, the marking subsystem 1700 is also used for imaging a portion of the surface to examine a defect or a defect mark previously created. Images taken by marking subsystem imaging array 1720 can be used for defect analysis and defect mark analysis as well as for calibration purposes. The marking subsystem imaging array 720 can be, for example, a CCD camera or a CMOS camera.

To image the a portion of the surface 104 of the wafer 102, light is provided by a marking subsystem lamp 712 such as a halogen lamp to provide imaging light 713, typically a white light. The marking subsystem first mirror 704 is positioned to reflect the imaging light 713 toward a marking subsystem beam splitter cube within the slider cube assembly 1910. A marking subsystem beam splitter cube is provided within the slider cube assembly 1910.

The marking subsystem beam splitter cube (within the slider cube assembly 1910) is positioned to intercept and redirect the imaging light 713 (reflected by the marking subsystem first mirror 704) toward the surface 104 of the wafer 102. The marking subsystem beam splitter cube (within the slider cube assembly 1910) reflects 50 percent of the imaging light 713 toward the surface 104 via one of the objectives of the turret 1920. The imaging light is reflected from the defect location back toward the marking subsystem beam splitter cube (within the slider cube assembly 1910) again via the objective. Half of the reflected light passes through the marking subsystem beam splitter cube (within the slider cube assembly 1910) to be captured by the marking subsystem imaging array 720. The marking subsystem imaging array 720 is connected to the processor 1310. The captured image is forwarded to the processor 1310 for analysis.

J. Defect Review Method 1800

To review a wafer using the defect review system 1000, the wafer is placed on the support and motion subsystem 200 (of FIG. 14). Wafer placement can be fully automated (by a robotic wafer handling system) or performed manually. Both methods are known in the art. Placement accuracy of a robotic wafer handling system approaches hundreds of microns. Manual placement of a wafer typically results in a placement accuracy of one or two millimeters. Once the wafer is placed on the support and motion subsystem 200 (of FIG. 14), vacuum is applied to hold the wafer in place. Typical defect size is in the range of microns, thus systems required for defect review need to have high magnification, and hence small field-of-view. Accordingly, alignment correction may be required.

If the wafer placement error is more than a few tens microns, as is the case of manual wafer placement and some robotic wafer placement, an alignment step is taken to mathematically correct for the placement error. For alignment, the center and orientation of the wafer is located. FIG. 18A is a flowchart 1010 illustrating the steps to locate the center of the wafer 102.

Referring to FIGS. 18A and 18B, four wafer edge points 1022, 1024, 1026, and 1028 are chosen. Step 1020. The four wafer edge points 1022, 1024, 1026, and 1028 are away from the flat 1012 or the notch. Generally, the four wafer edge points 1022, 1024, 1026, and 1028 are at approximately regularly spaced around the wafer 102 relative to each other; however, it is not critical that they be evenly spaced around the wafer 102. To locate each wafer edge point, a series of images are taken beginning inside the nominal wafer edge and continuing away from the center until the wafer edge is found. To take each image in the series of images, auto focus is performed to obtain consistent image quality to compensate for rounded and tapered edges.

A first line LINE1 1032 is defined, LINE1 1032 intersecting the first edge point P1 1022 and the third edge point P3 1026, and LINE1 1032 having a midpoint 1034 between the two edge points P1 1022 and P3 1026. Step 1030. A second line LINE2 1042 is defined, LINE2 1042 intersecting the second edge point P2 1024 and the fourth edge point P3 1028, and LINE2 1042 having a midpoint 1044 between the two edge points P2 1024 and P4 1028. Step 1040.

Next, a third line LINE3 1052 is defined, LNE3 1052 orthogonal to the first line LINE1 1032 and intersecting the midpoint 1034 of the first line LINE1 1032. Step 1050. A fourth line LINE4 1062 is defined, LINE4 1062 orthogonal to the second line LINE2 1042 and intersecting the midpoint 1044 of the second line LINE2 1042. Step 1060. Finally, the center 1072 of the wafer is located as the intersection point 1072 of the third line 1052 and the fourth line 1062.

Once the center 1072 of the wafer 102 is established, the wafer flat 1012 or notch (not shown) can be similarly found by finding the wafer edge points around the nominal flat or notch position, and fitting the appropriate flat or notch profile to the actual flat or notch edge points.

For patterned wafers, a de-skew process is performed so that the coordinate system of the defect review system 1000 and the coordinate system of the equipment that generates the defect map can be matched. Two or more fiducial marks at known locations are imaged and matched either manually or automatically to one in a set of previously stored fiducial images. The offsets between the test fiducial images and the matched stored fiducial images produce a correction matrix that corrects the defect map's location to the defect review system 1000's Cartesian coordinate system.

Referring to FIG. 14, whether the surface 104 of the wafer 102 is reviewed using the dark-field illumination technique or the bright-field illumination technique, a relatively large area of the surface 104 of the wafer 102 can be reviewed by moving one or more laterally moving stages 204 and 206 (illustrated in FIG. 14). For dark-field illumination, in addition to or in combination with the movement of the lateral stages 204 and 206, the 2D scanner 544 can redirect and cause the illuminating light from the laser 510 to form a rectangular raster pattern on the surface 104 over a relatively large area as illustrated in FIG. 9 and discussed above. The rectangular scan area 130 can have lateral dimensions in the order of hundreds of microns, for example, 600 microns by 600 microns.

To review a patterned wafer 102*p*, the bright-field subsystem 1900 is used to obtain a high resolution DUV image which is analyzed to locate defects. Once a defect is located, the high resolution DUV image is used to classify the defect. The high resolution DUV image is obtained from the sensor 1940 as discussed above. For further analysis, the marking subsystem 1700 is used to obtain a bright-field white light image of the defect. The white light image is obtained from the imaging array 720 as discussed above. For even more analysis of the defect, a spectrum analysis of the bright-field DUV image of the defect is analyzed. The bright-field DUV image is obtained by the bright-field subsystem 1900 and its spectrum analyzed by the spectrometer 1950 as discussed above.

Although specific embodiments of the invention are described and illustrated above, the invention is not to be limited to the specific forms or arrangements of parts so described and illustrated. For example, differing configurations, sizes, or materials may be used but still fall within the scope of the invention. The invention is defined by the claims that follow.

We claim:

1. An inspection system comprising:
a stage operable to support an article for inspection, the article having a surface;
a light source adapted to provide light impinging on and scattering from an illumination area of the surface;
a first ring of collectors adapted to collect the scattered light, said first ring of collectors positioned at a first ring polar angle and said first ring of collectors comprising a set of collectors;
a second ring of collectors adapted to collect the scattered light, said second ring of collectors positioned at a second ring polar angle and said second ring of collectors comprising a set of collectors;
a third ring of collectors adapted to collect the scattered light, said third ring of collectors positioned at a third ring polar angle and said third ring of collectors comprising a set of collectors;
a plurality of channels wherein each collector of said first ring of collectors, said second ring of collectors, and said third ring of collectors is associated with a channel; and
a processor connected to the channels, said processor adapted to process information from the channels;
wherein each channel comprises a waveguide to guide collected light to a photo detector adapted to convert the collected light into electrical signal, and an amplifier connected to the photo detector, wherein said amplifier operable to amplify the electrical signal and an analog-to-digital converter operable to convert the amplified electrical signal to digital electrical signals.

2. The inspection system recited in claim 1 wherein said stage is operable to rotate the article about a center of rotation.

3. The inspection system recited in claim 1 wherein said stage is operable to translate the article in lateral axis.

4. The inspection system recited in claim 1 wherein each collector comprises a lens.

5. The inspection system recited in claim 4 wherein the collection lens has a large depth of focus.

6. The inspection system recited in claim 1 further comprising a first adapted to direct the light from said light source toward the illumination area at a first incident angle.

7. The inspection system recited in claim 6 further comprising a turning mirror adapted to direct the light from said tight source toward the illumination area at a second incident angle.

8. The inspection system recited in claim 1 wherein at least one channel comprises a band-pass filter, said band-pass filter adapted to allow light having a predetermined wavelength to pass.

9. The inspection system recited in claim 1 wherein at least one channel comprises a polarization filter proximal to its associated collector, said polarization filter adapted to allow light having a predetermined polarization to pass.

10. The inspection system recited in claim 9 wherein the polarization filter is an s-polarized fitter.

11. The inspection system recited in claim 1 further comprising a photo detector array connected to a bundle of channels, said photo detector array comprising an array of photo multiplier tubes (PMTS), each PMT adapted to convert optical signal from a channel to electrical signal.

12. The inspection system recited in claim 1 wherein said stage comprises:
an x-axis stage;
a y-axis stage;
a z-axis stage; and
a rotational stage.

13. An inspection system comprising:
a stage operable to support an article for inspection, the article having a surface;
a light source operable to provide light impinging on and scattering from an illumination area of the surface;
a light collection subsystem including a plurality of collectors, the collectors arranged generally in a semi-spherical layout such that each collector collects at least a portion of the scattering light at a collection polar angle and a collection azimuthal angle that are unique relative to collection polar angle and collection azimuthal angle of other collectors;
wherein each collector is associated with a channel;
a plurality of channels wherein each collector of said light collection subsystem is associated with a channel; and
a processor connected to the channels, said processor adapted to process information from the channels;
wherein each channel comprises a waveguide to guide collected light to a photo detector adapted to convert the collected light into electrical signal, and an amplifier connected to the photo detector, wherein said amplifier operable to amplify the electrical signal and an analog-to-digital converter operable to convert the amplified electrical signal to digital electrical signals.

14. The inspection system recited in claim 13 wherein said stage is operable to rotate the article about a center of rotation and to move the article laterally.

15. The inspection system recited in claim 14 wherein each of the collectors is a lens.

16. The inspection system recited in claim 13 further comprising a first mirror adapted to direct the light from said light source toward the illumination area at a first incident angle.

17. The inspection system recited in claim 16 further comprising a turning mirror adapted to direct the light from said light source toward the illumination area at a second incident angle.

18. The inspection system recited in claim 17 further comprising a band-pass filter between the illumination area and a first collector, said band-pass filter adapted to allow light having a predetermined wavelength to pass.

19. The inspection system recited in claim 13 further comprising a polarization filter proximal to a first collector, said polarization filter adapted to allow light having a predetermined polarization to pass.

20. The inspection system recited in claim 13 further comprising a photo detector array connected to a bundle of channels, said photo detector array comprising an array of photo multiplier tubes (PMTS), each PMT adapted to convert optical signal from a channel to electrical signal.

* * * * *